US008333965B2

(12) United States Patent
Banchereau et al.

(10) Patent No.: US 8,333,965 B2
(45) Date of Patent: Dec. 18, 2012

(54) ANTI-INTEFERON ALPHA MONOCLONAL ANTIBODIES AND METHODS FOR USE

(75) Inventors: Jacques Banchereau, Dallas, TX (US); Kiley Prilliman, Dallas, TX (US); Virginia Pascual, Dallas, TX (US); Anna Karolina Palucka, Dallas, TX (US)

(73) Assignee: Baylor Research Institute, Dallas, TX (US)

( * ) Notice: Subject to any disclaimer, the term of this patent is extended or adjusted under 35 U.S.C. 154(b) by 0 days.

(21) Appl. No.: 13/252,335

(22) Filed: Oct. 4, 2011

(65) Prior Publication Data

US 2012/0020963 A1     Jan. 26, 2012

Related U.S. Application Data

(62) Division of application No. 11/883,961, filed as application No. PCT/US2006/004643 on Feb. 9, 2006, now Pat. No. 8,080,638.

(60) Provisional application No. 60/652,233, filed on Feb. 10, 2005.

(51) Int. Cl.
*A61K 39/395*    (2006.01)
*A61K 38/00*    (2006.01)
*C07K 16/00*    (2006.01)
*C12P 21/08*    (2006.01)

(52) U.S. Cl. ............... 424/130.1; 424/133.1; 424/145.1; 514/18.7; 530/387.1; 530/388.23

(58) Field of Classification Search ........................ None
See application file for complete search history.

(56) References Cited

U.S. PATENT DOCUMENTS

| | | | |
|---|---|---|---|
| 4,362,155 A | 12/1982 | Skurkovich | |
| 4,423,147 A | 12/1983 | Secher et al. | |
| 4,474,754 A | 10/1984 | Shimizu et al. | |
| 4,605,394 A | 8/1986 | Skurkovich | |
| 4,824,432 A | 4/1989 | Skurkovich et al. | |
| 4,902,618 A | 2/1990 | Berg | |
| 4,973,556 A | 11/1990 | Bove et al. | |
| 5,055,289 A | 10/1991 | Frincke et al. | |
| 5,886,153 A | 3/1999 | Mogensen et al. | |
| 5,888,511 A | 3/1999 | Skurkovich et al. | |
| 5,889,151 A | 3/1999 | Mogensen et al. | |
| 5,919,453 A | 7/1999 | Benoit et al. | |
| 6,136,309 A | 10/2000 | Novick et al. | |
| 6,333,032 B1 | 12/2001 | Skurkovich et al. | |
| 6,458,932 B1 | 10/2002 | Novick et al. | |
| 6,458,934 B1 | 10/2002 | Hong et al. | |
| 6,475,983 B1 | 11/2002 | Eid et al. | |
| 6,660,523 B2 | 12/2003 | Blom et al. | |
| 6,713,609 B1 | 3/2004 | Chuntharapai et al. | |
| 6,787,634 B2 | 9/2004 | Benoit et al. | |
| 7,087,726 B2 | 8/2006 | Chuntharapai et al. | |
| 7,179,465 B2 | 2/2007 | Benoit et al. | |
| 7,544,357 B2 | 6/2009 | Banchereau et al. | |
| 7,888,481 B2 | 2/2011 | Banchereau et al. | |
| 8,080,638 B2 | 12/2011 | Banchereau et al. | |
| 8,163,885 B2 | 4/2012 | Svensson et al. | |
| 2002/0160974 A1 | 10/2002 | Banchereau et al. | |
| 2003/0018174 A1 | 1/2003 | Kim et al. | |
| 2003/0021764 A1 | 1/2003 | Maroun | |
| 2003/0147889 A1 | 8/2003 | Tovey | |
| 2003/0166228 A1 | 9/2003 | Chuntharapai et al. | |
| 2004/0067232 A1 | 4/2004 | Banchereau et al. | |
| 2004/0067888 A1 | 4/2004 | Tovey et al. | |
| 2004/0132139 A1 | 7/2004 | Escary | |
| 2004/0170626 A1 | 9/2004 | Schuurman et al. | |
| 2004/0191840 A1 | 9/2004 | Benoit et al. | |
| 2005/0013799 A1 | 1/2005 | Skurkovich et al. | |
| 2005/0013800 A1 | 1/2005 | Skurkovich et al. | |
| 2005/0013813 A1 | 1/2005 | Maroun | |
| 2007/0014724 A1 | 1/2007 | Witte et al. | |
| 2007/0048311 A1 | 3/2007 | Chuntharapai et al. | |
| 2009/0155286 A1 | 6/2009 | Gilliet et al. | |
| 2009/0263474 A1 | 10/2009 | Banchereau et al. | |
| 2009/0324605 A1 | 12/2009 | Witte et al. | |

FOREIGN PATENT DOCUMENTS

EP            032541 A1     7/1989
(Continued)

OTHER PUBLICATIONS

Chuntharapai et al. (2001), Cytokine, vol. 15, No. 5, pp. 250-260.*
Ronnblom et al., "Role of natural interteron-[alpha] producing cells (plasmacyloid dendritic cells) . . . " Autoimmunity (2003) pp. 463-472, vol. 36.
Ronnblom and Alm, "An etiopathogenic role for the type I IFN system in SLE," Trends Immunol. (2001) pp. 427-431, vol. 22.
Ronnblom and Alm, "A pivotal role for the natural interferon alpha-producing cells . . . " J. Exp. Med. (2001) pp. F59-F63, vol. 194.
Santiago-Raber et al., "Type-I interferon receptor deficiency reduces lupus-like disease in MZB mice," J. Exp. Med. (2003) pp. 777-788, vol. 197.
Schattner et al., "Review: Interferons and autoimmunity," Am J. Med. S. (1988) pp. 532-544 vol. 295.
Shearer et al., "Monoclonal antibodies that distinguish between subspecies of human interferon-alpha . . . " J. Immunol. (1984) pp. 3096-3101, vol. 133.

(Continued)

*Primary Examiner* — Christine J Saoud
*Assistant Examiner* — Jegatheesan Seharaseyon
(74) *Attorney, Agent, or Firm* — Elaine T. Sale; Leigh W. Thorne

(57) ABSTRACT

The present invention includes compositions and methods that include antibodies that selectively neutralize a bioactivity of at least two interferon alpha ("IFNα") protein subtypes for the protein subtypes A, 2, B2, C, F, G, H2, I, J1, K, 4a, 4b and WA, but does not neutralize at least one bioactivity of IFNα protein subtype D. Examples of bioactivity for measurement include activation of the MxA promoter or antiviral activity and variants, derivatives and fragments thereof. The invention also includes host cells, hybridomas and plasmacytomas that produce antibodies. Because of their unique selectivity and affinity, the antibodies of the present invention are useful to detect IFNα subtypes in sample or tissue and/or for therapeutic applications that include, but are not limited to the treatment and/or amelioration of an IFNα related disorder such as SLE, lupus, type I diabetes, psoriasis, AIDS and Graft versus Host Disease.

12 Claims, 12 Drawing Sheets

FOREIGN PATENT DOCUMENTS

| | | | |
|---|---|---|---|
| EP | 1851248 A | 8/2006 | |
| EP | 2236156 A2 | 10/2010 | |
| WO | 9304699 A1 | 3/1993 | |
| WO | 9806431 A2 | 2/1998 | |
| WO | 9828001 A1 | 7/1998 | |
| WO | 0022093 A2 | 4/2000 | |
| WO | 0024417 A1 | 5/2000 | |
| WO | 0136487 A2 | 5/2001 | |
| WO | 0154721 A1 | 8/2001 | |
| WO | 0155215 A1 | 8/2001 | |
| WO | 03066649 A2 | 8/2002 | |
| WO | WO 02066649 A2 * | 8/2002 | |
| WO | 02067760 A2 | 9/2002 | |
| WO | 2004003211 A1 | 1/2004 | |
| WO | 2004094473 A2 | 11/2004 | |
| WO | 2005059106 A3 | 6/2005 | |
| WO | 2006037247 A1 | 4/2006 | |
| WO | 2008021976 A2 | 2/2008 | |
| WO | 2009135861 A2 | 11/2009 | |

OTHER PUBLICATIONS

Skurkovich et al., "Lymphocytes' cytotoxicity towards cells of human lymphoblastoid lines in patients . . . ," Annals of Allergy (1977) pp. 344-350, vol. 39.

Skurkovich et al., "The use of antibodies to cytokines (anti-IFN-[alpha], anti-IFN-[gamma]; . . . , " Cytokine (1997) p. 899, vol. 9 (meeting abstract).

Skurkovich et al., "Anticytokine therapy—new approach to the treatment of autoimmune and cytokine-disturbance diseases," Med. Hypotheses (2002) pp. 770-780, vol. 59.

Staehelin et al., "Production of hybridomas secreting, monoclonal antibodies to the human leukocyte interferons." Proc. Nat'l. Acad. Sci. USA (1981) pp. 1848-1852, vol. 78.

Stewart, "Neutralizing interferon alpha as a therapeutic approach to autoimmune diseases," Cytokine Growth Factor Rev. (2003) pp. 139-154. vol. 14.

Tsukui et al., "A monoclonal antibody with broad reactivity to human interferon-alpha subtypes . . . ," Microbiol. Immunol. (1986) pp. 1129-1139. vol. 30.

Vancova et al., "The carboxyterminal domains of human IFN-alpha2 and IFN-alpha8 are antigenically homologous," J. Interferon Cytokine Res. (2000) pp. 455-461, vol. 20.

Vilcek et al., "The role of interferon in AIDS," in Friedman-Klein & Laubenstein, eds., "AIDS: The epidemic of Karposi's sarcoma . . . ," (1986), pp. 193-198 (Masson Pub., NY, NY).

Viscomi et al., "Antigenic characterization of recombinant, lymphoblastoid, and leukocyte IFN-alpha . . . " J. Interferon Cytokine Res. (1999) pp. 319-326, vol. 19.

Weber at al., "Single amino acid changes that render human IFN-alpha 2 biologically active on mouse cells," EMBO J. (1987) pp. 591-598, vol. 6.

Zagury et al. "Anti-IFN alpha immunization raises the IFN alpha-neutralizing capacity of serum . . . ," Biomed. Pharmacother. (1999) pp. 90-92, vol. 53.

Barasoain et al., "Antibodies against a peptide representative of a conserved region of human interferon-alpha," J. Immunol. (1989), pp. 507-512, vol. 143.

Bissonnette et al., "A randomized, double-blind, placebo-controlled, phase I study of MEDI-545, an anti-interferon-alpha monoclonal antibody, in subjects with chronic psoriasis," J. Am. Acad. Dermatol. (2010), pp. 427-36, vol. 62.

Boyman et al., "Spontaneous development of psoriasis in a new animal model shows an essential role for resident T cells and tumor necrosis factor-[alpha]," J. Exp. Med. (2004), pp. 731-736, vol. 199.

Brand et al., "Antibodies developing against a single recombinant interferon protein may neutralize many other interferon-alpha subtypes," J. Interferon Res. (1993), pp. 121-125, vol. 13.

Cassett et al., "A peptide mimetic of an anti-CD4 monoclonal antibody by rational design," Biochem Biophys. Res. Comm. (2003), pp. 198-205, vol. 307.

Chang et al., "Molecular and functionalanalysis of the virus- and interferon-inducible human MxA promoter" Arch. Virol. (1991), pp. 1-15, vol. 117.

Chaudhar et al., "Efficacy and safety of infliximab monotherapy for plaque-type psoriasis: a randomised trial" Lancet (2001), pp. 1842-1847, vol. 357.

Chen et al., "Selection and analysis of an optimized ant-VEGF antibody: crystal structure of an affinity-matured Fab in complex with antigen," J. Mol. Biol. (1999), pp. 865-881, vol. 293.

Colamonici and Domanski, "Idenfitication of a novel subunit of the Type I interferon receptor localized to human chromosome 21," J. Biol. Chem. (1993), pp. 10895-10899, vol. 268.

Criste et al., "Pharmacokinetics and immunogenicity of sifalimumab, an anti-interferon-a monoclonal antibody administered subcutaneously in systemic lupus erythematosus," Abstract THU0434 presented at EULAR 2011 Conference May 2011.

DePascalis et al., "Grafting of abbreviated complementarity determining regions containing specificity determining residues essential for ligand contact to engineer a less immunogenic humanized monoclonal antibody," The J. of Imm. (2002), pp. 3076-3084, vol. 169.

Morel at al,, "Anti-CD4 monoclonal antibody therapy in severe psoriasis," J. Autoimm. (1992), pp. 465-477, vol. 5.

Dzionek et al., "BDCA-2, a novel plasmacytoid dendritic cell-specific type II C-type lectin, mediates antigen capture and is a potent inhibitor of interferon [alpha]/ [beta] induction," J. Exp. Med. (2001), pp. 1823-1834, vol. 194.

Fletcher et al., "Clinical and preclinical studies with ANA773, an oral prodrug of a TLR7 agonist, suggest . . . ," (2009) Anadys Pharms., Inc., the Henry M. and Lillian Stratton Basic Research Single topic Conference, Atlanta, Georgia; and Figure 5 legend.

Fray et al., "Validation of an Mx/CAT reporter gene assay for the quantification of bovine type 1 interferon," J. Immunol. Meth. (2001), pp. 235-244, vol, 249.

Goeddel et al. "The structure of eight distinct cloned human leukocyte interferon cDNAs," Nature (2981), pp. 20-26, vol. 290.

Gottleib et al., "Anti-CD4 monoclonal antibody treatment of moderate to severe psoriasis vulgaris: results of a pilot, multicenter, multiple-dose, pacebo-controlled study," J. Am Acad. Dermatol (2000), pp. 595-604, vol. 43.

Holm et al., "Functional mapping and single chain construction of the anti-cytokeratin-eight monoclonal antibody TS1," Mol. Immunol. (2007), pp. 1075-1084, vol. 44.

Iyer et al., "Characterization of human interferon species using gel extraction and monoclonal antibodies: implications on clinical use of interferon preparations," J. Biol. Response Mod. (1966), pp. 548-561, vol. 5.

Kandefer-Szerszen and Lundgren, "Three separate epitopes on human interferon-Alpha variants defined by monoclonal antibodies and their role in the binding to receptors," Arch Immunol. Ther Exp (Warsz.) (1992), pp. 241-246, vol. 40.

Kashmiri et al., "SDR grafting—a new approach to antibody humanization" Methods (2005), pp. 25-34, vol. 36.

Lazar et al., "A molecular immunology approach to antibody humanization and functional optimization," Mol. Immunol. (2007), pp. 1986-1998, vol. 44.

Lipscomb and Masten, "Dendritic cells: immune regulators in health and disease," Physiol. Rev. (2002), pp. 97-130, vol. 82.

Little et al., "Of mice and men: hybridoma and recombinant antibodies," Immunol. Today (2000), pp. 364-370 vol. 21.

MacCallum et al. "Antibody-antigen interactions: contact analysis and binding site topography," J. Mol. Biol. (1996). pp. 732-745, vol. 262.

Maennel et al., "A rat monoclonal antibody against mouse alpha and beta interferon of all molecular weight species," Nature (1982), pp. 664-665, vol. 296.

McKenna et "Plasmacytoid dendritic cells: linking innate and adaptive immunity," J. Virol. (2005), pp. 7-27, vol. 79.

McMullen et al., "Anti-peptide antibodies against conserved regions of human interferons-alpha: evidence for conformational variations between interferon-alpha subtypes," Biochem. Int'l. (1990), pp. 261-269, vol. 21.

Meager et al., "Development of interferon-specific monoclonal antibody for in vitro interferon assays," Dev. Biol. Stand. (1986). pp. 237-248, vol. 64.

Mease et al., "Etanercept who in the treatment of psoriatic arthritis and psoriasis: a randomized trial" Lancet (2000), pp. 385-390, vol. 356.

Medimmune, "Medimmune expands anti-interferon-alpha program by initiating phase 1 trial in patients with psoriasis" Medimmune Social Media Press Room, Mar. 23, 2007, 2 pages.

Merrill et al., "Results of randomized, placebo-controlled, phase 2A study of sifalimumab, an anti-interferon-alpha monoclonal antibody, administered subcutaneously in subjects with systemic lupus erythematosus," Abstract THU0411present and EULAR 2011 Conference May 2011.

Murphy, "PDC-derived interferon-alpha is a master cytokine in psoriasis development," Nat. Clin. Prac. Rheum. (2005), p. 9, vol. 1.

Nestle and Gilliet, "Defining upstream elements of psoriasis pathogenesis: an emerging role for interferon one," J. Invest. Dermatol. (2005), pp. xiv-xv, vol. 125.

Ngo et al., "Computational complexity, protein structure prediction, and the Levinthal paradox," in The Protein Folding Problem and Tertiary Structure Prediction (1994) pp. 491-495 (Birkhaeuser, Boston, MA, US).

Nolte et al., "Epitopes recognized by neutralizing therapy-induced human anti-interferon-alpha antibodies are localized within the N-terminal functional domain of recombinant interferon-alpha 2," Eur. J. Immunol. (1996), pp. 2155-2159, vol. 26.

Novick et al., "Monoclonal antibodies to human alpha-interferon and they use for affinity chromatography," J. Immunol. (1982), pp. 2244-2247, vol. 129.

Oh et al., "Treatment with anti-tumor necrosis factor alpha (TNF-alpha) monoclonal antibody dramatically decreases the clinical activity of psoriasis lesions," J Am Acad. Dermatol. (2000). pp. 829-830, vol. 42.

Anonymous, "On Line Catalog Data Sheet for Anti-Interferon Alpha Antibodies" rev. Mar. 8, 2001, available from Research Diagnostics at http://www.researchd.com/cytokines/ifnachart.htm (printed Feb. 10, 2004).

Anonymous, PBL InterferonSource, Product Insert; Mouse Monocional Antibody Against Human Interferon Alpha (MMHA-1); Product No. 21105-1, date unknown.

Pestka et al., "interferon standardization and designations," J. Inf. Cytokine Res. (1997), pp. S9-S314, vol. 17 Supp. 1.

Quesada and Gutterman, "Psoriasis and alpha-interferon," Lancet (1986), pp. 1466-1468, vol. 1.

Ronni et al., "The proximal interferon-stimulated response elements are essential for interferon responsiveness: a promoter analysis of the antiviral MxA gene," J. Inf. and Cytokine Res. (1998), pp. 773-781, vol. 18.

Rudikoff et al., "Single amino acid substitution altering antigen-binding specificity," Proc. Nat'l. Acad. Sci. (1982) pp. 1979-1983, vol. 79.

Sattayasai et al., "Universal antibodies to human interferon-alpha subtypes—the production of anti-peptide antibodies to conserved regions of interferon-alpha," J. Inf. Res. (1991), pp. 41-48, vol. 11.

Sattayasai et al., "Subtype-specificity of anti-peptide antibodies raised against unique sequences of human interferons-alpha," Mol. Immunol. (1991), pp. 975-983, vol. 28.

Schmid et al. "The Type 1 interferon system is locally activated in psoriatic lesions," J. Inf. Res. (1994), pp, 229-234, vol. 14.

Schmidt and Ouyang, "Targeting interferon alpha: a promising approach for systemiclupus erythematosus therapy," Lupus (2004), pp. 348-352, vol. 13.

Taylor-Papdimitriou et al., "Epitopes of human interferon-alpha defined by the reaction of monoclonal antibodies with alpha interferon sent interferon analogues," J. Immunol. (1967). pp. 3375-3381, vol. 139.

Vajdos et al., "Comprehensive functional maps of the antigen-binding site of an anti-ERB2 antibody obtained with shotgun scanning mutagenesis," J. Mol. Biol. (2002), pp. 415-428, vol. 320.

Petri et al., "Sifallmumab, a fully human anti-interferon-alpha monoclonal antibody, in subjects with . . . SLE . . . ," Abstract OP0169 presented at EULAR 2011 Conference, London, United Kingdom.

Van Der Fits et al., "In psoriasis lesional skin the Type I interferon signaling pathway is activated, whereas interferon-alpha sensitivity is unaltered," J. Invest. Dermatol (2004), pp. 51-60, vol. 122.

Wells, "Additivity of mutational effects of proteins," Biochemistry (1990), pp. 8509-8517, vol. 29.

Wollenberg et al., "Plasmacytoid dendritic cells: a new cutaneous dendritic coli subset with distinct role in inflammatory skin diseases," J. Invest Dermatol. (2002), pp. 1096-1102, vol. 119.

Wu et al., "Humanization of a murine monoclonal antibody by simultaneous optimization of framework and CDR residues," J. Mol. Biol. (1999), pp. 151-162, vol. 204.

Yao et al., "Type I interferon: potential therapeutic target for psoriasis?", PLOS One (2008), pp. 1-14, vol. 3, e2737.

Seharaseyon, International Preliminary Report on Patentability mailed Oct. 6, 2008 for Int. App. No. PCT/US06/04643, filed Feb. 9, 2006.

Hermann, International Search Report mailed Aug. 11, 2006 for Int. App. No. PCT/US06/04643, filed Feb. 9, 2006.

Raanani et al., "Immune-mediated complications during interferon therapy in hematological patients," Acta Haematol. (2002) pp. 133-144, vol. 107.

Adolf et al., "Production of monoclonal antibodies to human IFN-alpha and their use for analysis of the antigenic composition of various natural interferons," J. Cell Physiol. Suppl. (1982), pp. 61-68, vol. 2.

Alexenko et al., "Reconstruction of an epitope capable of binding murine monoclonal antibodies NK2 within the sequence of of human leukocyte interferon alpha F by site-direoted mutagenesis," Blochern. Biophys. Res. Commun. (1990), pp. 1061-1067, vol. 29.

Alexenko et al , "Mapping of an epitope of human, leukocyte alpha interferon A which is recognized by the murine monoclonal antibody NK2," Biomed. Sci. (1991), pp. 403-409, vol. 2.

Andersson et al., "Application of four anti-human interferon-alpha monoclonal antibodies for immunoassay and comparative analysis of natural interferons-alpha mixtures," J. Interferon Res. (1991), pp. 53-60, vol. 11.

Andzhaparidze et al., "Preparation of hybridornas producing monoclonal antibodies against human interferon," Acta Virol. (1988), pp. 481-486, vol. 32.

Alkan and Braun, "Epitope mapping of human recombinant interferon alpha molecules by monoclonal antibodies," Ciba Found. Symp. (1986), pp. 264-278, vol. 119.

Baechler et al., "Interferon-inducible gene expression signature in peripheral blood cells of patients with . . . lupus," Proc. Nat'l. Acad. Sci. USA (2003). pp. 2610-2615, vol. 100.

Banchereau et al., "Autoimmunity through cytokine-induced dendritic cell activation," Immunity (2004), pp. 539-550, vol. 20.

Bave et al., "Fc[gamma]Rlla is expressed on natural IFN-[alpha]-producing cells . . . ," J. Immunol. (2003) pp. 3296-3302, vol. 171.

Bennett et al., "Interferon and granulopoiesis signatures in systemic Lupus erythematosus blood," J. Exp. Med. (2003) pp. 711-723, vol. 197.

Berg, "Identification, production, and characterization of murine monoclonal antbody (LO-22) . . . ," J. Interferon Res. (1984), pp. 481-491, vol. 4.

Bjorck, "Dendritic cells, exposed to herpes simplex virus in vivo do not produce IFN-alpha after rechallenge . . . ," J. Immunol. (2004), pp. 5396-5404, vol. 172.

Blanco et al., "Induction of dendritic cell differentiation by IFN-alpha in systemic lupus erythematosus," Science (2001), pp. 1540-1543, vol. 294.

Blank et al.. "Identification of a linear epitope of interferon-alpha 2b recognized by neutralizing monoclonal antibodies." Eur. J. Biochem. (1999), pp. 11-19, vol. 265.

Blomberg et al., "Expression of the markers BDCA-2 and BDCA-4 and production of interferon-alpha . . . ," Arthritis Rheum. (2003), pp. 2524-2532, vol. 48.

Braun et al., "Type I interferon controls the onset and severity of autoir une manifestations in lpr mice, " Autoimmun. (2003) pp. 15-25, vol. 20.

Chuntharapai et al., "Characterization and humanization of a monoclonal antibody that neutralizes human leukocyte. interferon . . . ," Cytokine (2001) pp. 250-260, vol. 15.

Crow and Kirou, "Interferon-alpha in systemic lupus erythematosus," Curr. Opin. Rheumatol. (2004) pp. 541-547, vol. 16.

Crow, "Interferon-alpha: a new target for therapy in systemic lupus erythematosus." Arthritis Rheum. (2003) pp. 2396-2401, vol. 48.

Devendra and Eisenbarth, "Interferon alpha—a potential link in the pathogenesis of viral-induced type I diabetes . . . ," Clin. Immunol. (2004) pp. 225-233, vol. 111.

Exley et al., "A comparison of the neutralizing properties of monoclonal and polyclonal antibodies to human interferon alpha," J. Gen. Virol. (1984) pp. 2277-2280, vol. 65.

Files et al., "A novel sensitive and selective bioassay for human type I Interferons," J. Interferon Cytokine Res. (1998) pp. 1019-1024, vol. 18.

Fish et al., "The role of three domains in the biological activity of human interfer i-alpha," J. Interferon Res. (1989) pp. 97-114, vol. 9.

Foster et al., "IFN-alpha subtypes differentially affect human T cell motility," J. Immunol. (2004) pp. 1663-1670, vol. 173.

Green et al., "IgG-derived Fc down-regulates virus-induced plasmacytoid dendritic cell (pDC) IFN[alpha] production," Cytokine (2004) pp. 209-216, vol. 26.

Gringeri et al., "Active anti-interferon-alpha immunization: a European-Israeli, randomized, double-blind . . .," J. AIDS Hum. Retrovirol. (1999) pp. 358-370, vol. 20.

Gringeri et al., "Absence of Clinical, Virological,and Immunological Signs of Progression . . . " J. AIDS Hum. Retrovirol. (1996) pp. 55-67, vol. 13.

Gringeri et al., "Anti-alpha interferon immunization: safety and immunogenicity . . . ," Cell. Mol. Biol. (Noisy-le-Grand) (1995) pp. 381-387, vol. 41.

Huang et al . "Islet expression of IFN-[alpha] precedes diabetes in both the BB rat and streptozotocin-treated mice," Immunity (1994) pp. 469-478, vol. 1.

Huang et al., "Interferon expression in the pancreases of patients with Type I diabetes,'" Diabetes (1995) pp. 658-664, vol. 44.

Hussain et al., "Both variant forms of interferon-alpha4 gene (IFNA4a and IFNA4b) are present . . . " J. interferon Cytokine Res. (1997) pp. 559-566, vol. 17.

Isenberg and Leckle, "Biological treatments for systemic lupus erythematosus," Scand. J. Rheumatol (2002) pp. 187-191, vol. 31.

Kawade and Watanabe, "The nature of neutralization reaction between effector protein and monoclonal antibody . . . ," Immunology (1985) pp. 489-495, vol. 56.

Kirou et al., "Coordinate overexpression of interferon-alpha-induced genes in systemic lupus erythematosus," Arthritis & Rheumatism (2004) pp. 3958-3967, vol. 50.

Kontsek et al., "Enhancement of neutralizing efficacy by combining three monoclonal antibodies to human interferon-alpha," Immunology (1991) pp. 8-11, vol. 73.

Reyes and Klimpel, "Interferon alpha/beta synthesis during acute graft-versus-host disease," Transplantation (1987) pp. 412-416, vol. 43.

Mathian et al. "IFN-alpha induces lethal lupus in young, pre-autoimmune . . . ," J. Immunol. (2004) pp. 2499-22506, vol. 174.

McRae, et al., "Interferon-[alpha] and -[beta] inhibit the in vitro differentiaton of immunocompetent human dendritic cells . . . ," Blood (2000) pp. 210-217, vol. 96.

Meager, "Natural autoantibodies to interferons," J. Interferon Cytokine Res. (1997) pp. S51-S53, vol. 17 Suppl.

Mohty et al., "IFN-alpha skews monocyte differentiation into Toll-like receptor 7-expressing dendritic cells . . . ," J Immunol. (2003) pp. 3385-3393, vol. 171.

Morser et al., "Production and screening of cell hybrids producing a monoclonal antibody to human interferon-alpha," J. Gen. Virol. (1981) pp. 257-265, vol. 53.

Noll et al., "Production and characterization of four monoclonal antibodies specific for human interferon-alpha-1 . . . ," Biomed. Biochim. Acta (1989) pp. 165-167, vol. 48.

Overall and Hertzog, "Functional analysis of interferon-alpha subtypes using monoclonal antbodies . . . ," Mol. Immunol. (1992) pp. 391-399. vol. 29.

Pascual et al., "The central role of dendritic cells and inteferon-alpha in SLE," Curr. Opin. Rheumatol. (2003) pp. 548-556, vol. 15.

Pfister et al., "Chronic overexpression of membrane-bound flt3 ligand by T lymphocyte in severe aplastic anemia," Brit. J Haerrialol. (2000) pp. 211-220, vol. 109.

Preble et al., "Systemic lupus erythematosus: presence in human serum of an unusual acid-labile leukocyte interferon," Science (1982) pp. 429-431, vol. 216.

Ravinovitch, "An update on cytokines in the pathogenesis of insulin-dependent diabetes mellitus," Diabetes/Metab. Rvws. (1998) pp. 129-151, vol. 14.

* cited by examiner

CAGGTCCAACTGCAGCAGCCTGGGGCTGAACTGGTGAAGCCTGGGGCTTCAGTGAAGCTG
 Q   V   Q   L   Q   Q   P   G   A   E   L   V   K   P   G   A   S   V   K   L

TCCTGTAAGGCTTCTGGCTACACCTTCACCAACTACTGGATGCACTGGGTGAAGCAGAGG
 S   C   K   A   S   G   <u>Y   T   F   T   N   Y   W   M   H</u>   W   V   K   Q   R
                         V$_H$1

CCTGGACAAGGCCTTGAGTGGATTGGAGAGATTAATCCTAGCCACGGTCGTACTATCTAC
 P   G   Q   G   L   E   W   I   G   <u>E   I   N   P   S   H   G   R   T   I   Y
                                     V$_H$2

AATGAAAACTTCAAGAGCAAGGCCACACTGACTGTAGACAAATCCTCCATCACAGCCTTC
 N   E   N   F   K   S</u>  K   A   T   L   T   V   D   K   S   S   I   T   A   F

ATGCAACTCAGCAGCCTGACATCTGAGGACTCTGCGGTCTATTTCTGTGCAAGAGGGGGA
 M   Q   L   S   S   L   T   S   E   D   S   A   V   Y   F   C   A   R   <u>G   G

SEQ ID NO:1
CTGGGACCCGCCTGGTTTGCTTACTGGGGCCAAGGGACTCTGGTCACTGTCTCTGCA
 L   G   P   A   W   F   A   Y</u>  W   G   Q   G   T   L   V   T   V   S   A
     V$_H$3                                                  SEQ ID NO:2

FIG. 9

CAAATTGTTCTCACCCAGTCTCCAGCAATCATGTCTGCTTCTCCTGGGGAGAAGGTCACC
 Q   I   V   L   T   Q   S   P   A   I   M   S   A   S   P   G   E   K   V   T

TTGACCTGCAGTGCCGGCTCAAGTGTAGATTCCAGCTATTTGTACTGGTACCAGCAGAAG
 L   T   C   <u>S   A   G   S   S   V   D   S   S   Y   L   Y</u>  W   Y   Q   Q   K
             L1

CCAGGATCCTCCCCCAAACTCTGGATTTATAGCACATCCAACCTGGCTTCTGGAGTCCCT
 P   G   S   S   P   K   L   W   I   Y   <u>S   T   S   N   L   A</u>  S   G   V   P
                                         L2

GCTCGCTTCAGTGGCAGTGGGTCTGGGACCTCTTACTCTCTCACAATCAGCAGCATGGAG
 A   R   F   S   G   S   G   S   G   T   S   Y   S   L   T   I   S   S   M   E

GCTGAAGATGCTGCCTCTTATTTCTGCCATCAGTGGAGTAGTTACCCATTCACGTTCGGC
 A   E   D   A   A   S   Y   F   C   <u>H   Q   W   S   S   Y   P   F   T</u>  F   G
                                     L3

TCGGGGACAAAATTGGAAATAAAACGG  SEQ ID NO:9
 S   G   T   K   L   E   I   K   R  SEQ ID NO:10

FIG. 10

SEQUENCE LISTING

<160> NUMBER OF SEQ ID NOS: 16

<210> SEQ ID NO 1
<211> LENGTH: 357
<212> TYPE: DNA
<213> ORGANISM: Mus musculus
<220> FEATURE:
<221> NAME/KEY: CDS
<222> LOCATION: (1)..(357)

<400> SEQUENCE: 1

| cag | gtc | caa | ctg | cag | cag | cct | ggg | gct | gaa | ctg | gtg | aag | cct | ggg | gct | 48 |
|---|---|---|---|---|---|---|---|---|---|---|---|---|---|---|---|---|
| Gln | Val | Gln | Leu | Gln | Gln | Pro | Gly | Ala | Glu | Leu | Val | Lys | Pro | Gly | Ala | |
| 1 | | | | 5 | | | | | 10 | | | | | 15 | | |

| tca | gtg | aag | ctg | tcc | tgt | aag | gct | tct | ggc | tac | acc | ttc | acc | aac | tac | 96 |
|---|---|---|---|---|---|---|---|---|---|---|---|---|---|---|---|---|
| Ser | Val | Lys | Leu | Ser | Cys | Lys | Ala | Ser | Gly | Tyr | Thr | Phe | Thr | Asn | Tyr | |
| | | | 20 | | | | | 25 | | | | | 30 | | | |

| tgg | atg | cac | tgg | gtg | aag | cag | agg | cct | gga | caa | ggc | ctt | gag | tgg | att | 144 |
|---|---|---|---|---|---|---|---|---|---|---|---|---|---|---|---|---|
| Trp | Met | His | Trp | Val | Lys | Gln | Arg | Pro | Gly | Gln | Gly | Leu | Glu | Trp | Ile | |
| | | 35 | | | | | 40 | | | | | 45 | | | | |

| gga | gag | att | aat | cct | agc | cac | ggt | cgt | act | atc | tac | aat | gaa | aac | ttc | 192 |
|---|---|---|---|---|---|---|---|---|---|---|---|---|---|---|---|---|
| Gly | Glu | Ile | Asn | Pro | Ser | His | Gly | Arg | Thr | Ile | Tyr | Asn | Glu | Asn | Phe | |
| 50 | | | | | 55 | | | | | 60 | | | | | | |

| aag | agc | aag | gcc | aca | ctg | act | gta | gac | aaa | tcc | tcc | atc | aca | gcc | ttc | 240 |
|---|---|---|---|---|---|---|---|---|---|---|---|---|---|---|---|---|
| Lys | Ser | Lys | Ala | Thr | Leu | Thr | Val | Asp | Lys | Ser | Ser | Ile | Thr | Ala | Phe | |
| 65 | | | | 70 | | | | | 75 | | | | | 80 | | |

| atg | caa | ctc | agc | agc | ctg | aca | tct | gag | gac | tct | gcg | gtc | tat | ttc | tgt | 288 |
|---|---|---|---|---|---|---|---|---|---|---|---|---|---|---|---|---|
| Met | Gln | Leu | Ser | Ser | Leu | Thr | Ser | Glu | Asp | Ser | Ala | Val | Tyr | Phe | Cys | |
| | | | | 85 | | | | | 90 | | | | | 95 | | |

| gca | aga | ggg | gga | ctg | gga | ccc | gcc | tgg | ttt | gct | tac | tgg | ggc | caa | ggg | 336 |
|---|---|---|---|---|---|---|---|---|---|---|---|---|---|---|---|---|
| Ala | Arg | Gly | Gly | Leu | Gly | Pro | Ala | Trp | Phe | Ala | Tyr | Trp | Gly | Gln | Gly | |
| | | | 100 | | | | | 105 | | | | | 110 | | | |

| act | ctg | gtc | act | gtc | tct | gca | | | | | | | | | | 357 |
|---|---|---|---|---|---|---|---|---|---|---|---|---|---|---|---|---|
| Thr | Leu | Val | Thr | Val | Ser | Ala | | | | | | | | | | |
| | | | 115 | | | | | | | | | | | | | |

<210> SEQ ID NO 2
<211> LENGTH: 119
<212> TYPE: PRT
<213> ORGANISM: Mus musculus

<400> SEQUENCE: 2

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Glu Ile Asn Pro Ser His Gly Arg Thr Ile Tyr Asn Glu Asn Phe
    50                  55                  60

Lys Ser Lys Ala Thr Leu Thr Val Asp Lys Ser Ser Ile Thr Ala Phe
65                  70                  75                  80

Met Gln Leu Ser Ser Leu Thr Ser Glu Asp Ser Ala Val Tyr Phe Cys
                85                  90                  95

Ala Arg Gly Gly Leu Gly Pro Ala Trp Phe Ala Tyr Trp Gly Gln Gly
            100                 105                 110

Thr Leu Val Thr Val Ser Ala
        115

-continued

<210> SEQ ID NO 3
<211> LENGTH: 27
<212> TYPE: DNA
<213> ORGANISM: Mus musculus

<400> SEQUENCE: 3
tacaccttca ccaactactg gatgcac                                          27

<210> SEQ ID NO 4
<211> LENGTH: 9
<212> TYPE: PRT
<213> ORGANISM: Mus musculus

<400> SEQUENCE: 4

Tyr Thr Phe Thr Asn Tyr Trp Met His
1               5

<210> SEQ ID NO 5
<211> LENGTH: 51
<212> TYPE: DNA
<213> ORGANISM: Mus musculus

<400> SEQUENCE: 5
gagattaatc ctagccacgg tcgtactatc tacaatgaaa acttcaagag c               51

<210> SEQ ID NO 6
<211> LENGTH: 17
<212> TYPE: PRT
<213> ORGANISM: Mus musculus

<400> SEQUENCE: 6

Glu Ile Asn Pro Ser His Gly Arg Thr Ile Tyr Asn Glu Asn Phe Lys
1               5                   10                  15

Ser

<210> SEQ ID NO 7
<211> LENGTH: 30
<212> TYPE: DNA
<213> ORGANISM: Mus musculus

<400> SEQUENCE: 7
gggggactgg gacccgcctg gtttgcttac                                       30

<210> SEQ ID NO 8
<211> LENGTH: 10
<212> TYPE: PRT
<213> ORGANISM: Mus musculus

<400> SEQUENCE: 8

Gly Gly Leu Gly Pro Ala Trp Phe Ala Tyr
1               5                   10

<210> SEQ ID NO 9
<211> LENGTH: 327
<212> TYPE: DNA
<213> ORGANISM: Mus musculus
<220> FEATURE:
<221> NAME/KEY: CDS
<222> LOCATION: (1)..(327)

<400> SEQUENCE: 9 caa att gtt ctc acc cag tct cca gca atc atg tct gct tct cct ggg       48
Gln Ile Val Leu Thr Gln Ser Pro Ala Ile Met Ser Ala Ser Pro Gly
1               5                   10                  15 gag aag gtc acc ttg acc tgc agt gcc ggc tca agt gta gat tcc agc       96

```
tat ttg tac tgg tac cag cag aag cca gga tcc tcc ccc aaa ctc tgg        144
Tyr Leu Tyr Trp Tyr Gln Gln Lys Pro Gly Ser Ser Pro Lys Leu Trp
        35                  40                  45 att tat agc aca tcc aac ctg gct tct gga gtc cct gct cgc ttc agt        192
Ile Tyr Ser Thr Ser Asn Leu Ala Ser Gly Val Pro Ala Arg Phe Ser
    50                  55                  60 ggc agt ggg tct ggg acc tct tac tct ctc aca atc agc agc atg gag        240
Gly Ser Gly Ser Gly Thr Ser Tyr Ser Leu Thr Ile Ser Ser Met Glu
65                  70                  75                  80 gct gaa gat gct gcc tct tat ttc tgc cat cag tgg agt agt tac cca        288
Ala Glu Asp Ala Ala Ser Tyr Phe Cys His Gln Trp Ser Ser Tyr Pro
                85                  90                  95 ttc acg ttc ggc tcg ggg aca aaa ttg gaa ata aaa cgg                    327
Phe Thr Phe Gly Ser Gly Thr Lys Leu Glu Ile Lys Arg
            100                 105
```

`<210>` SEQ ID NO 10
`<211>` LENGTH: 109
`<212>` TYPE: PRT
`<213>` ORGANISM: Mus musculus

`<400>` SEQUENCE: 10

```
Gln Ile Val Leu Thr Gln Ser Pro Ala Ile Met Ser Ala Ser Pro Gly
1               5                   10                  15

Glu Lys Val Thr Leu Thr Cys Ser Ala Gly Ser Ser Val Asp Ser Ser
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Phe Thr Phe Gly Ser Gly Thr Lys Leu Glu Ile Lys Arg
            100                 105
```

`<210>` SEQ ID NO 11
`<211>` LENGTH: 36
`<212>` TYPE: DNA
`<213>` ORGANISM: Mus musculus

`<400>` SEQUENCE: 11 agtgccggct caagtgtaga ttccagctat tgtac                                  36

`<210>` SEQ ID NO 12
`<211>` LENGTH: 12
`<212>` TYPE: PRT
`<213>` ORGANISM: Mus musculus

`<400>` SEQUENCE: 12

```
Ser Ala Gly Ser Ser Val Asp Ser Ser Tyr Leu Tyr
1               5                   10
```

`<210>` SEQ ID NO 13
`<211>` LENGTH: 21
`<212>` TYPE: DNA
`<213>` ORGANISM: Mus musculus

`<400>` SEQUENCE: 13

-continued

```
agcacatcca acctggcttc t                                      21

<210> SEQ ID NO 14
<211> LENGTH: 7
<212> TYPE: PRT
<213> ORGANISM: Mus musculus

<400> SEQUENCE: 14

Ser Thr Ser Asn Leu Ala Ser
1               5

<210> SEQ ID NO 15
<211> LENGTH: 27
<212> TYPE: DNA
<213> ORGANISM: Mus musculus

<400> SEQUENCE: 15
catcagtgga gtagttaccc attcacg                                27

<210> SEQ ID NO 16
<211> LENGTH: 9
<212> TYPE: PRT
<213> ORGANISM: Mus musculus

<400> SEQUENCE: 16

His Gln Trp Ser Ser Tyr Pro Phe Thr
1               5
```

ANTI-INTEFERON ALPHA MONOCLONAL ANTIBODIES AND METHODS FOR USE

This application is a division of U.S. application Ser. No. 11/883,961, filed Aug. 8, 2007, which was a National Stage application of International Application No. PCT/US2006/004643, filed Feb. 9, 2006, which claims the benefit of U.S. Provisional Application No. 60/652,233, filed Feb. 10, 2005, the entire contents of each of which are hereby incorporated herein by reference.

FIELD OF THE INVENTION

The present invention relates to methods and compositions useful to diagnose and treat conditions correlated with an abnormal level of interferon-α (IFNα) expression in a subject.

BACKGROUND OF THE INVENTION

Human interferons (IFNs) are functionally-related cytokines that modulate both innate and adaptive immune responses. They are categorized in two groups, largely on the basis of sequence homology, as Type I and II. Type I IFNs include six types (IFN-α, IFN-β, IFN-ω, IFN-κ, IFN-ε, and IFN-λ). IFN-α, β, ω, and κ act through an identical IFN receptor, IFN-λ associates with a distinct receptor, IFNLR. The receptor for IFN-ε is currently unknown. Type II IFN consists of a single type (IFN-γ) and associates with the receptor IFNGR. While Type I IFNs are strongly induced during viral infections, Type II IFN is induced primarily in response to immune and inflammatory stimuli, and thus IFN-γ is frequently referred to as "immune IFN". The most studied of the numerous Type I IFNs include IFN-α, IFN-β, and IFN-ω. Of these, IFN-α is the most complex, includes at least fifteen distinct protein subtypes exhibiting upwards of 75% sequence homology. Diaz (1995) Semin. Virol. 6:143-149; Weissmann et al. (1986) Prog Nucl Acid Res Mol Biol 33:251; J Interferon Res (1993) 13:443-444; Roberts et al. (1998) J Interferon Cytokine Res 18:805-816. In addition to having structural similarity, the IFN-α genes and their products show functional similarities. For example, they are induced by dsRNA or virus, and can interact with the same receptor, the IFNα/β receptor IFNAR. Mogensen, et al. (1999) J. Interferons and other Regulatory Cytokines, John Wiley & Sons. IFNα also inhibits apoptosis, promotes the survival and differentiation of antigen-activated T helper cells and promotes the maturation of functionally efficient monocyte-derived dendritic cells.

Many types of cells produce IFNα when exposed to viruses and dsRNA. Specialized leukocytes (called interferon-α producing cells ("IPCs") produce IFNα in response to a wider variety of stimuli, e.g., viruses, bacteria and protozoa. Several in vitro studies indicate that the various IFN-α subtypes are produced to different extents by distinct IFN-α-secreting cell lines or in a virus type-specific manner following infection of human peripheral blood mononuclear cells (PBMCs), and that these patterns are often associated with subtype-dependent differences in anti-proliferative, anti-viral, and anti-tumor activities. However, the physiological significance of the individual subtypes and their synergistic or antagonist activities with one another in vivo remains undefined.

IFN-α has been implicated as a mediator of the pathology seen in several autoimmune diseases. Moreover, it can cause autoimmune disease development in patients treated with IFN-α for cancer and viral infections. Increased expression of IFN-α has been observed in the disease-localized tissues of patients with insulin-dependent diabetes mellitus (IDDM or type I diabetes), psoriasis, Crohn's disease, and celiac disease. Over expression of IFN-α has been observed in patients with systemic lupus erythematosus (SLE), IDDM and AIDS. In the case of SLE, which is characterized by an abundance of both autoreactive B and T cells, IFN-α expression is observed in not only tissue lesions but circulating within the blood of afflicted individuals. Furthermore, the IFN-α serum levels tend to correlate with the clinical disease activity index. This is believed to stem from cyclical induction of normally quiescent monocytes into potent antigen-presenting dendritic cells (DCs) as triggered by upregulation of IFN-α production by plasmacytoid DCs (pDCs). Indeed, the present inventors have previously demonstrated via oligonucleotide microarray analysis that SLE can be distinguished by "signatures" of unregulated genes involved in granulopoiesis and IFN induction; these signatures revert to normal upon high-dose infusion of glucocorticoids (U.S. patent application Ser. No. 11/228,586, the content of which is incorporated by reference hereto).

Systemic lupus erythematosus (SLE) is a systemic autoimmune rheumatic disease that is particularly aggressive in children and characterized by flares of high morbidity. Autoimmune diseases such as SLE often act in self-perpetuating cycles of relapse and remission. These cycles are often defined by phases of treatment with generally therapeutic regimens administered to quench the SLE disease cycle. FDA-approved treatment options for SLE include corticosteroids, nonsteroidal immune suppressants, antimalarials, and nonsteroidal anti-inflammatory drugs. These drugs abrogate the integrity of all immune effector responses rather than acting upon those specific to the pathogenesis of SLE. SLE represents an unmet medical need since these treatments are only partially effective with moderate to severe side-effects including bone thinning, weight gain, acne, anemia, sterility, rashes diarrhea, hair loss, and nausea. Furthermore, no new therapeutics for SLE have been approved in 40 years.

SLE has recently been closely linked to unabated IFNα production. Shi et al. (1987) Br. J. Dermatol. 117(2):155-159. IFNα is present at elevated levels in SLE serum (Crow et al. (2004) Curr. Opin. Rheumatol. 16(5):541-547) and plasmacytoid DCs (pDCs), the primary source of IFNα, accumulate in SLE skin. Farkas et al. (2001) Am. J. Pathol. 159(1):237-243. Moreover, it has been observed that some patients treated with IFNα have developed lupus (Okanoue et al. (1996) J. Hepatol. 25(3):283-291; Tothova et al. (2002) Neoplasma 49(2):91-94; and Raanani et al. (2002) Acta Haematol. 107(3):133-144) and that lupus patients that present with IFNα antibodies have been shown to display a milder form of the disease. Von Wussow et al. (1988) Rheumatol. Int. 8(5): 225-230. IFNα may act via the differentiation of monocytes into functional dendritic cells (DCs) which in turn mediates the etiopathogenesis of SLE. Pascual V. et al. (2003) Curr. Opin. Rheumatol. 15(5):548-556. A proposed approach for the treatment of SLE is neutralization of IFNα (see Banchereau et al., PCT/US02/00343, the contents of which is incorporated by reference).

Although monoclonal antibodies (MAbs) that can block human IFN-α bioactivity have been produced, none have been reported to date that can neutralize all fifteen known subtypes, and few can neutralize naturally-derived, IFN-α-containing leukocyte IFN. PBL Biomedical Laboratories offers ten mouse monoclonal antibodies that bind to multiple human IFNα gene subtypes (see the world wide web at interferonsource.com/relativespecificity.html). However, each of the PBL antibodies bind the IFNα protein subtype encoded by human IFNα gene subtype 1 (IFNα protein subtype D) and from up to one to twelve other IFNα subtypes. U.S. Patent Publ. No. 2003/0166228A1 discloses a monoclonal antibody (designated 9F3) that was derived from immunization of mice with leukocyte IFNα (which includes all of the IFNα protein subtypes). The 9F3 MAb binds and neutralizes the anti-viral activity of the proteins encoded by seven human IFNα gene subtypes 1, 2, 4, 5, 8, 10 and 21 (which encode IFNα protein subtypes D, A, 4, G, B2, C and F, respectively), without neutralizing the antiviral activity of human IFN ft. This publication does not disclose whether the 9F3 antibody binds and inactivates the other eight IFNα gene subtypes, nor whether it binds to one or both of IFNα protein subtypes 4a and 4b. The PCT publication suggests using the monoclonal antibodies to treat disorders associated with increased expression of IFNα's, in particular, autoimmune disorders such as insulin-dependent diabetes mellitus and SLE. However, it is not known whether the 9F3 antibody is able to sufficiently neutralize the biological activity of the IFNα protein subtypes found in SLE serum.

Because IFNα is a multi-functional mediator of the immune response and has beneficial antiviral activity, complete inhibition or significant down-regulation of all IFNα subtypes is not an optimal therapeutic approach. Thus, a need exists for agents that will selectively neutralize the IFNα subtypes associated with pathological conditions. This invention satisfies this need and provides related advantages as well.

SUMMARY OF THE INVENTION

The invention provides monoclonal antibodies and derivatives thereof that neutralize specific IFNα subtypes. The antibodies of the invention are useful in the amelioration and treatment of conditions associated with increased expression of IFNα, such as SLE, psoriasis, type I diabetes, AIDS, Graft versus Host Disease and other autoimmune diseases. In one aspect, the invention includes an antibody that selectively neutralizes a bioactivity of at least two interferon alpha ("IFNα") protein subtypes such as subtypes A, 2, B2, C, F, G, H2, I, J1, K, 4a, 4b and WA, but does not significantly neutralize at least one bioactivity of IFNα protein subtype D; wherein the bioactivity is activation of the MxA promoter or antiviral activity. Preferably, the antibody is a monoclonal antibody. In one embodiment, the antibody does not significantly neutralize IFNα protein subtype D nor 1. In one embodiment, the monoclonal antibody is ACO-1 or ACO-2. Preferably, the antibodies of the invention inactivate the ability of serum isolated from systemic lupus erythematosus (SLE) patients to stimulate the differentiation of monocytes into dendritic cells.

In another aspect, the invention provides an antibody, or antigen binding fragment thereof, comprising a heavy chain variable domain and a light chain variable domain, wherein the light chain variable domain comprises the following CDRs, derivatives or portions thereof:

$V_L1$ having the amino acid sequence of SEQ ID NO:12;

$V_L2$ having the amino acid sequence of SEQ ID NO:14; and $V_L3$ having the amino acid sequence of SEQ ID NO:16;

wherein the antibody or antigen binding fragment neutralizes the bioactivity of IFNα protein subtypes A, 2, B2, C, F, G, H2, I, J1, K, 4a, 4b and WA, but does not the bioactivity of IFNα protein subtype D, wherein the bioactivity is activation of the MxA promoter.

In a further aspect, the invention provides an antibody, or antigen binding fragment thereof, comprising a light chain variable domain and a heavy chain variable domain, wherein the heavy chain variable domain comprises the following CDRs, derivatives or portions thereof:

$V_H1$ having the amino acid sequence of SEQ ID NO:4;

$V_H2$ having the amino acid sequence of SEQ ID NO:6; and $V_H3$ having the amino acid sequence of SEQ ID NO:8;

wherein the antibody or antigen binding fragment specifically neutralizes the bioactivity of IFNα protein subtypes A, 2, B2, C, F, G, H2, I, J1, K, 4a, 4b and WA, but does not significantly neutralize the bioactivity of IFNα protein subtype D, wherein the bioactivity is activation of the MxA promoter.

In another embodiment, the invention provides an antibody, or antigen binding fragment thereof, comprising at least one light chain or an antigen binding fragment thereof, comprising the following CDRs, derivatives or portions thereof:

$V_L1$ having the amino acid sequence of SEQ ID NO:12;

$V_L2$ having the amino acid sequence of SEQ ID NO:14; and $V_L3$ having the amino acid sequence of SEQ ID NO:16; and at least one heavy chain or an antigen biding fragment thereof, comprising the following CDRs, derivatives or portions thereof:

$V_H1$ having the amino acid sequence of SEQ ID NO:4;

$V_H2$ having the amino acid sequence of SEQ ID NO:6; and $V_H3$ having the amino acid sequence of SEQ ID NO:8.

In another embodiment, the invention provides an antibody that selectively neutralizes the bioactivity of IFNα protein subtype 4a, but does not significantly neutralize the bioactivity of IFNα protein subtype 4b, wherein the bioactivity is activation of the MxA promoter and/or antiviral activity. Preferably, the antibody selectively neutralizes the bioactivity the IFNα protein subtypes A, 2, B2, C, I, K and 4a, but does not significantly neutralize the bioactivity of IFNα protein subtypes D, F, G, 4b and 1. In one embodiment, the antibody is the monoclonal antibody ACO-3.

The invention also provides an antibody that selectively neutralizes the bioactivity the IFNα protein subtypes A, 2, B2 and C, but does not significantly neutralize the bioactivity of IFNα protein subtypes D, 4b and 1, wherein the bioactivity is activation of the MxA promoter and/or antiviral activity. In one embodiment, the antibody is the monoclonal antibody ACO-4.

In another aspect, the invention provides an antibody that selectively neutralizes the bioactivity the IFNα protein subtypes A, 2, G, H2, K, WA and 1, but does not neutralize the bioactivity of IFNα protein subtypes B2 and D, wherein the bioactivity is activation of the MxA promoter and/or antiviral activity. In one embodiment, the antibody is the monoclonal antibody ACO-5.

In still another aspect, the invention includes a monoclonal antibody that selectively neutralizes the bioactivity the IFNα protein subtypes 2 and C, but does not neutralize the bioactivity of IFNα protein subtypes A, B2, C, D, F and 1, wherein the bioactivity is activation of the MxA promoter. In one embodiment, the antibody is monoclonal antibody ACO-6.

In another aspect, the invention provides an antibody that selectively neutralizes the bioactivity the IFNα protein subtypes A, 2, B2, F, I, 4a, 4b, and 1, but does not neutralize the bioactivity of IFNα protein subtypes C, H2, K and WA, wherein the bioactivity is activation of the MxA promoter. In one embodiment, the antibody is monoclonal antibody ACO-8.

In yet another embodiment, the invention provides an antibody that selectively neutralizes the bioactivity the IFNα protein subtypes A, 2, B2, D, F, I, J1, 4a, 4b, and 1, but does not neutralize the bioactivity of IFNα protein subtypes C, G, 112, K and WA, wherein the bioactivity is activation of the MxA promoter.

The antibodies, derivatives or fragments thereof of the invention can be mouse, rat, human, or from other mammals, or fragments or humanized or chimeric forms thereof. The antibodies of the invention include mouse monoclonal antibodies, e.g., ACO-1, ACO-2, ACO-3, ACO-4, ACO-5, ACO-6 and ACO-8, as well as humanized forms, chimeric forms, or fragments thereof. The invention further provides antibodies that bind to essentially the same IFNα epitope as murine monoclonal antibodies ACO-1, ACO-2, ACO-3, ACO-4, ACO-5, ACO-6 and ACO-8. The invention further provides host cells, hybridomas, compositions, pharmaceutical compostions and kits comprising the antibodies of the invention.

The antibodies, derivatives or fragments thereof of the invention have use in the treatment of diseases or conditions associated with overexpression of IFNα, including but not limited to SLE, psoriasis, AIDS, type I diabetes and autoimmune thyroiditis, and for the production of medicaments to treat such diseases and conditions. The antibodies of the invention can also be used to distinguish or to purify various IFNα subtypes.

In further aspect, the invention provides an isolated nucleic acid comprising a polynucleotide encoding a polypeptide selected from the group consisting of SEQ ID NO:2; SEQ ID NO:4, SEQ ID NO:6, SEQ ID NO:8, SEQ ID NO:10, SEQ ID NO:12, SEQ ID NO:14 and SEQ ID NO:16, or polypeptides having at least 80% sequence thereto. Preferably, the polynucleotide is selected from the group consisting of SEQ ID NO:1, SEQ ID NO:3, SEQ ID NO:5, SEQ ID NO:9. SEQ ID NO:11, SEQ ID NO:13 and SEQ ID NO:15.

In addition, the invention provides a protein or peptide comprising a polypeptide selected from the group consisting of SEQ ID NO:2; SEQ ID NO:4, SEQ ID NO:6, SEQ ID NO:8, SEQ ID NO:10, SEQ ID NO:12, SEQ ID NO:14 and SEQ ID NO:16, or a protein or peptide having at least 80% sequence identity thereto. In another aspect, the invention provides a method of producing a hybridoma cell line, including: immunizing a mammal with a composition that includes recombinant IFNα subtypes A, B2 and F; fusing splenocytes from the immunized mammal to a myeloma cell line to produce hybridomas; and identifying a hybridoma cell line that produces a monoclonal antibody that selectively neutralizes one or more IFNα protein subtypes selected from the group consisting of 2, C, G, I, J1, K, 4a, 4b and WA and 1, but does not selectively neutralize IFNα protein subtype D.

The invention also includes host cells and hybridoma cell lines that produce antibodies having the above-noted specificities, e.g., specific binding to one or more interferon alpha ("IFNα") protein subtypes (A, 2, B2, C, F, G, H2, I, J1, K, 4a, 4b and WA), but does not neutralize the bioactivity of, e.g., IFNα protein subtype D. The antibodies and/or hybridoma cell lines can be combined with a carrier, such as a pharmaceutically acceptable carrier, for use in diagnostic and therapeutic methods. The antibodies are useful to detect specific IFNα subtypes and to diagnose, prognose, treat and/or ameliorate symptoms of IFNα related disorders. Examples of such conditions include, but are not limited to SLE, psoriasis, type I diabetes, Graft versus Host (GVH) Disease, AIDS, autoimmune thyroiditis and other autoimmune disorders. The antibodies of the invention are also useful to neutralize and/or isolate these IFNα subtypes in vitro or in vivo.

BRIEF DESCRIPTION OF THE FIGURES

For a more complete understanding of the features and advantages of the present invention, reference is now made to the detailed description of the invention along with the accompanying figures and in which:

FIG. 9 shows the cDNA and amino acid sequence of the heavy chain from ACO-1. The DNA sequence encoding the $V_H1$, $V_H2$ and $V_H3$ CDRs are shown in italics, while the corresponding amino acid sequences are underlined.

FIG. 10 shows the cDNA and amino acid sequence of the light chain from ACO-1. The DNA sequence encoding the $V_L1$, $V_L2$ and $V_L3$ CDRs are shown in italics, while the corresponding amino acid sequences are underlined.

DETAILED DESCRIPTION OF THE INVENTION

Figure 1:
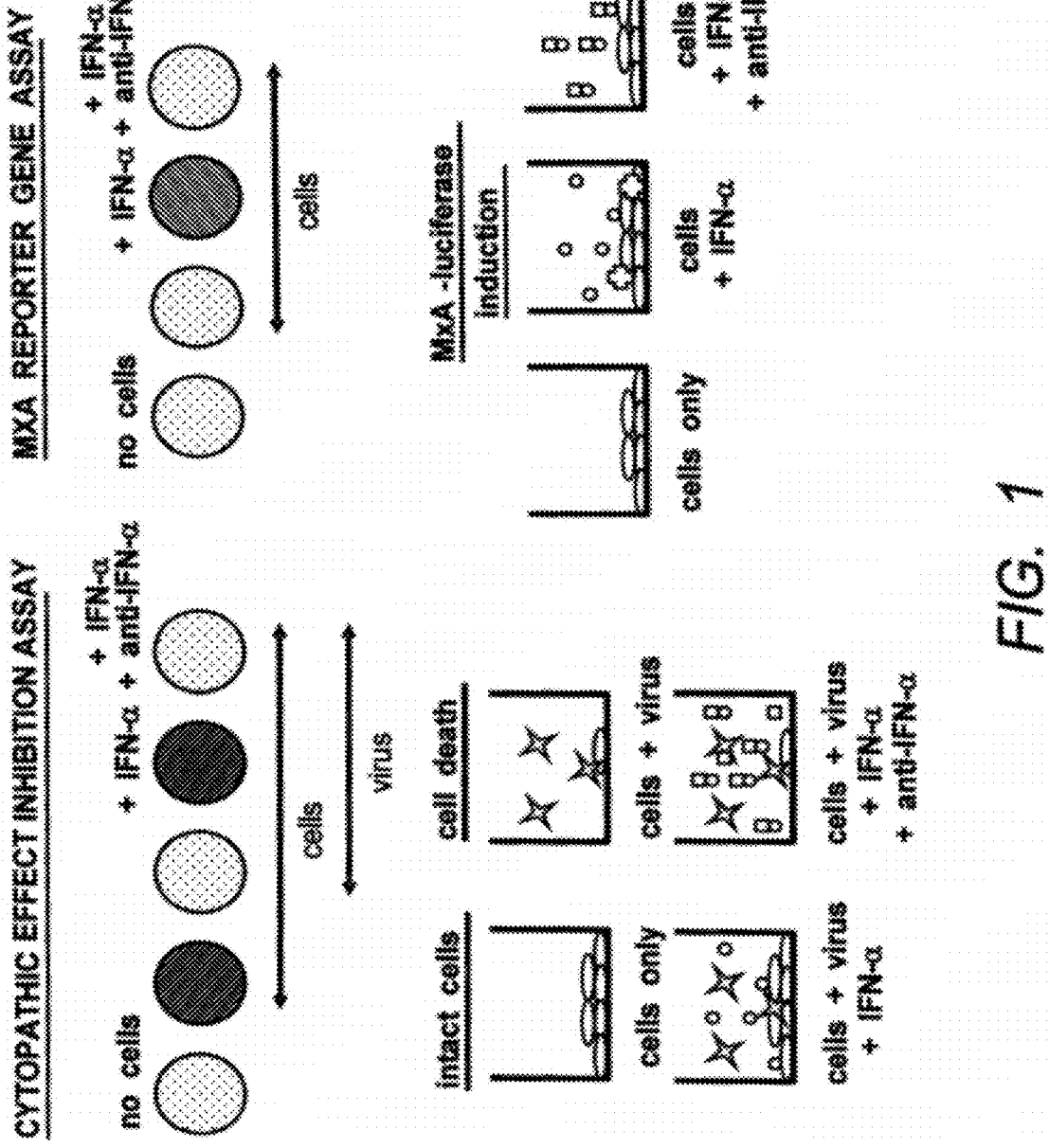
FIG. 1 shows a schematic diagram of the Reporter Gene (RG) assay and the Cytopathic Effect Inhibition Assay (CPE). The filled circles in the CPE assay diagram represent live, intact cells. The unfilled circles represent dead cells, killed by viral infection. The filled circles and cells as well as the "+" in the RG assay diagram represent luciferase expression, while the unfilled circles and cells represent the lack of luciferase expression.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims. For example, the term "a cell" includes a plurality of cells, including mixtures thereof. All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

The term "antibody", as used herein, refers to all classes and subclasses of intact immunoglobulins. The term "antibody" also covers monoclonal antibodies, antibody fragments and antibody fragment clones. "Antibody fragments" include a portion of an intact antibody that contains the antigen binding or variable region of the intact antibody. Examples of antibody fragments include Fab, Fab', F(ab')2, and Fv fragments; single-chain antibody molecules, multispecific antibodies formed from antibody fragments; a Fd fragment includes the VH and CH, domains; a Fv fragment includes the VL and VH domains of a single arm of an antibody, a dAb fragment (Ward et al. (1989) Nature 341:544-546), which includes a VH domain; and an isolated complementarity determining region (CDR). "Single-chain Fv" or "scFv" antibody fragments include the VH and VL domains of antibody, wherein these domains are present in a single polypeptide chain. Generally, the scFv polypeptide further includes a polypeptide linker between the VH and VL domains, which enables the scFv to form the desired structure for antigen binding. For a review of scFv see Pluckthun (1994) in The Pharmacology of Monoclonal Antibodies, vol. 113, Rosenburg and Moore eds., Springer-Verlag, New York, pp. 269-315, Dall'Acqua and Carter (1998) Curr. Opin. Struct. Biol. 8: 443-450, Hudson (1999) Curr. Opin. Immunol. 11: 548-557, Bird et al. (1988) Science 242:423-426 and Huston et al. (1988) Proc. Natl. Acad. Sci. USA 85:5879-5883. Any of the above-noted antibody fragments may be obtained using conventional techniques known to those of skill in the art, and the fragments are screened for binding specificity and neutralization activity in the same manner as are intact antibodies. The antibodies can be isolated from any suitable biological source, e.g., murine, rabbit, rat, human, sheep, canine, etc. "Naturally occurring" or "native" antibodies are heterotetrameric glycoproteins, typically having a molecular weight of approximately 150-200 kD. The heterotetramer includes two identical light (L) chains and two identical heavy (H) chains. Each light chain is covalently bonded to a heavy chain by a disulfide bond.

The term "antibody derivative", as used herein, refers to encompass molecules that bind an epitope and which are modifications or derivatives of a native monoclonal antibody of this invention. Derivatives include, but are not limited to, for example, bispecific, multispecific, heterospecific, trispecific, tetraspecific, multispecific antibodies, chimeric, recombinant and humanized.

The term "antibody variant, as used herein, refers to antibodies produced in a species other than a mouse or an isotype of an antibody selected from the antibodies designated ACO-1 through ACO-6 and ACO-8. The term "antibody variant" also includes antibodies containing post-translational modifications to the linear polypeptide sequence of the antibody or fragment. It further encompasses fully human antibodies.

The term "monoclonal antibody", as used herein, refers to an antibody (including antibody fragments) obtained from a population of substantially homogeneous antibodies, i.e., the individual antibodies in the population are identical except for possible naturally occurring mutations that may be present in minor amounts, which are also part of the present invention so long as they exhibit the desired biological activity. Monoclonal antibodies are highly specific and directed against a single epitope. Monoclonal antibodies may be synthesized by a hybridoma culture, in a bio-reactor, as an ascites or made by recombinant methods, such as in vitro translation, in bacteria, yeast, plants, insect and/or animal cells. Accordingly, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature, 256:495, or may be made by recombinant DNA methods (see, e.g., U.S. Pat. No. 4,816,567). "Monoclonal antibodies" includes, but is not limited to human monoclonal antibodies, humanized monoclonal antibodies, recombinant human antibodies, clones of antigen-recognition and binding-site containing antibody fragments (Fv clones) isolated from phage antibody libraries and derivatives thereof. (See Clackson, et al. (1991) Nature, 352:624-628; and Marks, et al. (1991) J Mol Biol 222:581-597). Monoclonal antibodies also include "chimeric" antibodies (immunoglobulins) in which, e.g., a portion of the heavy and/or light chain is identical with or homologous to corresponding sequences in antibodies derived from a particular species or belonging to a particular antibody class or subclass, while the remainder of the chain(s), or portions thereof, is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison, et al., (1984) Proc Natl Acad Sci USA, 81:6851-6855).

The term "human monoclonal antibody", as used herein, refers to antibodies displaying a single binding specificity that have variable and constant regions derived from human germline immunoglobulin sequences.

The term "human antibody", as used herein, refers to antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, CL, CH domains (e.g., $CH_1$, $CH_2$, $CH_3$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. As described hereinabove, chimeric antibodies may also include any combination of the above. Such changes or variations optionally and preferably retain or reduce the immunogenicity in humans or other species relative to non-modified antibodies. Thus, a human antibody is distinct from a chimeric or humanized antibody. A human antibody may be produced by a non-human animal or prokaryotic or eukaryotic cell that is capable of expressing functionally rearranged human immunoglobulin (e.g., heavy chain and/or light chain) genes. Further, when a human antibody is a single chain antibody, it may also include a linker peptide that is not found in native human antibodies. For example, an Fv fragment may also include a linker peptide, such as two to about eight glycine or other amino acid residues, which connects the variable region of the heavy chain and the variable region of the light chain. Such linker peptides are considered to be of human origin.

A human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., mouse or rat germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

The term "humanized", as used herein, refers to the use of portions of a non-human (e.g., mouse or rat) antibodies that are used on a human immunoglobulin backbone to make chimeric immunoglobulins, immunoglobulin chains or fragments thereof (such as Fv, Fab, Fab', F(ab')2 or other antigen-binding subsequences of antibodies) that have sequences derived from non-human immunoglobulin. Generally, humanized antibodies are human immunoglobulins (recipient antibody) in which residues from part or all of one or more complementarity-determining regions (CDRs) of the recipient antibody are replaced by residues from one or more CDRs of a non-human species (donor antibody) such as mouse, rat or rabbit having the desired specificity, affinity, and capacity. For example, Fv framework region (FR) residues of the human immunoglobulin are replaced by corresponding non-human residues, or vice-versa, that is, human immunoglobulin portions may be grafted onto the non-human immunoglobulin regions that determine antigen specificity. Furthermore, humanized antibodies may include residues that are found neither in the recipient antibody, nor in the imported CDR or framework sequences. The modifications that are not part of the donor or recipient antibody are commonly and easily made to further refine and optimize antibody performance. In general, the humanized antibody will include substantially all of at least one, and typically both, variable domains (light and heavy), in which all or substantially all of the CDR regions correspond to those of a non-human immunoglobulin and all or substantially all of the FR regions are those of a human immunoglobulin sequence. The humanized antibody may also include at least a portion of an immunoglobulin constant region (Fc), typically that of a human immunoglobulin.

The term "recombinant human antibody", as used herein, includes all human antibodies that are prepared, expressed, created or isolated by recombinant method, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a cell transfected to express the antibody (commonly a plasmacytoma), antibodies isolated from a recombinant, combinatorial human antibody library, and antibodies prepared, expressed, created or isolated by any other method that may involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The terms "antigen-binding site" or "binding portion", as used herein, refer to the part of an immunoglobulin molecule that participates in antigen binding. The antigen binding site is formed by amino acid residues of the N-terminal three variable ("V") regions of the heavy ("H") chain and three variable regions of light ("L") chains. Three highly divergent stretches within the V regions of the heavy and light chains are referred to as "hypervariable regions" or "CDRs", of which three are interposed between four conserved flanking stretches known as "framework regions" (FR). Framework regions refer to amino acid sequences that are found naturally between, and adjacent to, hypervariable regions in immunoglobulins. In antibody molecules, the three hypervariable regions of a light chain ($V_L1$, $V_L2$ and $V_L3$) and the three hypervariable regions of a heavy chain ($V_H1$, $V_H2$ and $V_H3$) are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions" or "CDRs."

The term "bioactivity", as used herein, refers to the ability of one or more IFNα subtypes (or IFNβ) to activate the MxA promoter (and interferon-inducible promoter) or to exert an antiviral effect. The $EC_{50}$ and percent neutralization for an antibody of an IFNα bioactivity can vary depending on the assay conditions and the type of IFNα bioactivity measured. For consistency, specific types of bioactivities (i.e., activation of the MA promoter and antiviral activity) and assay conditions (i.e., the "RG assay" and the "CPE assay") are used. The RG assay can be performed using the conditions described herein. Percent neutralization of activation of the $M_xA$ promoter is determined as described in the Examples (see Example 3), using RGmax IFN amounts and 2 micrograms per mL antibody. The antiviral (CPE) assay can be performed according to the methods described in the examples.

The term "bispecific molecule", as used herein, refers to any agent, e.g., a protein, peptide, or protein or peptide complex, which has two different binding specificities. The term "multispecific molecule" or "heterospecific molecule" is intended to include any agent, e.g. a protein, peptide, or protein or peptide complex, which has more than two different binding specificities.

The term "composition", as used herein, refers to a combination of active agent and another carrier, e.g., compound or composition, inert (for example, a detectable agent or label) or active, such as an adjuvant, diluent, binder, stabilizer, buffers, salts, lipophilic solvents, preservative, adjuvant or the like. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, including alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include, e.g., alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myo-inositol. The term carrier further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

The term "control", as used herein, refers to is an alternative subject or sample used in an study for comparison purpose. A control can be "positive" or "negative".

The term "effective amount", as used herein, refers to is an amount sufficient to effect beneficial or desired results. An effective amount can be administered in one or more administrations, applications or dosages.

The terms "epitope" or "antigenic determinant", as used herein, refer to a site on an antigen, or an antigen fragment, recognized by an antibody or an antigen receptor. A T cell epitope is a short peptide derived from a protein antigen that is presented by the appropriate Major Histocompatibility Compatibility (MHC) protein. B-cell epitopes are generally antigenic determinants recognized by B cells and are commonly portions of a three-dimensional surface that are recognized by an antibody, which may include sequential or conformational determinants, as will be known to the skilled artisan.

IgG antibodies can be cleaved into three fragments by papain digestion. Two of these fragments are typically identical antigen-binding fragments, called "Fab" fragments, each with a single antigen-binding site, and a residual "Fc" fragment. The Fab fragment contains the light chain and the amino-terminal half of the heavy chain held together by an interchain disulfide bond. The Fc fragment consists of the carboxyterminal halves of the two heavy chains disulfide-bonded to each other by the residual hinge region. Pepsin digestion of an IgG antibody cleaves in the same general region of the antibody as papain, but on the carboxy-terminal side of the disulfide bond, to produce the F(ab')$_2$ fragment, which has two antigen-combining sites and is still capable of cross-linking antigen. Fab' fragments differ from Fab fragments by the addition of a few residues at the carboxy terminus of the heavy chain CH1 domain including one or more cysteines from the antibody hinge region. Fab'-SH is the designation for Fab' in which the cysteine residue(s) of the constant domains bear a free thiol group.

The term "Fv", as used herein, refers to the minimum antibody fragment that includes a complete antigen-recognition and binding site. In a two-chain Fv species, this region includes a dimer of one heavy- and one light-chain variable domain in non-covalent association. In a single-chain Fv species, one heavy- and one light-chain variable domain may be linked covalently by a flexible peptide linker such that the light and heavy chains can associate in a "dimeric" structure analogous to that in a two-chain Fv species.

The term "heteroantibodies", as used herein, refers to two or more antibodies, antibody binding fragments (e.g., Fab), derivatives thereof, or antigen binding regions linked together that have at least two have different antigen specificities.

The term "Interferon Alpha" ("IFNα"), as used herein, refers to a family of proteins that include some of the main effectors of innate immunity. There are at least 15 known isotypes of human IFNα. The names of the IFNα protein subtypes and corresponding encoding genes are listed below.

| IFNα protein subtype | Corresponding IFNα gene |
|---|---|
| A | 2a |
| 2 | 2b |
| B2 | 8 |
| C | 10 |
| D (Val$^{114}$) | 1 |
| F | 21 |
| G | 5 |
| H2 | 14 |
| I | 17 |
| J1 | 7 |
| K | 6 |
| 4a | 4a |
| 4b | 4b |
| WA | 16 |
| 1 (Ala$^{114}$) | 1 |

See Pestka et al. (1997) "Interferon Standardization and Designations" J Interferon Cytokine Res 17: Supplement 1, S9-S14. IFNα B2 is sometimes also referred to as IFNα B, and is not to be confused with IFNβ. Natural IFNα from leukocytes (leukocyte IFN), as well as these recombinant human IFNα protein subtypes are available from PBL Biomedical Labs, Piscataway, N.J. (interferonsource.com). Natural IFNα is a complex mixture of IFNα subtypes. IFNβ has not been detected in the natural IFNα preparations used herein. Methods for detecting and quantization of these interferons, such as ELISA and RIA are known in the art. See Staehelin et al. (1981) Methods in Enzymology 79 (S. Pestka, ed.) Academic Press, NY 589-595; Kelder et al. (1986) Methods in Enzymology 119 (S. Pestka, ed.) Academic Press, NY 582-587; Stewart (2003) supra; Bennett, et al. (2003) J. Exp. Med. 197(6):711-723; Baechler, et al. (2003) Proc. Natl. Acad. Sci. USA 100(5):2610-2615.

The term "IFNα-producing cell", as used herein, refers to a specialized leukocyte that is responsible for IFNα production which is broadly induced by double stranded RNA (ds) RNA, viruses, bacteria, protozoa, certain cell lines and unmethylated CpG-DNA. Ronnblom and Alm (2004) J. Exp. Med. 194(12):F59-F63.

The phrase "IFNα related condition or disease", as used herein, refers to abnormal and deleterious diseases or preclinical disease states that have been linked with elevated levels of IFNα in a patient's serum. Examples of such include, but are not limited to SLE, Graft versus Host Disease (GVHD), type 1 diabetes, AIDS (caused by human immunodeficiency virus (HIV)), autoimmune thyroiditis, psoriasis and lupus. Methods for determining the level of IFNα are known in the art and described herein.

The term "immune response", as used herein refers to the antigen-specific responses of lymphocytes to foreign substances. Any substance that can elicit an immune response is considered to be "immunogenic" and is referred to as an "immunogen". All immunogens are antigens, however, not all antigens are immunogenic. An immune response can be humoral (via antibody activity) or cell-mediated (via T cell activation).

The terms "immunological binding," and "immunological binding properties", as used herein refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) may be determined by calculation of the concentrations and the actual rates of association and dissociation as are well known in the art. The ratio of $K_{off}/K_{on}$ enables cancellation of all parameters not related to affinity, and is thus equal to the dissociation constant $K_d$. See, e.g., Coligan, et al., CURRENT PROTOCOLS IN IMMUNOLOGY, Wiley, NY (1999).

The term "isolated", as used herein, refers to an antibody that has been identified and separated and/or recovered from a component of its natural environment. Contaminant components of its natural environment are materials that may interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody may be prepared by at least one purification step. Monoclonal antibodies and variants and derivatives thereof are considered isolated antibodies.

The term "isotype", as used herein, refers to the antibody class based on the amino acid sequence of the constant domain of their heavy chains. There are five major isotypes of immunoglobulins: IgA, IgD, IgE, IgG, and IgM, and several of these can be further divided into subclasses, e.g., IgG1, IgG2, IgG3, IgG4, IgA1, and IgA2.

"Lupus" refers to several diseases or disorders. "Systemic lupus erythematosus" (SLE) is the form of the disease that can affect many parts of the body. The symptoms of SLE may be mild or serious, and are reviewed herein. "Discoid lupus erythematosus" is a chronic skin disorder in which a red, raised rash appears on the face, scalp, or elsewhere. The raised areas may become thick and scaly and may cause scarring. The rash may last for days or years and may recur. A small percentage of people with discoid lupus have or develop SLE later. "Subacute cutaneous lupus erythematosus" refers to skin lesions that appear on parts of the body exposed to sun. "Drug-induced lupus" is a form of lupus caused by certain medications. Symptoms are similar to those of SLE (arthritis, rash, fever, and chest pain) and they typically go away completely when the drug is stopped. The kidneys and brain are rarely involved. "Neonatal lupus" is a rare disease that can occur in newborn babies of women with SLE, Sjögren's syndrome, or no disease at all, and may be caused by autoantibodies in the mother's blood called anti-Ro (SSA) and anti-La (SSB). At birth, the babies typically have a skin rash, liver problems, and low blood counts.

The term "pharmaceutically acceptable carrier", as used herein, refers to encompasses any of the standard pharmaceutical carriers, e.g., a phosphate buffered saline solution, water, and emulsions, such as an oil/water or water/oil emulsion, and various types of wetting agents. The compositions may also include stabilizers and preservatives and any of the above noted carriers with the additional provisio that they be acceptable for use in vivo. For examples of carriers, stabilizers and adjuvants, see Martin REMINGTON'S PHARM. SCI., 18th Ed., Mack Publ. Co., Easton, Pa. (1995), and in the "PHYSICIAN'S DESK REFERENCE", 58th ed., Medical Economics, Montvale, N.J. (2004).

The terms, "selectively neutralizes" and "selectively neutralizing", as used herein, refer to an isolated and purified antibody (such as, but not limited to a monoclonal antibody) that neutralizes selectively at least 40% of a bioactivity of one or more "IFNα" protein subtypes, but does not significantly neutralize at least one bioactivity of another IFNα protein subtype, wherein the bioactivity is activation of the MxA promoter or antiviral activity. Since the different subtypes of IFNα vary in function, it is advantageous to selectively neutralize specific forms of IFNα to control specific functions. The one or more antibodies of the present invention are specific for IFNα, but are also "selective" for one or more subtypes and not others. In order to selectively neutralize one or more IFNα protein subtypes, e.g., A, 2, B2, C, F, G, H2, I, J1, K, 4a, 4b, one or more antigenic epitopes on IFNα that do not significantly cross-react with antigenic epitopes on, e.g., the D subtype, have been identified, isolated, characterized and purified, as disclosed herein.

The phrase "does not significantly neutralize", as used herein, refers to an antibody that neutralizes less than 40% of the bioactivity of a specified IFNα subtype (or of IFNβ), wherein the bioactivity is measured by the MxA reporter gene assay (RG assay) or cytopathic effect assay (CPE assay) in accordance with the conditions described herein. In some embodiments, an antibody of the invention does not significantly neutralize more than 35%, 30%, 25%, 20%, 15%, 10%, 5%, 2% or even not more than 1% of the bioactivity of the specified IFNα subtype.

The term "subject", as used herein, refers to a vertebrate, preferably a mammal, more preferably a human. Mammals include, but are not limited to, rodents, simians, humans, farm animals, horses, dogs and cats.

Current SLE treatments are symptomatic and induce global immunosuppression; these include glucocorticoids, cyclophosphamide, azathioprine and mycophenolate mofetil. Their efficacy is only partial, and undesirable side-effects such as increased susceptibility to infections are common. Specifically neutralizing IFN-α in SLE patients is thus an attractive concept for controlling the disease pathology. Since massively unregulated production of IFN-α by pDCs plays a significant role in perpetuating the disease cycle, neutralizing IFN-α bioactivity using specific MAb blockade provides a targeted therapeutic agent that does not compromise the ability of patients to mount effective immune responses to pathogens. A desirable MAb candidate against IFN-α would require specific characteristics, including: (i) ability to react against most or all of the human IFN-α subtypes involved in the etiology of SLE; (ii) ability to block the biological activities of such IFN-α subtypes, (iii) inability to block either IFN-β or the IFNAR; and/or (iv) high affinity. Neutralizing IFN-α rather than the IFNAR may also provide a safer and more specific therapeutic since this approach would not affect the antiviral effects of the IFN-β signaling pathway, which uses the same receptor as IFN-α. To this end, the invention also provides a series of monoclonal antibodies (MAbs) capable of neutralizing human IFN-α. For example, two of these anti-IFN-α MAbs are capable of blocking the bioactivity of thirteen recombinant IFN-α subtypes as well as two complex mixtures of IFN produced upon viral infection. In one aspect, the invention provides seven MAbs that variably neutralize human IFN-α, of which three significantly neutralize up to thirteen recombinant IFN-α subtypes and complex IFN-α mixtures (both commercially-available leukocyte IFN and supernatants produced upon infection of PBMCs with flu virus). Two of the MAbs, ACO-1 and ACO-2, also consistently block the bioactivity of serum from SLE patients that exhibit IFN-α signatures by microarray analysis. Since ACO-1 and ACO-2 do not significantly neutralize the bioactivity of IFNα protein subytpes D and 1, but do neutralize the IFNα bioactivity of SLE serum, these subtypes are unlikely to be involved significantly in the etiology of SLE. Accordingly, it is desirable to treat SLE using antibodies, such as humanized or non-antigenic (e.g., deimmunized) variants of ACO-1 and ACO-2, which block the bioactivity of IFNα subtypes associated with SLE, but do not block the bioactivities of IFNα protein subytpes (D and 1) that are not significantly associated with SLE.

The invention also provides an antibody that selectively neutralizes a bioactivity of at least two interferon alpha ("IFNα") protein subtypes selected from the group consisting of protein subtypes A, 2, B2, C, F, G, H2, I, J1, K, 4a, 4b and WA, but does not significantly neutralize at least one bioactivity of IFNα protein subtype D; wherein the bioactivity is, e.g., activation of the MxA promoter and/or antiviral activity. In another aspect, the invention provides a method for treating a disease or condition associated with abnormal expression of at least one interferon alpha ("IFNα") protein subtype selected from protein subtypes A, 2, B2, C, F, G, H2, I, J1, K, 4a, 4b and WA without neutralizing IFNα protein subtype D antiviral activity, in a subject, including administering to the subject an effective amount of one or more of the antibodies described herein. Examples of such antibodies include, but are not limited to, the antibodies designated ACO-1, ACO-2, ACO-3, ACO-4, ACO-5, ACO-6 and antibodies that recognize essentially the same IFNα epitope as any of the foregoing antibodies. Preferably, the antibodies are monoclonal antibodies. The ATCC deposit numbers of hybridoma cell lines that produce these monoclonal antibodies are listed hereinbelow. Accordingly, the invention further provides hybridoma cell lines expressing the ACO-1, ACO-2, ACO-3, ACO-4, ACO-5, ACO-6, and ACO-8 antibodies.

In one aspect, the invention provides an antibody that binds essentially the same IFNα epitope as an antibody selected from the group consisting of ACO-1, ACO-2, ACO-3, ACO-4, ACO-5 and ACO-6. The invention further provides cell lines, e.g., a hybridoma, which expresses such antibodies.

In another embodiment, the invention provides an antibody that neutralizes a bioactivity of at least 3, 4, 5, 6, 7, 8, 9, 10, 11, 12, 13 or 14 IFNα protein subtypes selected from protein subtypes A, 2, B2, C, F, G, H2, I, J1, K, 4a, 4b and WA, but does not neutralize at least one bioactivity of IFNα protein subtype D; wherein the bioactivity is activation of the MxA promoter or antiviral activity. The invention further provides hybridoma cell lines expressing such antibodies.

Monoclonal antibodies are provided that do not neutralize at least one bioactivity of IFNα protein subtype 1, wherein the bioactivity is activation of the MxA promoter and/or antiviral activity.

In another aspect, the invention provides a monoclonal antibody that selectively neutralizes a bioactivity the IFNα protein subtypes A, 2, B2, C, F, G, H2, I, K, 4a, 4b and WA, but does not significantly neutralize the bioactivity of IFNα protein subtypes D and 1, wherein the bioactivity is activation of the MxA promoter and/or antiviral activity. Other embodiments include ACO-1 and ACO-2.

In still another aspect, the invention provides a monoclonal antibody that selectively neutralizes the bioactivity the IFNα protein subtypes A, 2, B2, C, I, K and 4a, but does not significantly neutralize the bioactivity of IFNα protein subtypes D, F, G, 4b and 1; wherein the bioactivity is activation of the MxA promoter and/or antiviral activity. One such embodiment is the ACO-3 antibody made by the ACO-3 cell and derivatives thereof.

In further aspect, the invention provides an antibody that selectively neutralizes the bioactivity the IFNα protein subtypes A, 2, B2, and C, but does not significantly neutralize the bioactivity of IFNα protein subtypes D, 4b, and 1, wherein the bioactivity is activation of the MxA promoter and/or antiviral activity. One such embodiment is the ACO-4 antibody and derivatives thereof made by the ACO-4 cell and derivatives thereof.

In another aspect, the antibody of this invention selectively neutralizes a bioactivity IFNα 4a, but does not selectively neutralize IFNα 4b, wherein the bioactivity is activation of the MxA promoter. Examples of these antibodies are the antibodies designated ACO-3 and ACO-4, and derivatives thereof, made by, e.g., the ACO-3 and ACO-4 cells and derivatives thereof, respectively.

In yet another aspect, the invention provides a monoclonal antibody that selectively neutralizes the bioactivity the IFNα protein subtypes A, 2, G, I, K, WA and 1, but does not significantly neutralize the bioactivity of IFNα protein subtypes B2 and D, wherein the bioactivity is activation of the MxA promoter and/or antiviral activity. One such embodiment is the ACO-5 antibody and derivatives thereof, made by, e.g., the ACO-5 cell and derivatives thereof.

In an additional embodiment, the invention provides a monoclonal antibody that selectively neutralizes the bioactivity the IFNα protein subtypes 2 and C, but does not neutralize the bioactivity of IFNα protein subtypes A, B2, C, D, F and 1, wherein the bioactivity is activation of the MxA promoter. An example is the ACO-6 antibody and derivatives thereof made by the ACO-6 cell and derivatives thereof.

In still another aspect, the invention provides a monoclonal antibody that selectively neutralizes the bioactivity the IFNα protein subtypes A, 2, B2, D, F, I, 4a, 4b, and 1, but does not significantly neutralize the bioactivity of IFNα protein subtypes C, H2, K and WA, wherein the bioactivity is activation of the MxA promoter. An example is the ACO-8 antibody and derivatives thereof made by the ACO-8 cell and derivatives thereof.

The monoclonal antibodies of the invention also include a humanized antibody, a human antibody, a chimeric antibody, an antibody fragment, such as an Fab fragment, an F(ab')2 fragment, an Fab' fragment or any other fragment(s) known to the skilled artisan. In one example, the antibody is a humanized chimeric antibody.

In yet another embodiment, the invention provides a method of producing a hybridoma cell line by, for example, immunizing a mammal with a composition including recombinant IFNα subtypes A, B2 and F; fusing splenocytes from the mammal to a myeloma cell line to produce hybridomas; and identifying a hybridoma cell line that produces a monoclonal antibody that selectively neutralizes one or more IFNα protein subtypes selected from the group consisting of 2, C, G, I, J1, K, 4a, 4b and WA and 1, but does not selectively neutralize IFNα protein subtype D.

The term "neutralizes", as used herein, refers to the ability of an antibody to inhibit one or more biological activities of an IFNα protein subtype by at least 40% as measured by the RG, CPE or monocyte differentiation assays defined herein. For example, the antibody neutralizes at least 50%, 60%, 70%, 75%, 80%, 85%, 90%, 95%, 97%, 98%, 99% or 100% of a biological activity of an IFNα protein subtype. IFNα biological activities include transcriptional activation of the MxA promoter (see, e.g., "RG" assay, infra), antiviral activity (e.g., cytopathic effect assay ("CPE"), and the ability of SLE serum to cause differentiation of monocytes into dendritic cells. Methods for determining the % neutralization using RG assay and the CPE assay are described herein.

The phrases "does not neutralize" or "does not significantly neutralize", as used herein, refers to an antibody neutralizes less than 40% of a biological activity of an IFNα protein subtype, wherein the neutralizing effect of added antibody as measured by the RG, CPE or monocyte differentiation assay. For example, the antibody neutralizes less than 35%, or less than 35%, or less than 30%, or less than 25%, or less than 20%, or less than 15%, or less than 10%, or less than 8%, or less than 5%, or less than 3%, or even less than 1% of the bioactivity.

The antibody of the invention may be antibody variants, derivatives or fragments. In one aspect, the antibodies are isolated. In another aspect, the antibodies are combined with a suitable carrier. The antibodies can be isolated from any species, mouse, rat, simian, or recombinantly produced. Examples of mouse monoclonal antibodies are the antibodies designated ACO-1, ACO-2, ACO-3, ACO-4, ACO-5, ACO-6 and ACO-8. Also provided by this invention are the hybridoma cell lines that produce these monoclonal antibodies, alone in combination with a carrier or in culture.

Also provided by this invention are polypeptides that include an antibody, variant, derivative or fragment thereof, including but not limited to immunoglobulin chains and CDRs. The polypeptides preferably bind, inhibit and/or neutralize IFNα as described above, with the same or similar affinity and/or ability.

The present invention further provides an anti-idiotypic antibody reactive with any of the antibodies ACO-1 through ACO-6 or ACO-8. An anti-idiotype antibody is an antibody made against the unique determinants of a single antibody. Anti-idiotype antibodies are useful for detecting bound antibodies in immunoassays and other applications. An anti-idiotype antibody of the invention can include or be derived from any mammal, such as but not limited to a human, a mouse, a rabbit, a rat, a rodent, a primate, and the like.

One or more of the above antibodies can be further combined with a carrier, a pharmaceutically acceptable carrier or medical device that is suitable for use of the antibody or related composition in diagnostic or therapeutic methods. The carrier can be a liquid phase carrier or solid phase carrier, e.g., bead, gel or carrier molecule such as a liposome. The composition can optionally further include at least one further compound, protein or composition. An additional example of "carriers" includes therapeutically active agents such as another peptide or protein (e.g., an Fab' fragment, a J-chain, another antibody, a toxin and the like). For example, an anti-IFNα antibody of this invention, variant, derivative or fragment thereof can be functionally linked (e.g., by chemical coupling, genetic fusion, noncovalent association or otherwise) to one or more other molecular entities, such as another antibody (e.g., to produce a bispecific or a multispecific antibody), a cytotoxin, a cellular ligand or an antigen. Accordingly, this invention encompasses a large variety of antibody conjugates, bi- and multispecific molecules, and fusion proteins, whether or not they target the same epitope as the antibodies of this invention.

Additional examples of carriers are organic molecules (also termed modifying agents) or activating agents that may be attached covalently, directly or indirectly, to an antibody of this invention. Attachment of the molecule can improve pharmacokinetic properties (e.g., increased in vivo serum half-life). Examples of organic molecules include, but are not limited to a hydrophilic polymeric group, a fatty acid group or a fatty acid ester group. The term "fatty acid", as used herein, refers to, e.g., mono-carboxylic acids and di-carboxylic acids. The term "hydrophilic polymeric group", as used herein, refers to an organic polymer that is, e.g., more soluble in water than in octane.

Hydrophilic polymers suitable for modifying antibodies of the invention can be linear or branched and include, for example, polyalkane glycols (e.g., polyethylene glycol (PEG), monomethoxy-polyethylene glycol (mPEG), polypropylene glycol (PPG) and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. A suitable hydrophilic polymer for use with the antibody of the invention may have a molecular weight of, e.g., about 800 to about 150,000 Daltons as a separate molecular entity. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer including an amine group can be coupled to a carboxylate of the fatty acid or fatty acid ester, and an activated carboxylate (e.g., activated with N, N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Examples of such include, but are not limited to, n-dodecanoate, n-tetradecanoate, n-octadecanoate, n-eicosanoate, n-docosanoate, n-triacontanoate, n-tetracontanoate, cis-δ-9-octadecanoate, all cis-δ-5,8,11, 14-eicosatetraenoate, octanedioic acid, tetradecanedioic acid, octadecanedioic acid, docosanedioic acid, and the like. Suitable fatty acid esters include mono-esters of dicarboxylic acids that include a linear or branched lower alkyl group. The lower alkyl group can include from one to about twelve, preferably one to about six, carbon atoms.

In yet another aspect, the present invention provides a transgenic nonhuman animal, such as a transgenic mouse (also referred to herein as a "Human MAb mouse"), which expresses a fully human monoclonal antibody that neutralizes at least one IFNα protein subtype similar to an antibody of this invention as defined above. In a particular embodiment, the transgenic nonhuman animal is a transgenic mouse having a genome including a human heavy chain transgene and a human light chain transgene encoding all or a portion of an anti-alpha V antibody of the invention. To generate human antibodies, the transgenic nonhuman animal can be immunized with a purified or enriched preparation of IFNα protein subtypes A, B and F. An example of a transgenic nonhuman animal may be, e.g., a transgenic mouse that is capable of producing multiple isotypes of human monoclonal antibodies to IFNα (e.g., IgG, IgA and/or IgM) by undergoing V-D-J recombination and isotype switching. Isotype switching may occur by, e.g., classical or non-classical isotype switching.

Accordingly, in another embodiment, the invention provides isolated cells derived or isolated from a transgenic nonhuman animal as described above, e.g., a transgenic mouse, which express human antibodies. The isolated B-cells can then be immortalized by fusion to an immortalized cell to provide a source (e.g., a hybridoma) of human antibodies. These hybridomas are also included within the scope of the invention.

The present invention further provides at least one antibody method or composition, for diagnosing at least one IFNα related condition in a cell, tissue, organ, animal or patient and/or, prior to, subsequent to, or during a related condition, as known in the art and/or as described herein. They are also used to prognose or monitor disease progression.

Also provided is a composition comprising at least one anti-IFNα antibody of this invention, variant, derivative or fragment thereof, suitable for administration in an effective amount to modulate or ameliorate IFNα-associated symptoms or treat at least one IFNα related condition in a cell, tissue, organ, animal or patient and/or, prior to, subsequent to, or during a related condition, as known in the art and/or as described herein. The compositions include, for example, pharmaceutical and diagnostic compositions/kits, including a pharmaceutically acceptable carrier and at least one anti-IFNα antibody of this invention, variant, derivative or fragment thereof. As noted above, the composition can further include additional antibodies or therapeutic agents which in combination, provide multiple therapies tailored to provide the maximum therapeutic benefit.

Alternatively, a composition of this invention can be co-administered with other therapeutic and cytotoxic agents, whether or not linked to them or administered in the same dosing. They can be coadministered simultaneously with such agents (e.g., in a single composition or separately) or can be administered before or after administration of such agents. Such agents can include corticosteroids, nonsteroidal immune suppressants, antimalarials, and nonsteroidal anti-inflammatory drugs. The compositions can be combined with alternative therapies such as administration of corticosteroids, nonsteroidal immune suppressants, antimalarials, and nonsteroidal anti-inflammatory drugs.

In another aspect, the invention provides methods for selectively neutralizing a bioactivity of at least two interferon alpha ("IFNα") protein subtypes selected from the group consisting of protein subtypes A, 2, B2, C, F, G, H2, I, J1, K, 4a, 4b and WA, without selectively neutralizing at least one bioactivity of IFNα protein subtype D; wherein the bioactivity is activation of the MxA promoter or antiviral activity. The method requires contacting the sample suspected of containing the subtype with a monoclonal antibody that selectively neutralizes the subtype. Examples of such antibodies include, but are not limited to the antibodies designated ACO-1, ACO-2, ACO-3, ACO-4, ACO-5 and ACO-6.

Various therapies are provided by this invention. For example, this specification discloses methods for ameliorating the symptoms associated with abnormal expression of at least one interferon alpha ("IFNα") protein subtype selected from the group consisting of protein subtypes A, 2, B2, C, F, G, H2, I, K, 4a, 4b and WA without binding IFNα protein subtypes D and 1 in a subject, by administering to the subject an effective amount of an antibody that selectively neutralizes the subtype. Examples of such are provided above.

The invention provides methods for treating a disease or condition which results in abnormal expression of at least one interferon alpha ("IFNα") protein subtype selected from the group consisting of protein subtypes A, 2, B2, C, F, G, H2, I, K, 4a, 4b and WA without binding IFNα protein subtypes D and 1 in a subject, by administering to the subject an effective amount of an antibody that selectively neutralizes the subtype. Examples of such are provided above. Further provided are methods of immunization by administering to a mammal a composition including recombinant IFNα subtypes A, B2 and F. In another embodiment, the immunization method includes administering to a mammal a composition consisting essentially of IFNα subtypes A, B2 and F, a pharmaceutically acceptable carrier, and optionally, one or more adjuvants. In an alternative aspect, immunization raises antibodies that neutralize IFNα protein subtypes A, B2 and F, but not IFNα protein subtypes D and 1. In a further aspect, the method and composition neutralizes IFNα 4a and not IFNα 4b (e.g., ACO-3).

For use in vivo, the antibodies and compositions of this invention are administered or delivered to patients (e.g., human subjects) at therapeutically effective dosages to neutralize selected IFNα subtypes. Additionally, administration or delivery of effective amounts of antibodies or compositions of this invention can be use to treat or ameliorate the symptoms of an IFNα related condition such as SLE, diabetes, psoriasis or AIDS, in a subject using any suitable route of administration for antibody-based clinical products. Many are known in the art, such as injection or infusion.

Dosages Forms. A dosage unit for use of the antibodies of the present invention may be a single compound or mixtures thereof with other compounds. The compounds may be mixed together, form ionic or even covalent bonds. One or more of the antibodies of the present invention may be administered in oral, intravenous (bolus or infusion), intraperitoneal, subcutaneous, or intramuscular form, all using dosage forms well known to those of ordinary skill in the pharmaceutical arts. Depending on the particular location or method of delivery, different dosage forms, e.g., tablets, capsules, pills, powders, granules, elixirs, tinctures, suspensions, syrups, and emulsions may be used to provide the antibody(ies) of the present invention to a patient in need of therapy that includes the neutralization of certain IFNα subtypes, as described herein. The antibodies are generally hydrophobic but they may be administered as any one of known salt forms.

Antibodies are typically administered in admixture with suitable pharmaceutical salts, buffers, diluents, extenders, excipients and/or carriers (collectively referred to herein as a pharmaceutically acceptable carrier or carrier materials) selected based on the intended form of administration and as consistent with conventional pharmaceutical practices. Depending on the best location for administration, the antibodies may be formulated to provide, e.g., maximum and/or consistent dosing for the particular form for oral, rectal, topical, intravenous injection or parenteral administration. While the antibodies, e.g., humanized forms of ACO-1, ACO-2, ACO-3, ACO-4, ACO-5, ACO-6 and ACO-8, may be administered alone, or in combination, in a pharmaceutically acceptable carrier. The carrier may be solid or liquid, depending on the type and/or location of administration selected.

Techniques and compositions for making useful dosage forms using the present invention are described in one or more of the following references: Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.), and the like, relevant portions incorporated herein by reference.

The antibodies of the present invention may be administered in the form of liposome delivery systems, e.g., small unilamellar vesicles, large unilamallar vesicles, and multilamellar vesicles, whether charged or uncharged. Liposomes may include one or more: phospholipids (e.g., cholesterol), stearylamine and/or phosphatidylcholines, mixtures thereof, and the like.

The antibodies may also be coupled to one or more soluble, biodegradable, bioacceptable polymers as drug carriers or as a prodrug. Such polymers may include: polyvinylpyrrolidone, pyran copolymer, polyhydroxylpropylmethacrylamide-phenol, polyhydroxyethylasparta-midephenol, or polyethyleneoxide-polylysine substituted with palmitoyl residues, mixtures thereof, and the like. Furthermore, the antibodies may be coupled one or more biodegradable polymers to achieve controlled release of the antibodies, biodegradable polymers for use with the present invention include: polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels, mixtures thereof, and the like.

For direct delivery to the nasal passages, sinuses, mouth, throat, esophogous, tachea, lungs and alveoli, the antibodies may also be delivered as an intranasal form via use of a suitable intranasal vehicle. For dermal and transdermal delivery, the antibodies may be delivered using lotions, creams, oils, elixirs, serums, transdermal skin patches and the like, as are well known to those of ordinary skill in that art. Parenteral and intravenous forms may also include pharmaceutically acceptable salts and/or minerals and other materials to make them compatible with the type of injection or delivery system chosen, e.g., a buffered, isotonic solution. Examples of useful pharmaceutical dosage forms for administration of antibodies may include the following forms.

Injectable solution. A parenteral composition suitable for administration by injection is prepared by stirring 1.5% by weight of active ingredient in deionized water and mixed with, e.g., up to 10% by volume propylene glycol and water. The solution is made isotonic with sodium chloride and sterilized using, e.g., ultrafiltration. Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle that has a basic dispersion medium. In the case of sterile powders for the preparation of sterile injectable solutions, useful methods for the preparation of a dry-powder include, vacuum-drying, spray-freezing, vacuum drying in the presence of heat, and freeze-drying techniques, which yield a powder of the active ingredient plus any additional desired ingredient from a previously sterile-filtered solution thereof. The antibodies of the present invention may be delivered as micro or nanoparticles in an injectable form or via pulmonary or other delivery.

Suspensions. In one embodiment, an aqueous suspension may be prepared for administration so that each 5 ml has, e.g., 0.001-1,000 mg of finely divided active ingredient, 200 mg of sodium carboxymethyl cellulose, 5 mg of sodium benzoate, 1.0 g of sorbitol solution, and saline to 0.01, 0.1, 1, 5 or 10 ml.

The effective dose of antibody may include amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Formulations including an antibody of this invention are provided herein. The formulations of the present invention can be prepared by a process that includes mixing at least one antibody of this invention and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing of the antibody and preservative in an aqueous diluent is carried out using conventional dissolution and mixing procedures. For example, a measured amount of at least one antibody in buffered solution is combined with the desired preservative in a buffered solution in quantities sufficient to provide the antibody and preservative at the desired concentrations. Variations of this process would be recognized by one of ordinary skill in the art, e.g., the order the components are added, whether additional additives are used, the temperature and pH at which the formulation is prepared, are all factors that can be optimized for the concentration and method of administration used.

The formulation may include one or more preservative or stabilizer such as phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative(s), or preservatives such as, e.g., 0.1-2% m-cresol (e.g., 0.2, 0.3. 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, and 1.0%).

The compositions and formulations can be provided to patients as clear solutions or as dual vials including a vial of lyophilized antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available. Recognized devices including these single vial systems include those pen-injector devices for delivery of a solution such as BD™ Autejector device, Humaject™ NovoPen™ device, BD™ Pen device, AutoPen™ device, OptiPen™ device, GenotropinPen™ device, Genotronorm Pen™ device, Humatro Pen™ device, Reco-Pen™ device, Roferon Pen™ device, Biojector™ device, Iject™ device, J-tip Needle-Free Injector™ device, Intraject™ device, Medi Jector™ device, e.g., as made or developed by Becton, Dickinson and Company (Franklin Lakes, N.J., available at bd.com), Disetronic™ Licensing AG (Roche Diabetes Care AG, Burgdorf, Switzerland, available at disetronic.com); Bioject Medical Technologies, Inc, (Portland, Oreg., available at bioject.com); National Medical Products (Irvine, Calif.), Weston Medical (Peterborough, UK, available at weston-medical.com), Medi-Ject Corp (Minneapolis, Minn., available at mediject.com).

The invention provides an article of manufacture, including packaging material and at least one vial including a solution of at least antibody as of this invention with the prescribed buffers and/or preservatives, optionally in an aqueous diluent, wherein the packaging material includes a label that indicates that such solution can be held over a period of 1, 2, 3, 4, 5, 6, 9, 12, 18, 20, 24, 30, 36, 40, 48, 54, 60, 66, 72 hours or greater. The invention further includes an article of manufacture, including packaging material, a first vial including at least one lyophilized antibody of this invention and a second vial including an aqueous diluent of prescribed buffer or preservative, wherein the packaging material includes a label that instructs a patient to reconstitute the antibody in the aqueous diluent to form a solution that can be held over a period of twenty-four hours or greater.

Kits. The present invention also includes pharmaceutical kits useful, for example, for the treatment of a disease conditions, the kit may include one or more containers that include the pharmaceutical composition that may be provided as is, diluted or resuspended into a therapeutically effective amount of antibodies. Such kits may further include, if desired, one or more of various conventional pharmaceutical kit components, such as, for example, containers with one or more pharmaceutically acceptable carriers, liquids, additional containers, etc., as will be readily apparent to those skilled in the art. Printed instructions, either as inserts or as labels, indicating quantities of the components to be administered, guidelines for administration, and/or guidelines for mixing the components, may also be included in the kit. It should be understood that although the specified materials and conditions are important in practicing the invention, unspecified materials and conditions are not excluded so long as they do not prevent the benefits of the invention from being realized.

Antibodies. The antibodies of this invention include monoclonal antibodies. They also can be IFNα-neutralizing functional fragments, antibody derivatives or antibody variants. They can be chimeric, humanized, or totally human. A functional fragment of an antibody includes, but is not limited to, Fab, Fab', Fab$_2$, Fab'$_2$, and single chain variable regions. Antibodies can be produced in cell culture, e.g., in bacteria, yeast, plants or plant cells, insects or insect cells, eukaryotic cell, or in various animals, including but not limited to cows, rabbits, goats, mice, rats, hamsters, guinea pigs, sheep, dogs, cats, monkeys, chimpanzees, apes, etc. So long as the fragment or derivative retains specificity of binding or neutralization ability as the antibodies of this invention it can be used. Antibodies can be tested for specificity of binding by comparing binding to appropriate antigen to binding to irrelevant antigen or antigen mixture under a given set of conditions. If the antibody binds to the appropriate antigen at least 2, 5, 7, and even 10 times more than to irrelevant antigen or antigen mixture then it is considered to be specific. Specific assays, e.g., ELISA, for determining specificity are described infra.

The antibodies also are characterized by their ability to neutralize one or more biological activity of an IFNα protein subtype, such as, but not limited to, transcriptional activation of the MxA promoter or of another promoter that is inducible by IFNα, antiviral activity, ability of SLE serum to cause differentiation of monocytes into dendritic cells.

The monoclonal antibodies of the invention can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U397, MLA 144, ACT IV, MOLT4, DA-1, JURKAT, WEHI, K-562, COS, RAJI, NIH 3T3, HL-60, MLA 144, NAMAIWA, NEURO 2A, CHO, PerC.6, YB2/O) or the like, or heteromyelomas, fusion products thereof, or any cell or fusion cell derived therefrom, or any other suitable cell line as known in the art (see, e.g., www.atcc.org, www.lifetech.com., and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, preferably the spleen or lymph nodes, of humans or other suitable animals that have been immunized with the antigen of interest.

Any other suitable host cell can also be used for expressing-heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from various commercial vendors such as Cambridge Antibody Technologies (Cambridgeshire, UK), MorphoSys (Martinsreid/Planegg, Del.), Biovation (Aberdeen, Scotland, UK), BioInvent (Lund, Sweden), and Antitope (Cambridge, UK) using methods known in the art. See U.S. Pat. No. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1977) Microbiol. Immunol. 41:901-907 (1997); Sandhu et al. (1996) Crit. Rev. Biotechnol. 16:95-118; Eren et al. (1998) Immunol. 93:154-161 that are capable of producing a repertoire of human antibodies, as known in the art and/or as described herein. Such techniques, include, but are not limited to, ribosome display (Hanes et al. (1997) Proc. Natl. Acad. Sci. USA, 94:4937-4942; Hanes et al., (1998) Proc. Natl. Acad. Sci. USA, 95:14130-14135); single cell antibody producing technologies (e.g., selected lymphocyte antibody method ("SLAM") (U.S. Pat. No. 5,627,052, Wen et al. (1987) J. Immunol. 17:887-892; Babcook et al., Prod. Natl. Acad. Sci. USA (1996) 93:7843-7848); gel microdroplet and flow cytometry (Powell et al. (1990) Biotechnol. 8:333-337; One Cell Systems, (Cambridge, Mass.); Gray et al. (1995) J. Imm. Meth. 182:155-163; Kenny et al. (1995) Bio/Technol. 13:787-790); B-cell selection (Steenbakkers et al. (1994) Molec. Biol. Reports 19:125-134 (1994).

Antibody variants of the present invention can also be prepared using delivering a polynucleotide encoding an antibody of this invention to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

The term "antibody variant", as used herein, refers to post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fc-mediated cellular toxicity, and glycoproteins so generated.

Antibody variants also can be prepared by delivering a polynucleotide of this invention to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbiol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al., Adv. Exp. Med. Biol. (1999) 464:127-147 and references cited therein. Antibody variants have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and reference cited therein. Thus, antibodies of the present invention can also be produced using transgenic plants, according to know methods.

Antibody derivatives can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids. In general, the CDR residues are directly and most substantially involved in influencing antigen binding.

Monoclonal antibodies produced in mice (or in other non-human animals) carry the risk in therapy that humans can develop antibodies to the animal MAb. The human antibodies can then reduce the effectiveness of the animal Mab and can also result in an allergic reaction. This problem can be avoided by constructing antibodies that are not recognized as foreign. Methods for constructing such antibodies are know in the art, and are often based on grafting the CDR region of the animal MAb onto an immunoglobulin backbone of a target host. The most common method is humanization, which can be accomplished by grafting the CDRs of an animal antibody onto the framework of a human immunoglobulin. In some cases, a few amino acid residues from framework of the animal antibody are retained to preserve the integrity of the antigen binding site.

Humanization or engineering of antibodies of the present invention can be performed using any known method, such as but not limited to those described in U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; and 4,816,567. Methods for antibody humanization based on computer modeling and variable regions are known to those of skill in the art. See, for example, Tsurushita et al. (2005) Humanized Antibodies and their Applications 36(1):69-83; the contents of which are incorporated by reference.

In one humanization method, rather than grafting the entire animal CDRs onto a human framework, only the specificity determining residues (SDRs) (the most critical residues of the CDR for the antibody-ligand binding) are grafted onto the human framework (Kashmiri et al. (2005) Humanized Antibodies and their Applications 36(1):25-34; the contents of which are incorporated by reference). In an alternative approach to humanization, human framework sequences from the set of human germline genes are chosen based on the structural similarity of the human CDR to those of the animal CDR to be humanized (Hwang et al. (2005) Humanized Antibodies and their Applications 36(1):35-42; the contents of which are incorporated by reference).

Framework shuffling is another approach to humanization that allows for the identification of human framework combinations that will support the functional features of mouse or other animal CDRs, without the need for rational design or structural information. In this method, combinatorial Fab libraries are created by in-frame fusion of the CDRs of an animal MAb to pools of corresponding human frameworks that include all known heavy and light chain human germline genes. The Fab libraries may then be screened for antigen binding. The light and heavy chains of the parental Mab may be successively humanized in a further selection process. See Dall'Acqua et al. (2005) Humanized Antibodies and their Applications 36(1):43-60; the contents of which are incorporated by reference.

In an alternative approach, which has been successfully used to make at least one FDA approved antibody for use in humans, guided selection can be used to make a serial transition from rodent to human versions of rodent antibodies through the use of a panel of human antibodies with similar characteristics to the starting rodent antibody, and phage or ribosome display. See Osbourn et al. (2005) Humanized Antibodies and their Applications 36(1):61-68; the contents of which are incorporated by reference. In this approach, the panel of human antibodies or V regions are screened for binding of an antigen of interest. The resulting antibody is entirely of human origin.

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice that are producing a desirable antibody can be fused to make hybridoma cell lines for continuous production of the desired antibody. (See for example, Russel et al. (2000) Infection and Immunity April 2000:1820-1826; Gallo et al. (2000) European J. of Immun. 30:534-540; Green (1999) J. of Immun. Methods 231:11-23; Yang et al. (1999) J. of Leukocyte Biology 66:401-410; Yang (1999) Cancer Research 59(6):1236-1243; Jakobovits (1998) Advanced Drug Delivery Reviews 31:33-42; Green, L. and Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold (1997) Genetic Engineering News 17(14); Mendez et al. (1997) Nature Genetics 15:146-156; Jakobovits (1996) WEIR'S HANDBOOK OF EXPERIMENTAL IMMUNOLOGY, THE INTEGRATED IMMUNE SYSTEM Vol. IV, 194.1-194.7; Jakobovits (1995) Current Opinion in Biotechnology 6:561-566; Mendez et al. (1995) Genomics 26:294-307; Jakobovits (1994) Current Biology 4(8):761-763; Arbones et al. (1994) Immunity 1(4):247-260; Jakobovits (1993) Nature 362(6417):255-258; Jakobovits et al. (1993) Proc. Natl. Acad. Sci. USA 90(6):2551-2555; U.S. Pat. No. 6,075,181.)

Human monoclonal antibodies can also be produced by a hybridoma which includes a B cell obtained from a transgenic nonhuman animal, e.g., a transgenic mouse, having a genome including a human heavy chain transgene and a light chain transgene fused to an immortalized cell. The antibodies of this invention also can be modified to create chimeric antibodies. Chimeric antibodies are those in which the various domains of the antibodies' heavy and light chains are coded for by DNA from more than one species. See, e.g., U.S. Pat. No. 4,816,567.

Any recombinant antibody or the antibody fragment thereof according to the present invention may be used, so long as it can react specifically with at least two interferon alpha ("IFNα") protein subtypes selected from the group consisting of protein subtypes A, 2, B2, C, F, G, H2, I, J1, K, 4a, 4b and WA, but does not neutralize at least one bioactivity of IFNα protein subtype D. The antibody may also neutralize the IFNα, as measured in known bioassays, e.g., the bioactivity is activation of the MxA promoter or antiviral activity. One such antibody is an antibody that reacts specifically with one or more IFNα subtypes A, 2, B2, C, F, G, H2, I, J1, K, 4a, 4b and WA, but not subtype D, and includes CDRs, derivatives or portions thereof selected from:

$V_H1$ having the amino acid sequence of SEQ ID NO:4;
$V_H2$ having the amino acid sequence of SEQ ID NO:6;
$V_H3$ having the amino acid sequence of SEQ ID NO:8.
$V_L1$ having the amino acid sequence of SEQ ID NO:12;
$V_L2$ having the amino acid sequence of SEQ ID NO:14;
$V_L3$ having the amino acid sequence of SEQ ID NO:16;
derivatives and combinations thereof.

The antibodies may also include antibodies and/or antibody fragments in which one or more amino acids are deleted, added, substituted and/or inserted in these amino acid sequences and which specifically react with IFNα subtypes A, 2, B2, C, F, G, H2, I, J1, K, 4a, 4b and WA are also included within the scope of the present invention.

In the present invention, one or more amino acid deletions, substitutions, insertions or additions in the amino acid sequence refers to modifications and/or mutations of one or more amino acids that are deleted, substituted, inserted and/or added at one or more positions in the backbone of an immunoglobulin. The one or more deletions, substitutions, insertions and/or additions may be caused in the same amino acid sequence simultaneously. Also, the amino acid residue substituted, inserted or added can be natural or non-natural. Examples of the natural amino acid residue include L-alanine, L-asparagine, L-aspartic acid, L-glutanine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine, L-cysteine, and the like.

Examples of amino acid residues that may be substituted may be found within one or more of the following groups, for example:

Group A: leucine, isoleucine, norleucine, valine, norvaline, alanine, 2-aminobutanoic acid, methionine, O-methylserine, t-butylglycine, t-butylalanine, cyclohexylalanine;

Group B: aspartic acid, glutamic acid, isoaspartic acid, isoglutamic acid, 2-aminoadipic acid, 2-aminosuberic acid;

Group C: asparagine, glutamine;

Group D: lysine, arginine, ornithine, 2,4-diaminobutanoic acid, 2,3-diaminopropionic acid;

Group E: proline, 3-hydroxyproline, 4-hydroxyproline;

Group F: serine, threonine, homoserine; and

Group G: phenylalanine, tyrosine.

The term "antibody derivative" further includes "linear antibodies". The procedure for making linear antibodies is known in the art and described in Zapata, et al. (1995) Protein Eng. 8(10):1057-1062. Briefly, linear antibodies include a pair of tandem Fd segments ($V_H$-$C_H$1-VH-$C_H$1) which form a pair of antigen binding regions. Linear antibodies can be bispecific or monospecific.

The antibodies of this invention can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present invention include naturally purified products, products of chemical synthetic procedures, and products produced by recombinant techniques from a eukaryotic host, including, for example, yeast, higher plant, insect and mammalian cells, or alternatively from a prokaryotic cells as described above.

In some aspects of this invention, it will be useful to detectably or therapeutically label the antibody. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample. Antibodies can also be conjugated, for example, to a pharmaceutical agent, such as chemotherapeutic drug or a toxin. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionucleotides, such as iodine-131 ($^{131}$I), yttrium-90 ($^{90}$Y), bismuth-212 ($^{212}$Bi), bismuth-213 ($^{213}$Bi), technetium-99m ($^{99m}$Tc), rhenium-186 ($^{186}$Re), and rhenium-188 ($^{188}$Re); antibiotics, such as doxorubicin, adriamycin, daunorubicin, methotrexate, daunomycin, neocarzinostatin, and carboplatin; bacterial, plant, and other toxins, such as diphtheria toxin, pseudomonas exotoxin A, staphylococcal enterotoxin A, abrin-A toxin, ricin A (deglycosylated ricin A and native ricin A), TGF-alpha toxin, cytotoxin from Chinese cobra (naja naja atra), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

With respect to preparations containing antibodies covalently linked to organic molecules, they can be prepared using suitable methods, such as by reaction with one or more modifying agents. Examples of such include modifying and activating groups. A "modifying agent" as the term is used herein, refers to a suitable organic group (e.g., hydrophilic polymer, a fatty acid, a fatty acid ester) that includes an activating group. Specific examples of these are provided supra. An "activating group" is a chemical moiety or functional group that can, under appropriate conditions, react with a second chemical group thereby forming a covalent bond between the modifying agent and the second chemical group. Examples of such are electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson (1996) BIOCONJUGATE TECHNIQUES, Academic Press: San Diego, Calif.). An activating group can be bonded directly to the organic group (e.g., hydrophilic polymer, fatty acid, fatty acid ester), or through a linker moiety, for example a divalent $C_1$-$C_{12}$ group wherein one or more carbon atoms can be replaced by a heteroatom such as oxygen, nitrogen or sulfur. Suitable linker moieties include, for example, tetraethylene glycol. Modifying agents that include a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl)carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid.

The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments including an organic moiety that is bonded to specific sites of an antibody of the present invention can be prepared using suitable methods, such as reverse proteolysis. See generally, Hermanson (1996) BIOCONJUGATE TECHNIQUES, Academic Press: San Diego, Calif. (1996).

Preparation and Isolation of Proteins and Polypeptides. Polypeptides and proteins are necessary components of various methods of this invention. For example, recombinant antibodies, variants, derivatives and fragments thereof can be obtained by chemical synthesis using a commercially available automated peptide synthesizer such as those manufactured by Perkin Elmer/Applied Biosystems, Inc., Model 430A or 431A, Foster City, Calif., USA. The synthesized protein or polypeptide can be precipitated and further purified, for example by high performance liquid chromatography (HPLC). Alternatively, the proteins and polypeptides can be obtained by known recombinant methods as described herein using the host cell and vector systems described above. They can also be prepared by enzymatic digestion or cleavage of naturally occurring proteins.

Proteins and peptides can be isolated or purified by standard methods including chromatography (e.g., ion exchange, affinity, and sizing column chromatography), centrifugation, differential solubility, or by any other standard technique for protein purification. Alternatively, affinity tags such as hexa-His (Invitrogen), Maltose binding domain (New England Biolabs), influenza coat sequence (Kolodziej, et al., (1991) Methods Enzymol. 194:508-509), and glutathione-S-transferase can be attached to the peptides of the invention to allow easy purification by passage over an appropriate affinity column. Isolated peptides can also be physically characterized using such techniques as proteolysis, nuclear magnetic resonance, and x-ray crystallography.

It is well known that modifications can be made to any peptide to provide it with altered properties. Peptides for use in this invention can be modified to include unnatural amino acids. Thus, the peptides may include D-amino acids, a combination of D- and L-amino acids, and various "designer" amino acids (e.g., β-methyl amino acids, C-β-methyl amino acids, and N-α-methyl amino acids, etc.) to convey special properties to peptides.

In a further embodiment, subunits of peptides that confer useful chemical and structural properties will be chosen. For example, peptides including D-amino acids may be resistant to L-amino acid-specific proteases in vivo. Modified compounds with D-amino acids may be synthesized with the amino acids aligned in reverse order to produce the peptides of the invention as retro-inverso peptides. In addition, the present invention envisions preparing peptides that have better defined structural properties, and the use of peptidomimetics, and peptidomimetic bonds, such as ester bonds, to prepare peptides with novel properties. In another embodiment, a peptide may be generated that incorporates a reduced peptide bond, i.e., R1-CH$_2$NH—R2, where R1, and R2 are amino acid residues or sequences. A reduced peptide bond may be introduced as a dipeptide subunit. Such a molecule would be resistant to peptide bond hydrolysis, e.g., protease activity. Such molecules would provide peptides with unique function and activity, such as extended half-lives in vivo due to resistance to metabolic breakdown, or protease activity. Furthermore, it is well known that in certain systems constrained peptides show enhanced functional activity (Hruby (1982) Life Sciences 31:189-199 and Hruby et al. (1990) Biochem J. 268:249-262); the present invention provides a method to produce a constrained peptide that incorporates random sequences at all other positions.

Assays for IFNα Biological Activity. Differentiation of Monocytes. The generation of activated T and B lymphocytes requires the recruitment and maturation of antigen presenting cells ("APCs"). These APCs include B cells, monocytes/macrophages and dendritic cells. The serum of SLE patients contains IFNα which can activate DCs and the activated activity can blocked with polyclonal or monoclonal antibody preparations. Methods to detect and quantitate this activity are described in the scientific and patent literature (e.g., see paragraphs 0136 through 0150 of patent publication number U.S. 2004/0067232 A1), relevant portions incorporated herein by reference.

Activation of the MxA promoter. The ability of IFNα to activate the MxA promoter, and the ability of the anti-IFNα monoclonal antibodies of the invention to block this activation can be measured using reporter gene assays where the MxA promoter is fused to a reporter gene, such as chloramphenicol acetyltransferase (CAT) or luciferase (luc), preferably luciferase. Assays for CAT and luciferase are known to those of skill in the art. Preferably, the activity of the MxA promoter is measured in A549 cells stably transformed with an MxA promoter/reporter gene fusion construct. A549 cells are a lung carcinoma cell line available through the ATCC (product number CCl-185). The MxA (a.k.a. Mx1) promoter can be human, mouse or rat. The sequence and structure of the human MxA promoter is disclosed in Genbank Accession number X55639, Chang et al. (1991) Arch Virol. 117:1-15; and Ronni et al. (1998) J Interferon Cytokine Res. 18:773-781. Human MxA promoter/luciferase fusion constructs and luciferase assays are disclosed in U.S. patent application 20040209800 and Rosmorduc et al. (1999) J of Gen Virol 80:1253-1262. Human MxA promoter/CAT fusion constructs and CAT assays are disclosed in Fernandez et al. (2003) J Gen Virol 84:2073-2082 and Fray et al. (2001) J Immunol Methods 249:235-244. The mouse MxA (Mx1) promoter is disclosed in Genbank accession number M21104; Hug et al. (1988) Mol Cell Biol 8:3065-3079; and Lleonart et al. (1990) Biotechnology 8:1263-1267. A mouse MxA promoter/luciferase fusion construct and a luciferase assay are disclosed in Canosi et al. (1996) J Immunol Methods 199:69-67.

EXAMPLES

Materials and Methods

Sources of human IFN-α. Recombinant IFN-α subtype proteins were obtained from PBL Biomedical Laboratories (PBL). The subtypes and specific activities determined by the manufacturer included: IFN-α A (3.8×10$^8$ U/mg); IFN-α 2 (2.77×10$^8$ U/mg); IFN-α B2 (4.63×10$^8$ U/mg); IFN-α C (2.31×10$^8$ U/mg); IFN-α D (7.5×10$^7$ U/mg); IFN-α F (3.6× 10$^8$ U/mg); IFN-α G (2.33×10$^8$ U/mg); IFN-α H2 (1.05×10$^8$ U/mg); IFN-α I (1.4×10$^8$ U/mg); IFN-α J1 (2.6×10$^8$ U/mg); IFN-α K (1.48×10$^8$ U/mg); IFN-α 1 (1.4×10$^8$ U/mg); IFN-α 4a (2.12×10$^8$ U/mg); IFN-α 4b (1.8×10$^8$ U/mg); IFN-α WA (2.4×10$^8$ U/mg); and IFN-β (8.23×10$^7$ U/mg). Leukocyte IFN, was purchased from Sigma (1-2396, Lot #111K1603).

PBMC-flu supernatant (PBMC-flu), which contains a complex mixture of human IFNα subtypes, was prepared in-house by infection of human PBMCs from buffy coats with Influenza A/PR/8/34 (H1N1) (Charles River Laboratories, Lot #4×PRO11022) at a viral titer of 1 HAU/pDC. Specifically, PBMCs (peripheral blood monocytic cells) were harvested from a human buffy coat by centrifuging over Ficoll and collecting the PBMC-containing interface. FACS staining/analysis was performed to confirm the presence of plasmacytoid DCs and determine their percentage within the PBMCs and stained with fluorescence-conjugated antibodies specific for Lin, CD3, CD14, CD16, CD19, CD56, CD123, HLA-DR, and CD11c (BD Pharmingen). pDCs were characterized as CD14 negative, CD11c negative and CD123 positive. The flu virus stock (Specific Pathogen-Free Avian Supply; Influenza A/PR/8/34 (H1N1) (Cat. #490710; Lot #4XPR011022), Final HA titer per 0.05 mL: 1:16,777,216; Charles River Laboratories, Connecticut, USA) was diluted to 1000 HAU/μl (hemagglutinin units per microliter) in RPMI media (RPMI+10% FCS+L-glutamine). The volume of diluted virus required was based on the proportion of pDCs in the purified PBMCs, so that there is at least 1 HAU/pDC (i.e., each well should contain 1×10$^6$ PBMCs, and if you have 0.3% pDCs, each well will contain 3000 pDCs. In that case, 4-5 μL of virus at 1000 HAU/μL will be added to each well).

PBMCs prepared from the buffy coat were centrifuged at 900 rpm for 10 min and resuspended at 5,000 cells/4 (this will provide for 1×10$^6$ cells per well in a volume of 200 μL) in RPMI+10% FCS+L-glutamine). The cells plus flu virus were plated in 96-well U-bottom plates, and incubated at 37° C.+5% CO$_2$ for 24 h. Following incubation for 24 h, the cells formed a pellet at the bottom of the wells and have formed clusters. The supernatant was harvested from the wells by careful pipetting, avoiding cell pellets at the bottom of the wells. Combined supernatants were centrifuged in 50 mL conical tubes at 900 rpm for 10 min to pellet any residual cells and other culture debris. PBMC-flu supernatants, containing a complex mixture of IFNα, were pooled, mixed, and stored at −80° C. in 0.5 ml aliquots until use.

Cytopathic Effect (CPE) Inhibition Assay. CPE Materials: Dulbecco's Modified Eagle's Medium (DMEM) "complete": DMEM with phenol red+10% FCS+2 mM L-glutamine+ penicillin+streptomycin+β-2-mercaptoethanol (β-me), 96-well flat-bottom tissue culture plates, A549 cells (ATCC CCL-185); these cells are cultured in Ham's F12K medium+ 10% FCS+2 mM L-glutamine+penicillin+streptomycin+ 500-800 μg G418, 1×PBS, 1× trypsin, "Intron A" (IFNα-2b, Schering-Plough) controls, test samples (SLE serum, recombinant IFNα subtypes) with/without hybridoma supernatant or purchased polyclonal/monoclonal antibody preparations, EMC virus stocks (prepared from the murine encephalomyocarditis virus (EMCV) adapted to tissue culture on Vero cell monolayers; the ATCC product number for this viral stock is VR-129B, and the product number for Vero cells is CCL-81).

Crystal violet stock solution: 1.25 mg NaCl+3.75 mg crystal violet+775 mL formaldehyde/ethanol solution (which is prepared with 75 mL formaldehyde, 750 mL 95% ethanol, and 1500 mL distilled water) were stirred for 20 min, then filtered through a 0.45 micron filter and stored for not longer than 3 months. A working solution of Crystal violet was prepared by diluting the stock solution 1:10 with the formaldehyde/ethanol solution. The crystal violet solutions were stored at room temperature.

CPE Methods. A schematic diagram of the Cytopathic Effect Inhibition Assay (CPE) is shown in FIG. 1. CPE assays were performed in triplicate wells in 96-well flat-bottom plates. For each assay type, it was useful to incorporate positive control wells containing intron A (Schering-Plough) samples of varying concentrations and negative control wells containing only cells+media. Adherent A549 cells were harvested from flasks by removing the culture media, washing once with PBS, and trypsinization. Trypsinization was stopped by adding DMEM "complete" to the flask. The tyrpsinized cells were collected from the flask, centrifuged, resuspended and counted. Their concentration was adjusted to 600,000 cells/mL in complete DMEM. The volume of the wells for the assay was 150 µL (prior to virus addition) and 200 µL (following virus addition). 50 µL of the volume was cells, of which 15,000 cells (50 µl of the 300,000/mL cell suspension) was added per well.

To assay for viral inhibition by recombinant IFNα. 100 µL of various concentrations of IFNα solution (in DMEM complete) was added in triplicate wells. 50 µL of cells was added and incubated for 5 hours at 37° C.+5% $CO_2$. After this time period, 50 µL of EMC virus diluted 50-fold from stock was added and incubation continued for 48 h at 37° C.+5% $CO_2$.

To assay for viral inhibition by SLE serum. 50 µL (e.g., no dilution) or 25 µL (e.g., 2× dilution) of SLE serum was placed in triplicate wells. The volume was adjusted to 100 µL by adding DMEM without FCS (note: any time serum samples of any type are added to wells using this assay, DMEM without FCS was used) and then 50 µL of cells was added and incubated for 4 h at 37° C.+5% $CO_2$. After this time period, 50 µL of EMC virus diluted 50-fold from stock (this concentration was determined, for our preparation, as the minimal amount of stock able to kill all cells in 48 hours) was added and incubation continued for 48 h at 37° C.+5% $CO_2$.

To assay for viral inhibition by PBMC-flu supernatants. 50 µL (e.g., no dilution) or serial dilutions of PBMC-flu supernatant was added in triplicate wells. The volume of each well was adjusted to 100 µL by adding DMEM with FCS, and then 50 µL of cells was added and incubated for 4 h at 37° C.+5% $CO_2$. After this time period, 50 µL of EMC virus diluted 50-fold from stock was added and incubation continued for 48 h at 37° C.+5% $CO_2$.

To assay for antibody-mediated blockade of viral inhibition by recombinant IFNα, SLE serum, or PBMC-flu supernatants using commercially-available Abs, mouse serum, or fusion supernatants, 50 µL of either: (i) DMEM without FCS containing commercial polyclonal or monoclonal Ab preparations; (ii) 50 µL of mouse serum; or (iii) 50 µL of hybridoma supernatant was added to bring the total volume of each well at this point to 100 pt. The plates were incubated for 1.5 to 2 h at 37° C.+5% $CO_2$. 50 µL of cells was added to each well and incubated for 5 h at 37° C.+5% $CO_2$. After this time period, 50 µL of EMC virus diluted 50-fold from stock was added and incubation was continued for 48 h at 37° C.+5% $CO_2$.

After 48 hour incubation period in the above CPE assays, all media was carefully removed from the wells using a multichannel pipet. 50 µL of crystal violet was added and allowed to stain for 4-6 min. The crystal violet was carefully removed and 200 µL of distilled water was added and immediately removed. The plates were allowed to dry for at least 30 min, and then read on an ELISA plate reader at an OD of 570 nm.

To obtain the percentage of blockade (based upon the ability of the included control antibody or antibody contained in the hybridoma supernatants to inhibit IFNα-mediated protection against cell death), the data was normalized in the context of the "negative control" (IFNα recombinant, SLE serum, or PBMC-flu supernatant+cells+virus) being 100% viability (0% cell death) and the "positive control" (cells+virus only) being 0% viability (100% cell death) using the Prism® 4.0 for Macintosh, Version 4.0A software (GraphPad Software, Inc., San Diego, Calif.) and the Normalize algorithm to adjust all of the values to percentages according to the controls.

Reporter Gene (RG) Assay. RG Materials. Dulbecco's Modified Eagle's Medium (DMEM), no phenol red or supplements; Dulbecco's Modified Eagle's Medium (DMEM) "complete": DMEM with phenol red+10% FCS+2 mM L-glutamine+penicillin+streptomycin+2-me (β-me); Dulbecco's Modified Eagles Medium (DMEM) prepared to contain everything listed above except FCS; ViewPlate-96, white, tissue culture-treated (PerkinElmer Life Sciences); 93D7 cells (A549 transfected to express luciferase driven by the type I IFN-inducible MxA promoter); these cells are cultured in Ham's F12K medium+10% FCS+2 mM L-glutamine+penicillin+streptomycin+500-800 µg G418; 1×PBS; 1× trypsin; "intron A" (IFNα 2b, Schering-Plough) controls; test samples (SLE serum, recombinant IFNα subtypes) with/without hybridoma supernatant or purchased polyclonal/monoclonal antibody preparations; Britelite™ luminescence reporter gene assay kit (PerkinElmer Life Sciences).

RG Methods. A luciferase-based reporter gene assay was utilized to evaluate the ability of the anti-IFNα MAbs to neutralize the bioactivity of recombinant IFNα subtypes, leukocyte IFN and PBMC-flu. A schematic diagram of the RG assay is shown in FIG. 1. The 93D7 cell line, which was derived by stable transfection of the A549 cell line (CLL-185, ATCC) with an IFN-inducible construct (MxA promoter/luciferase fusion) was kindly provided by Dr. Guenther Adolf (Boehringer-Ingelheim GmbH, Austria). The MxA promoter/luc fusion vector includes a 1.6 Kb BamHI fragment containing the murine MxA promoter and IFN response elements excised from pSP64-Mxp(PstI-PvuII)-rβglo (Lleonart et al. (1990) Biotechnology 8:1263-1267) and inserted upstream of a luciferase coding sequence.

RG assays were performed in triplicate wells in opaque 96-well, flat-bottom View Plate™ microplates with white walls and a clear bottom (PerkinElmer). For every assay type, it is preferable to incorporate positive control wells containing intron A (Schering-Plough) samples of varying concentrations and negative control wells containing only cells+ media.

Specifically, adherent 93D7 cells were harvested from flasks by removing the culture media, washing once with PBS, and trypsinization. Trypsinization was stopped by adding DMEM "complete" to the flask. The cells were collected from the flask, centrifuged, resuspended and counted. Their concentration was adjusted to 600,000/mL in complete DMEM.

Serum from immunized mice, hybridoma supernatants or purified anti-IFNα MAbs was pre-incubated with recombinant IFN subtypes, leukocyte IFN or PBMC-flu in 100 µl/well volumes for 1.5 hours at 37° C.+5% $CO_2$, after which 93D7 cells (50 µL of the 600,000/mL cell suspension=30,000 cells) was added per well and incubation was continued for an additional 5 hours. The final volume of the wells for the assay was 150 µL. Assays were then developed using the Britelite™ luminescence reporter gene system (Perkin Elmer) and read on a Wallac Microbeta Trilux™ scintillation and luminescence counter within 15 minutes of adding the substrate.

To assay for MxA induction by recombinant IFNα. The concentration of a solution (in DMEM complete) of IFNα was adjusted to contain the amount to be placed in each well in 100 μL. 100 μL of IFNα was placed in triplicate wells and then 50 μL of cells were added and incubated for 5 hours at 37° C.+5% $CO_2$.

To assay for MxA induction by SLE serum. 50 μL (e.g., no dilution) or 25 μL (e.g., 2× dilution) of SLE serum was placed in triplicate wells. The volume/well was then adjusted to 100 μL, by adding DMEM without FCS (note: any time serum samples of any type are added to wells using this assay, DMEM without FCS will be used) and then 50 μL of cells was added and incubated for 5 hours at 37° C.+5% $CO_2$.

To assay for blockade of MxA induction by PBMC-flu supernatants. 50 μl (e.g., no dilution) or serial dilutions of PBMC-flu supernatant was placed in triplicate wells. The volume of each well was then adjusted to 100 μL by adding DMEM with FCS, followed by the addition of 50 μL of cells and incubation for 5 hours at 37° C.+5% $CO_2$.

To assay for blockade of MxA induction by recombinant IFNα, SLE serum, or PBMC-flu supernatants using commercially-available Abs, mouse serum, or fusion supernatants. 50 μL or a desired dilution of recombinant IFNα, SLE serum, or PBMC-flu was added per well. 50 μL of either: (i) DMEM without FCS containing commercial polyclonal or monoclonal antibody preparations; (ii) 50 μL of mouse serum; or (iii) 50 μL of hybridoma supernatant was then added to each well to bring the total volume of each well to 100 μL. The plates were incubated for 1.5 hours at 37° C.+5% $CO_2$. After this time, 50 μL of cells was added and incubation continued for 5 hours at 37° C.+5% $CO_2$.

Britelite™ kit reagents/developing reagents (substrate vials, substrate buffer, uncolored DMEM) were set at room temperature 40 min prior to assay development. At 30 min pre-development, the assay plates were placed at room temperature. At 10 min pre-development, the lyophilized substrate was reconstituted with buffer (10 mL per vial).

After the 5 hour incubation period, all media was carefully removed from the wells using a multichannel pipet. Next, an adhesive white blocker was fixed to the bottom of the ViewPlate™ microplate. 90 μL of DMEM (without phenol red) was added per well. 90 μL of reconstituted Britelite™ reagent was added to each well, making sure to pipet up and down twice. (but without either splashing the well contents onto the sides of the wells or creating air bubbles) for thorough mixing of the reagent and the media. This was performed as quickly yet precisely as possible. The plate was sealed with a clear adhesive sealing strip. Within a span of greater than 1 min but not more than 15 min, the luminescence intensity of the plate(s) was read using the Wallac Microbeta® Trilux™ microplate scintillation and luminescence counter.

To obtain the percentage of blockade (based upon the ability of the included control antibody or antibody contained in the hybridoma supernatants to negate MxA-luciferase induction), the data was normalized in the context of the "positive control" (IFNα recombinant, SLE serum, or PBMC-flu supernatant+ cells) being 100% IFNα activity and the "negative control" (cells in media only) being 0% IFNα activity, using the software Prism® (GraphPad Software, Inc., San Diego, Calif.) and the Normalize algorithm to adjust all of the values to percentages according to the controls.

Example 1

Immunization and Selection of Monoclonal Antibody Cell Lines

Figure 2:
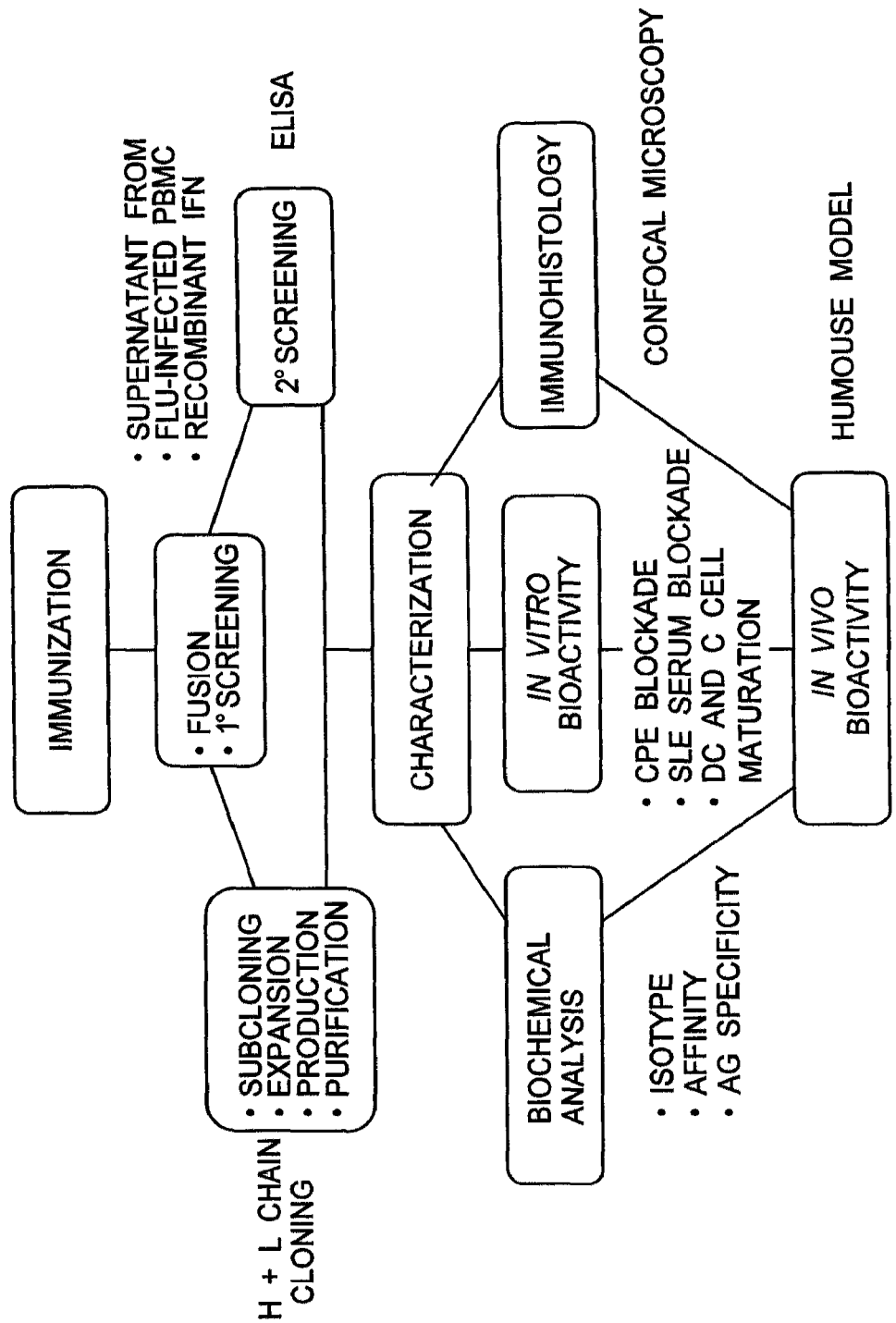
FIG. 2 shows a flow chart of the IFNα MAb development scheme.

A flow chart of the IFNα MAb development scheme is shown in FIG. 2. Groups of five 6-8 week old Balb/c female mice (Harlan) were immunized with 5-10 μg each natural leukocyte IFNα (1-2396, Lot #111K1603, Sigma) and/or a cocktail of recombinant proteins (5-10 μg each of the three recombinant IFNα subtypes A, B2, and F (obtained from PBL Biomedical Laboratories "PBL")) in MPL®+TDM emulsion (Sigma #M6536) at two to three week intervals according to the schedules indicated in Table 1, below. The MPL®+TDM emulsion is a Ribi Adjuvant system consisting of monophosphoryl-lipid A (MPL: detoxified endotoxin from S. Minnesota) and trehalose dicorynomycolate (TDM) in a 2% oil (squalene)-Tween 80-water emulsion. Antigen was administered via intraperitoneal (i.p.) or subcutaneous (s.c.) routes. Pre-fusion screening of serum collected from the mice was done at three titers (1:200, 1:2000, and 1:20,000) using the reporter gene (RG) assay, based upon a MxA-luciferase fusion protein via activation of the Type I IFN receptor, to detect blockade of IFNα bioactivity. Serum was collected from the mice via retro-orbital bleed seven days following the third boost and screen for neutralization of PBMC-flu bioactivity using the reporter gene (RG) assay described above. Mice exhibiting titers of at least 1:2000 for 50% neutralization were rested for four weeks and then given a final boost (either i.v. or i.p.) of 2.5 μg leukocyte IFN prior to splenocyte fusion with the murine myeloma Sp2/0-Ag14 (CRL-8287, ATCC) three days later. Fusions were performed in 50% PEG 1500 (Roche), and 1×HAT supplement (Sigma) in DMEM+15% FCS was used for hybridoma selection. Culture supernatants were screened 10-14 days later for neutralization of PBMC-flu. Based in the MxA/luc reporter gene (RG) bioassay, described above, of the mice immunized, 17 were able to neutralize the PBMC-flu supernatant by at least 50% at titers of 1:200, among these, 14 could neutralize at ≧50% at 1:2000 dilutions, and 3 continued to neutralize at titers up to 1:20000.

TABLE 1

Immunization and Selection of Monoclonal Antibody Cell Lines

|  | Protocol 1<br>Balb/c mice | Protocol 2<br>Balb/c mice | Protocol 3<br>Balb/c mice | Protocol 4<br>B6 mice | Protocol 5<br>B6 mice |
| --- | --- | --- | --- | --- | --- |
| Initiation | At day 0<br>10 μg natural IFNα<br>5 mice i.p.<br>5 mice s.c. | At day 0<br>10 μg IFNα A, B2 and F<br>5 mice i.p.<br>5 mice s.c. | At day 0<br>5 μg natural IFNα, split i.p. and s.c.<br>3 groups of 4 mice (received adeno- | At day 0<br>2.5 μg IFNα F<br>5 mice i.p.<br>2.5 μg IFNα F and B2<br>5 mice i.p. | At day 0<br>4 μg IFNα B2<br>5 mice i.p. |

TABLE 1-continued

Immunization and Selection of Monoclonal Antibody Cell Lines

|  | Protocol 1<br>Balb/c mice | Protocol 2<br>Balb/c mice | Protocol 3<br>Balb/c mice | Protocol 4<br>B6 mice | Protocol 5<br>B6 mice |
|---|---|---|---|---|---|
|  |  |  | mIFNα at Day −2, +2 or 1$^{st}$ boost) |  |  |
| 1$^{st}$ boost | At 2 weeks<br>5 μg natural IFNα<br>5 mice i.p.<br>5 mice s.c. | At 2 weeks<br>5 μg IFNα A, B2 and F<br>5 mice i.p.<br>5 mice s.c. | At 2 weeks<br>2.5 μg natural IFNα, split i.p. and s.c. | At 2 weeks<br>2 μg IFNα F<br>5 mice i.p.<br>2 μg IFNα F and B2<br>5 mice i.p. | At 1.5 weeks<br>2 μg IFNα A<br>5 mice i.p. |
| 2$^{nd}$ boost | At 5 weeks<br>5 μg natural IFNα<br>5 mice i.p.<br>5 mice s.c. | At 5 weeks<br>5 μg IFNα A, B2 and F<br>5 mice i.p.<br>5 mice s.c. | At 5 weeks<br>1.5 μg natural IFNα, split i.p. and s.c. | At 5 weeks<br>4 μg IFNα F<br>5 mice i.p.<br>4 μg IFNα F and B2<br>5 mice i.p. | At 4 weeks<br>2 μg IFNα F<br>5 mice i.p. |
| 3$^{rd}$ boost | At 10.5 weeks<br>2.5 μg natural IFNα<br>All mice i.p. | At 9 weeks<br>2 μg IFNα A, B2 and F<br>All mice i.p. | At 8.5 weeks<br>2 μg natural IFNα, i.p. | At 7 weeks<br>2 μg IFNα F<br>5 mice i.p.<br>2 μg IFNα F and B2<br>5 mice i.p. | N/A |
| 4$^{th}$ boost | At 16.5 weeks<br>2.5 μg natural IFNα<br>All mice i.p. | At 13.5 weeks<br>2.5 μg natural IFNα<br>All mice i.p. | N/A | At 9 weeks<br>2.5 μg IFNα A<br>All mice i.p. | N/A |

Note: Mice from protocols 1, 2 and 3 were used to make fusions 1 through 6. The fusions were performed pooling the cells from 2-3 mice within a protocol. Two mice (initially immunized with IFNα F in Protocol 6 were pooled to make fusion 8). In Protocol 5, two mice were pooled to make fusion 7, and three were pooled to make fusion 9.

Production and purification of monoclonal antibodies. As described above, mice were identified as candidates for fusion based upon the ability of their serum to neutralize the complex mixture of IFNα subtypes present in PBMC-flu. A series of 8 fusions were performed with splenocytes harvested from mice with acceptable serum titers. Splenocytes were fused with the Sp2/0-Ag14 murine myeloma cell line (ATCC Number CRL-1581, which was selected since it is unable to express endogenously-derived Ig chains), plated in 96-well flat-bottom tissue culture plates, and incubated for 12-15 days prior to screening of supernatants in order to detect a polyclonal antibody response via the RG assay protocol described above. Specifically, serum samples from the immunized mice were preincubated with supernatant from flu-infected PBMC for 1 hour at 37° C., after which the 93D7 cells were added for an additional 5 hours. At 5 hours, assays were developed and read on a luminescence counter. A summary of the first 8 fusions is shown in Table 2, below. Supernatants from the 8 fusions were screen from 3911 primary wells, and eight candidates (ACO-1 through 8), each isolated from Fusion 4, were identified based on their capacities to consistently demonstrate any visible decrease in PBMC flu (diluted 640-fold) mediated activation of MxA/luc production in the RG bioassay described herein. Hybridoma cell lines were subcloned by limiting dilution. Hybridomas producing anti-IFN-α MAbs were adapted to growth in Gibco PFHM-II (Invitrogen) and cultured in Integra CELLine flasks (Becton Dickinson). Supernatants were collected from the cell compartments every 5-7 days and frozen at −80° C. The MAbs were then purified from 50 ml batches of supernatant via FPLC over protein A columns followed by dialysis into PBS. The purified MAbs were aliquotted and stored at −80° C. ACO-1, 2, 3, 4, 5, and 8 were isotyped by ELISA as IgG2a (ACO-1), IgG2b (ACO-2), and IgG1 (ACO-3, 4, 5, 6 and 8). All of these candidates derived from fusions of splenocytes from mice initially immunized with leukocyte IFN or a mixture of IFN-α A, B2, and F recombinant proteins followed by a pre-fusion boost with leukocyte IFN; fusions performed from mice administered only the recombinant IFN-α subtypes failed to yield any candidates able to neutralize PBMC-flu.

TABLE 2

Summary of Fusions

| Fusion | 1 | 2 | 3 | 4 | 5 | 6 | 7 | 8 | Totals |
|---|---|---|---|---|---|---|---|---|---|
| Screened | 435 | 1644 | 560 | 396 | 136 | 217 | 191 | 332 | 3911 |
| Selected | 12 | 66 | 2 | 25 | 0 | 29 | 5 | 15 | 154 |
| Subcloned | 3 | 13 | 0 | 8 | 0 | 2 | 0 | 0 | 26 |
| Candidates | 0 | 0 | 0 | 6 | 0 | 2 | 0 | 0 | 8 |

Example 2

Neutralization of Commercially-Available Leukocyte IFNα or PBMC-Flu Supernatant Bioactivity by ACO-1, ACO-2, ACO-3, ACO-4 and ACO-5

Figure 3A:
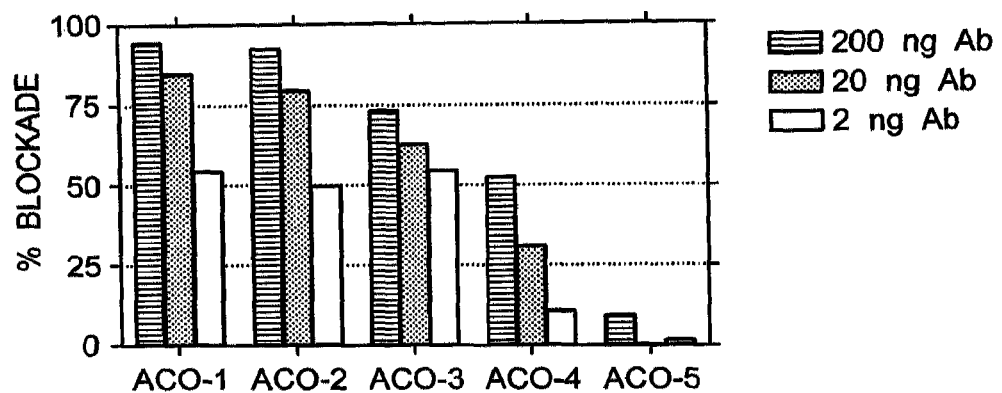
FIG. 3 shows neutralization of complex IFN sources by ACO-1, 2, 3, 4, and 5. (a) Neutralization of 600 pg of leukocyte IFN (Sigma) by the indicated amounts of each MAb was evaluated via the RG bioassay. Blockade percentages were calculated based upon the LCPS values obtained in the presence/absence of leukocyte IFN and the absence of any MAb. Values represent the mean of triplicates. (b) Neutralization of PBMC-flu (640-fold dilution) by each MAb. Blockade percentages were calculated as previously described. Values represent the mean of triplicates.

The anti-IFN-α MAbs shown to strongly bind and neutralize at least one IFN-α subtype were selected to examine their abilities to neutralize naturally-derived IFN preparations, which are known to contain a broad variety of IFN-α subtypes. For these studies, ACO-1 through 5 were titrated in the RG bioassay against both commercially-available leukocyte IFN and PBMC-flu supernatant prepared as describe above. ACO-1, 2, and 3 blocked leukocyte IFN bioactivity by at least 50% at all three MAb amounts tested (200, 20, and 2 ng) (FIG. 3a); ACO-4 achieved slightly more than 50% neutralization only when 200 ng was tested. In comparison, ACO-5 performed poorly against leukocyte IFN, maximally blocking less than 10% of the assay signal.

Figure 3B:
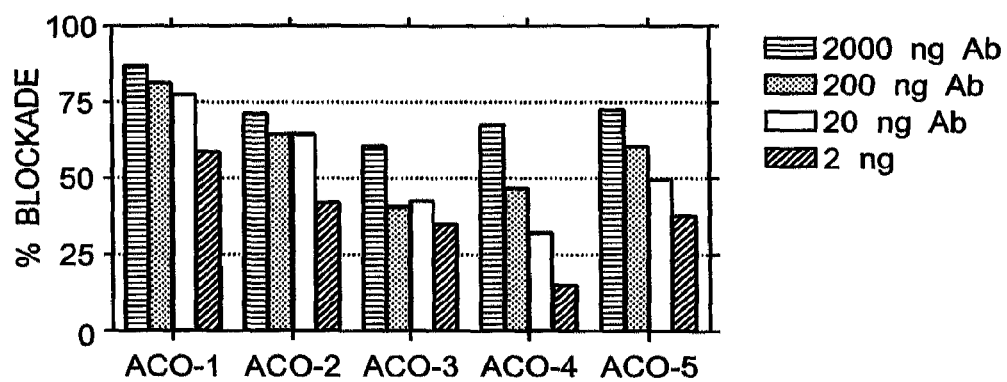

Comparative inhibition of various dilutions of PBMC-flu supernatant by defined concentrations of the monoclonal antibodies was performed using the RG assay described above. The absolute concentration of IFNα in the Flu/PBMC supernatant is unknown, so only relative neutralizing capacity is assessed in this study. When the five MAbs were titrated (2000, 200, 20, and 2 ng) against PBMC-flu however, ACO-5 was able to neutralize bioactivity by at least 50% at all but the lowest antibody amounts tested (FIG. 3b). ACO-1 exhibited the greatest potency when tested on PBMC-flu, blocking by at least 50% at all four titrated MAb amounts. The variance in neutralization of leukocyte IFN and PBMC-flu by ACO-5 is likely attributable to different IFN-α subtypes and/or their relative concentrations present in the two separate IFN sources used in our assays.

Example 3

Inhibition of Recombinant IFNα Subtype Bioactivity by ACO-1, ACO-2, ACO-3, ACO-4, ACO-5, ACO-6 and ACO-8

The IFNα-neutralizing candidates ACO-1 through 6 and ACO-8 were screened by both the RG assay as well as the traditional cytopathic effect (CPE) inhibition assay for neutralization of 15 recombinant IFNα subtypes as well as for neutralization of IFNβ. Recombinant IFN-α subtype proteins were obtained from PBL Biomedical Laboratories (Piscataway, N.J.); info@interferonsource.com, hereinafter "PBL"). The specific activities, as determined by the manufacturer, are shown in Table 3.

TABLE 3

Recombinant human IFN-α subtypes employed in the antibody characterizations.

| IFNα Protein subtype (gene) | Specific activity (U/mg) | Product # (PBL) | Lot # (PBL) | $RG_{max}$ Units | RG plateau (pg of IFN) | RG middle (pg of IFN) | CPE plateau (pg of IFN) | CPE middle (pg of IFN) |
|---|---|---|---|---|---|---|---|---|
| A (2a) | $3.8 \times 10^8$ | 11100-1 | 2167 | 47.5 | 125 | 62.5 | 50 | 25 |
| 2 (2b) | $2.77 \times 10^8$ | 11105-1 | 2122 | 8.31 | 30 | 15 | 25 | 12.5 |
| B2 (8) | $4.63 \times 10^8$ | 11115-1 | 2168 | 3.7 | 8 | 5 | 5 | 2.5 |
| C (10) | $2.31 \times 10^8$ | 11120-1 | 2118 | 3.47 | 15 | 4 | 5 | 2.5 |
| D [Val$^{114}$] (1) | $7.5 \times 10^7$ | 11125-1 | 2403 | 150 | 2000 | 750 | 750 | 375 |
| F (21) | $3.6 \times 10^8$ | 11130-9 | 2169 | 72 | 200 | 62.5 | 25 | 12.5 |
| G (5) | $2.33 \times 10^8$ | 11135-1 | 2104 | 116.5 | 500 | 62.5 | 50 | 25 |
| H2 (14) | $1.05 \times 10^8$ | 11145-1 | 2528 | 131.25 | 1250 | 200 | 25 | 12.5 |
| I (17) | $1.4 \times 10^8$ | 11150-1 | 1770 | 8.75 | 62.5 | 15 | 10 | 5 |
| J1 (7) | $2.6 \times 10^8$ | 11160-1 | 2105 | 260 | 1000 | 200 | 20 | 10 |
| K (6) | $1.48 \times 10^8$ | 11165-1 | 1359 | 92.5 | 62.5 | 155 | 25 | 12.5 |
| 1 [Ala$^{114}$] (D) | $1.4 \times 10^8$ | 11175-1 | 2106 | 17.5 | 125 | 15 | 200 | 100 |
| 4a (4a) | $2.12 \times 10^8$ | 11177-1 | 2180 | 10 | 10 | 2 | 25 | 12.5 |
| 4b (4b) | $1.8 \times 10^8$ | 11180-1 | 1424 | 45 | 250 | 31 | 100 | 50 |
| WA | $2.4 \times 10^8$ | 11190-1 | 2107 | 30 | 125 | 15 | 25 | 12.5 |
| IFN-β | $8.23 \times 10^7$ | | 2558 | 6.56 | | | | |

The neutralizing units (U) provided by the manufacturer has been assigned via an assay measuring the ability of the given subtypes to neutralize 50% (identified as 1 U/ml) of the cytopathic effect produced by vesicular stomatitis virus on bovine MDBK cells. Given that IFN-α potencies in bioassays are influenced by numerous variables (including assay type, individually prepared batches, and minor technique variations from one laboratory to another), as well as the fact that internationally-recognized standards for each subtype are unavailable, single lot numbers were consistently employed in these studies. The manufacturer-defined U of each recombinant that would yield maximal response in the RG bioassay ($RG_{max}$) was determined. Purified ACO-1, 2, 3, 4, 5, 6 and 8 were then titrated in the presence of these IFN-α subtype quantities in the RG bioassay. IFN-β (specific activity=8.23× $10^7$ U/mg) was obtained from PBL.

Figure 4A:
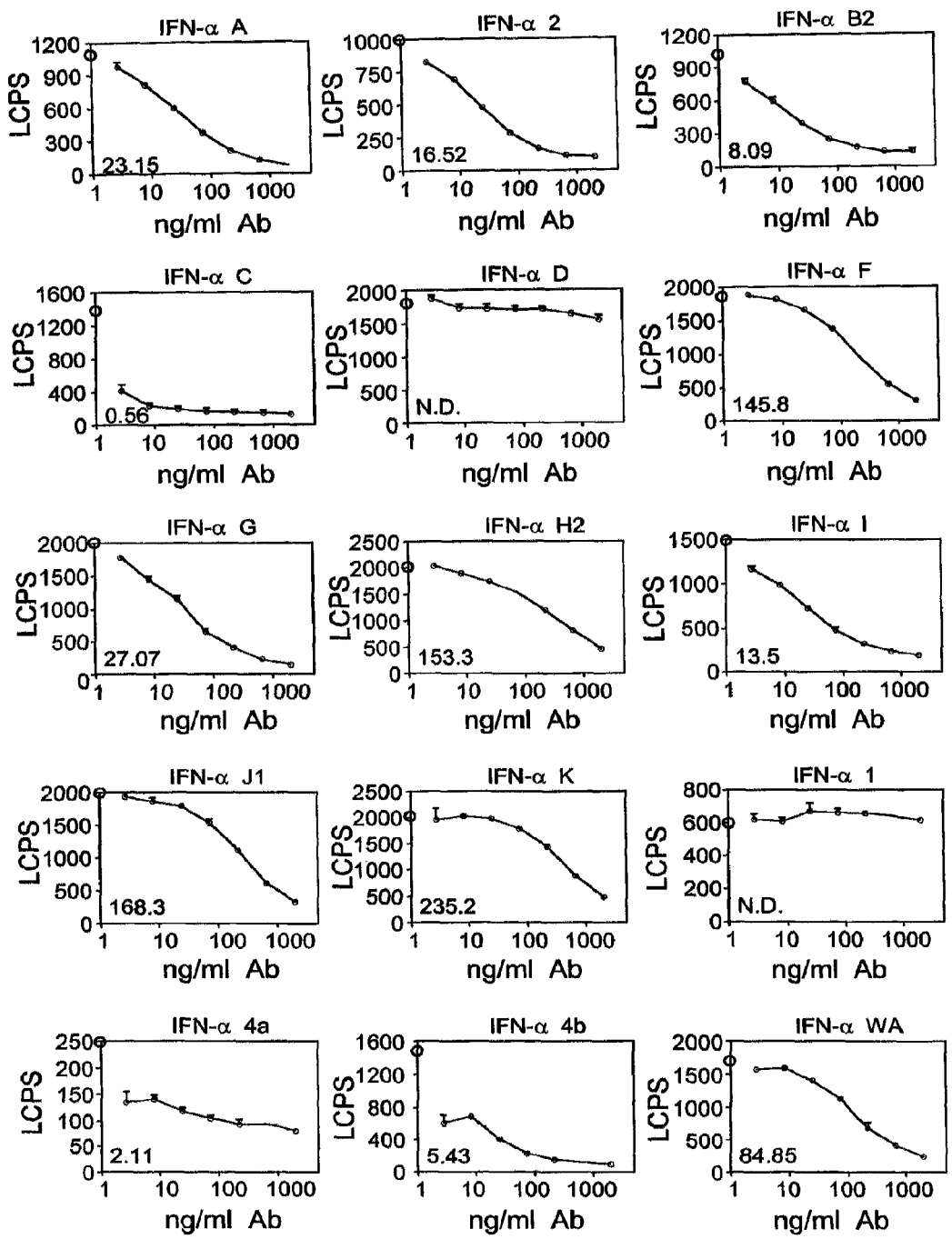
FIG. 4 shows neutralization of fifteen recombinant IFN-α subtypes by ACO-1. (a) Neutralization of the indicated IFN-α subtypes by increasing concentrations of ACO-1 was evaluated via the RG bioassay. The numerical value assigned to each curve represents the midpoint ($EC_{50}$) calculated from the LCPS value (luminescence counts per second) obtained in the absence of ACO-1 (indicated by open circles on the Y-axis) and the highest concentration of MAb tested (2000 ng/ml). N.D. signifies that no $EC_{50}$ value could be assigned. Data points were derived from triplicates. (b) Lack of neutralization of IFN-β by increasing concentrations of ACO-1, 2, 3, 4, 5, and 8. Data points were derived from triplicates.
Figures 4B, 5:
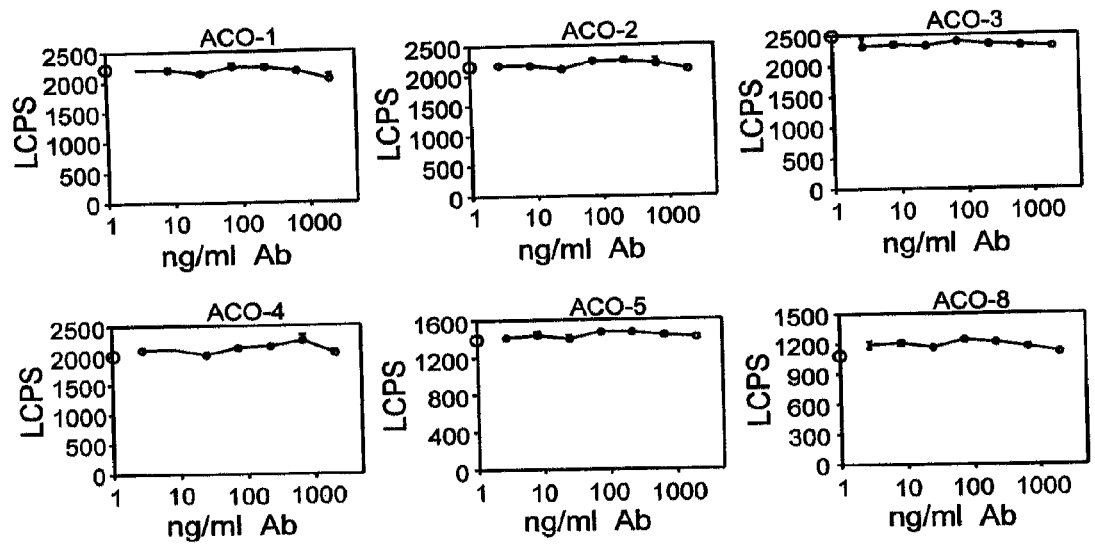
FIG. 5 shows the results of a multiplex analysis of monoclonal antibodies ACO-1, ACO-2, ACO-3, ACO-4, ACO-5, and ACO-6.

Representative RG bioassay data for the titration of ACO-1 against the $RG_{max}$ values of the fifteen IFN-α subtypes is shown in FIG. 4a. As described in the legend, numerical values were assigned to each ACO-1 titration against the designated subtypes based upon the $EC_{50}$ values determined for each. ACO-1 was unable to neutralize either IFN-α D or IFN-α 1, whereas the other thirteen subtypes could be neutralized at various antibody concentrations. The $EC_{50}$ results in ng/ml for all ACO-1, 2, 3, 4, 5 and 8 IFN-α-neutralizing MAbs are provided in Table 4. The percentage neutralization is shown in Table 5. Accordingly, ACO-1 and 2 appear similar in their capacities to neutralize twelve subtypes (IFN-α A, 2, B2, C, F, G, H2, I, J1, 4a, 4b, and WA) at concentrations of less than 300 ng/ml of antibody; ACO-1 also neutralized IFN-α K to this extent, though ACO-2 did not. ACO-3 and 4 neutralized nine (IFN-α A, 2, B2, C, I, J1, K, 4a, and WA) and six (IFN-α A, 2, B2, C, I, J1, and 4a) subtypes with less than 300 ng/ml, respectively. ACO-8 neutralized four subtypes (IFN-α 2, 1, 4a, and 4b) given the antibody concentration constraint, while ACO-5 strongly neutralized only three (IFN-α A, 2, and WA). None of the MAbs were able to neutralize IFN-β (FIG. 4b).

TABLE 4

Neutralization of recombinant IFN-α subtypes by ACO-1, 2, 3, 4, 5 and 8 ($EC_{50}$ ng/ml).

| IFN-α subtype | ACO-1 | ACO-2 | ACO-3 | ACO-4 | ACO-5 | ACO-8 |
|---|---|---|---|---|---|---|
| A | 23.15 | 64.17 | 4.82 | 23.57 | 3.61 | 335.5 |
| 2 | 16.52 | 38.57 | 0.31 | 19.21 | 0.23 | 180.4 |
| B2 | 8.09 | 6.09 | 1.01 | 172.3 | — | 308.2 |
| C | 0.56 | 2.19 | 3.22 | 152 | 539.3 | — |
| D | — | — | — | — | — | 373 |
| F | 145.8 | 54.05 | — | — | 704.7 | 349.8 |
| G | 27.07 | 43.29 | — | — | 465.9 | — |
| H2 | 153.3 | 123.7 | 637.1 | — | 604.7 | — |
| I | 13.5 | 8.4 | 6.32 | 147.1 | 528.1 | 342.6 |
| J1 | 168.3 | 212.6 | 206.6 | — | 646.5 | 488 |
| K | 235.2 | 352.9 | 239.5 | 475.3 | 444.8 | — |
| 1 | — | — | — | — | 576.7 | 211.2 |
| 4a | 2.11 | 5.6 | 0.04 | 55.59 | 597.6 | 134.4 |
| 4b | 5.43 | 7.27 | — | — | 669.9 | 271.8 |
| WA | 84.85 | 106.8 | 250.4 | — | 140.5 | — |

TABLE 5

Percentage neutralization of $RG_{max}$ IFN amounts by 2 micrograms/mL of antibody

| IFN-α subtype | ACO-1 | ACO-2 | ACO-3 | ACO-4 | ACO-5 | ACO-8 |
|---|---|---|---|---|---|---|
| A | 93.6 | 89.4 | 86.7 | 59.5 | 92.7 | 73.1 |
| 2 | 90.3 | 88 | 88.8 | 85.3 | 95.8 | 77.6 |
| B2 | 87 | 87.5 | 87 | 75.2 | 29.2 | 77 |
| C | 91.4 | 92.9 | 85.8 | 70.9 | 28.4 | 30.5 |
| D | 12.5 | 20.8 | 0 | 8.2 | 30.4 | 42 |
| F | 83.7 | 88 | 0 | 1 | 24.9 | 55.2 |
| G | 92.7 | 95 | 0 | 0 | 59.6 | 37.3 |
| H2 | 77.5 | 87 | 22.6 | 6.5 | 16.5 | 25.4 |
| I | 87.1 | 93.3 | 79.6 | 46.7 | 58.9 | 68.5 |
| J1 | 83.9 | 81.9 | 45.2 | 2.9 | 20.5 | 31.8 |
| K | 77.9 | 71.2 | 60 | 12.9 | 53 | 25.2 |
| 1 | 0 | 13.5 | 1 | 5.1 | 46.7 | 75.7 |
| 4a | 67.8 | 67.4 | 64 | 58.3 | 31.6 | 71.3 |
| 4b | 93.7 | 92.4 | 9 | 4.8 | 24.2 | 63.2 |
| WA | 86.9 | 84 | 55.5 | 5.4 | 85.2 | 14.3 |
| IFN-β | 9 | 0 | 6.5 | 1 | 0 | 0 |

The CPE assay was set up similarly to the RG assay with untransfected A549 cells (ATCC Number CCL-185, a human lung carcinoma cell line): assays are performed in standard 96-well flat-bottom tissue culture plates. Following pre-incubation (1 hour at 37° C.) of antibodies with the IFNα subtypes and addition of cells 5 hours later, mouse encephalomyocarditis virus (EMCV) was added and the cells were incubated for 48 hours prior to staining with crystal violet for assessment of live cells remaining. For both the RG and CPE assays, the quantities of each IFNα subtype used were determined via prior titrations of the recombinant IFNα proteins to yield either maximal MxA-luciferase induction (RG) or protection from cell death (CPE) in the assay. The data shown in Table 6 represents the percentage of bioactivity blockade demonstrated by each ACO monoclonal antibody against the respective IFNα subtypes (corresponding genes encoding the subtypes are indicated in parentheses) in the CPE assay. For both the CPE assay, the quantities of each IFNα subtype used were determined via prior titrations of the recombinant IFNα proteins to yield either maximal protection from cell death (CPE). N/D=not determined. As shown, ACO-1 and ACO-2 are capable of blocking the largest number of IFNα subtypes at levels of 90% under the assay conditions, whereas ACO-6 is the most restricted. In most cases, the outcomes of the RG and CPE assays correlate with one another.

TABLE 6

Percentage Neutralization of IFNα subtype activity by Mabs in the CPE Assay.

| IFN-α | ACO-1 | ACO-2 | ACO-3 | ACO-4 | ACO-5 | ACO-6 |
|---|---|---|---|---|---|---|
| A (2a) | 95.7 | 81.4 | 93.9 | 94.6 | 90.0 | 0.0 |
| 2 (2b) | 80.1 | 75.8 | 96.6 | 92.4 | 93.9 | 0.0 |
| B2 (8) | 98.8 | 98.6 | 96.4 | 49.6 | 13.0 | 0.0 |
| C (10) | 99.4 | 98.2 | 92.1 | 65.1 | 21.9 | 0.0 |
| D (1) | 33.0 | 38.5 | 0.0 | 11.3 | 0.0 | 0.0 |
| F (21) | 96.6 | 95.4 | 0.0 | 23.5 | 34.5 | 0.0 |
| G (5) | 99.0 | 97.4 | 0.0 | 0.0 | 80.8 | 0.0 |
| H2 (14) | 95.9 | 98.3 | 92.6 | 90.7 | 78.9 | 0.0 |
| I (17) | 98.0 | 99.8 | 95.0 | 85.1 | 56.2 | 0.0 |
| J1 (7) | 98.1 | 97.3 | 92.8 | 47.1 | 61.1 | 0.0 |
| K (6) | 98.3 | 99.5 | 90.1 | 82.1 | 85.3 | 0.0 |
| 4a (4a) | 82.9 | 83.6 | 81.3 | N/D | 0.0 | 0.0 |
| 4b (4b) | 98.7 | 96.7 | 0.0 | 0.0 | 53.7 | 0.0 |
| WA (16) | 88.7 | 94.6 | 91.0 | N/D | 100 | 0.0 |
| 1 (1) | 16.7 | 22.9 | 15.9 | 11.9 | 64.3 | 0.0 |
| IFN-α | N/D | N/D | N/D | N/D | N/D | N/D |

Example 4

Multiplex Analysis of ACO-1, ACO-2, ACO-3, ACO-4, ACO-5, and ACO-6

Multiplex analysis was conducted to assess whether spatially distinct binding domains were involved. The ACO antibodies were analyzed combinatorially for their abilities to simultaneously bind IFNα-A via multiplex analysis on a Luminex™ 100 system. Beads coupled with unlabeled ACO antibodies (Capture) were incubated with recombinant IFNα-A at the concentration indicated and then exposed to PE-labeled ACO antibodies (Reporter). This examination revealed that ACO-5 can multiplex with any of ACOs-1, -2, -3, and -4 (see light shading in FIG. 5). Multiplexing additionally occurs when ACO-4 is employed as a capture antibody and ACO-3 as a reporter antibody. Accordingly, ACO-5 binds a spatially distinct domain of IFNα-A than that bound by ACO-1, 2, -3 and -4. Similarly, ACO-3 and ACO-4 bind spatially distinct domains of IFNα-A. Results with ACO-6 were negative in all cases.

Example 5

Affinity Determinations for ACO-1, ACO-2, ACO-3, ACO-4, ACO-5 and ACO-6

Kinetic analysis of the ACO antibodies against IFNα-A was performed using Biacore™ 2000 and 3000 optical biosensors equipped with CM5 sensor chips and equilibrated with 10 mM HEPES, 150 mM NaCl, 0.005% P20, 0.1 mg/ml BSA, pH 7.4 at 25° C. For each of ACOs 1 through 6, antibodies were first buffer-exchanged from Tris-glycine buffer to 10 mM sodium acetate buffer, pH 5.0 using a fast desalting column and then immobilized on three flow cell surfaces using standard amine-coupling chemistry, while the fourth was left unmodified to serve as a reference. Final MAb immobilization densities ranged from 500-1100 RU (response units). Binding responses were monitored as IFNα-A was flowed in titrated amounts (0, 0.31. 0.93. 2.78. 8.33. 25.0 and 75.0 nM) over the antibody and reference flow cells at a rate of 50 μl/min. Association of the Ab/Ag complex was monitored for four minutes and the dissociation was monitored for twelve minutes. The surfaces were regenerated with 1/1000 $H_3PO_4$ (except ACO-5, which required 1/200 $H_3PO_4$) at the end of each binding cycle. Assays were performed in triplicate. The results are shown in Table 7. The $K_D$ values for the five anti-IFNα MAbs covered a range inversely proportional to the breadth of IFNα subtypes neutralized by each MAb as well as their potency in blocking leukocyte IFN and PBMC-flu bioactivity. ACO-1 exhibited the lowest affinity (5.61× $10^{-9}$ M), while ACO-5 exhibited a 14-fold higher affinity (4.00×$10^{-10}$ M). ACO-6 does not bind to IFNα-A and therefore no rates were obtainable.

TABLE 7

Biacore Kinetic Analysis of ACO-1 through ACO-6 with IFN-α A

| Antibody | $K_a$ (M$^{-1}$s$^{-1}$) | $K_d$ (s$^{-1}$) | $K_D$ (M) |
|---|---|---|---|
| ACO-1 | 7.86 × 10$^4$ | 4.41 × 10$^{-4}$ | 5.61 × 10$^{-9}$ |
| ACO-2 | 9.87 × 10$^4$ | 1.90 × 10$^{-4}$ | 1.92 × 10$^{-9}$ |
| ACO-3 | 5.12 × 10$^5$ | 2.36 × 10$^{-4}$ | 4.61 × 10$^{-10}$ |
| ACO-4 | 5.82 × 10$^5$ | 2.74 × 10$^{-4}$ | 4.71 × 10$^{-10}$ |
| ACO-5 | 5.25 × 10$^5$ | 2.10 × 10$^{-4}$ | 4.00 × 10$^{-10}$ |
| ACO-6 | N/A | N/A | N/A |

Example 6

Solid-Phase Binding of IFNα Subtypes by ACO-1, ACO-2, ACO-3, ACO-4, ACO-5, and ACO-6

Figure 6:
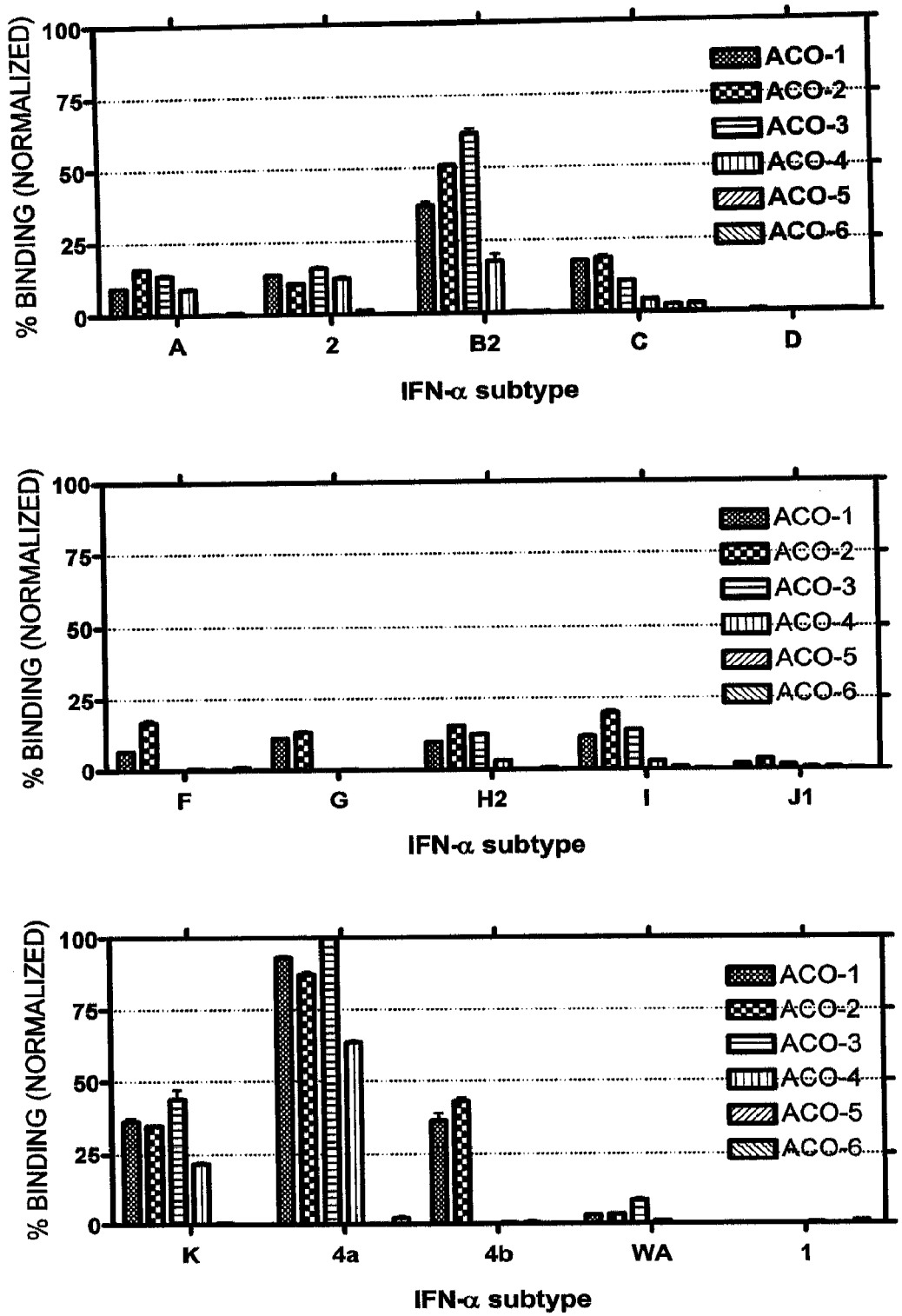
FIG. 6 shows the results of solid-phase binding assay of IFNα subtypes by monoclonal antibodies ACO-1, ACO-2, ACO-3, ACO-4, ACO-5, and ACO-6.
Figure 7A:
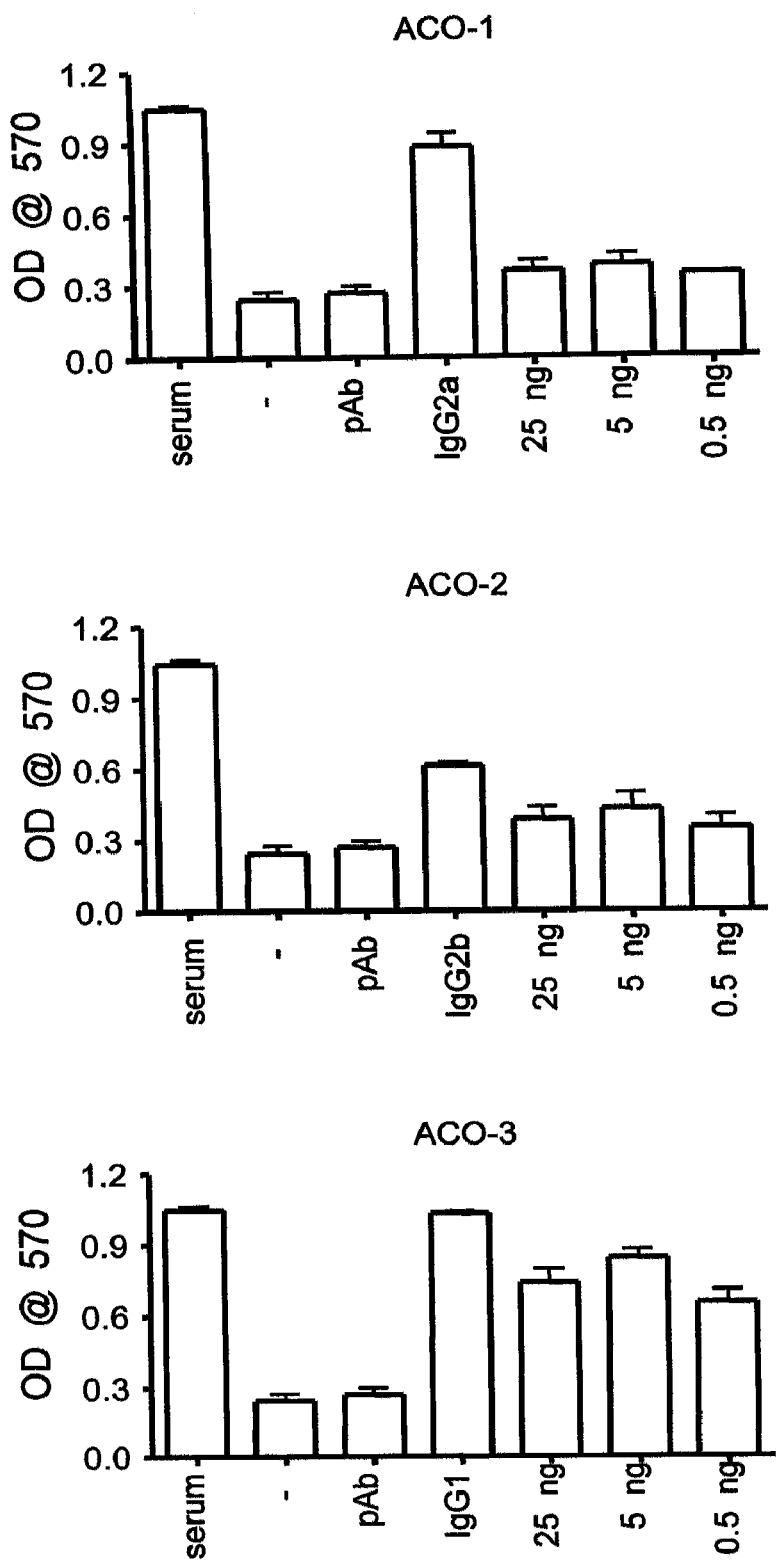
FIG. 7 shows the neutralization of SLE patient serum samples SLE-43 (a), SLE-133 (b), SLE-140 (c), and SLE-BD (d) bioactivity evaluated by the CPE assay. Amounts of MAb tested are indicated. Controls include serum alone, media only (−), and a pan-neutralizing polyclonal antibody (pAb, rabbit and anti-human IFNα, PBL). Values represent the mean of triplicates.
Figure 7B:
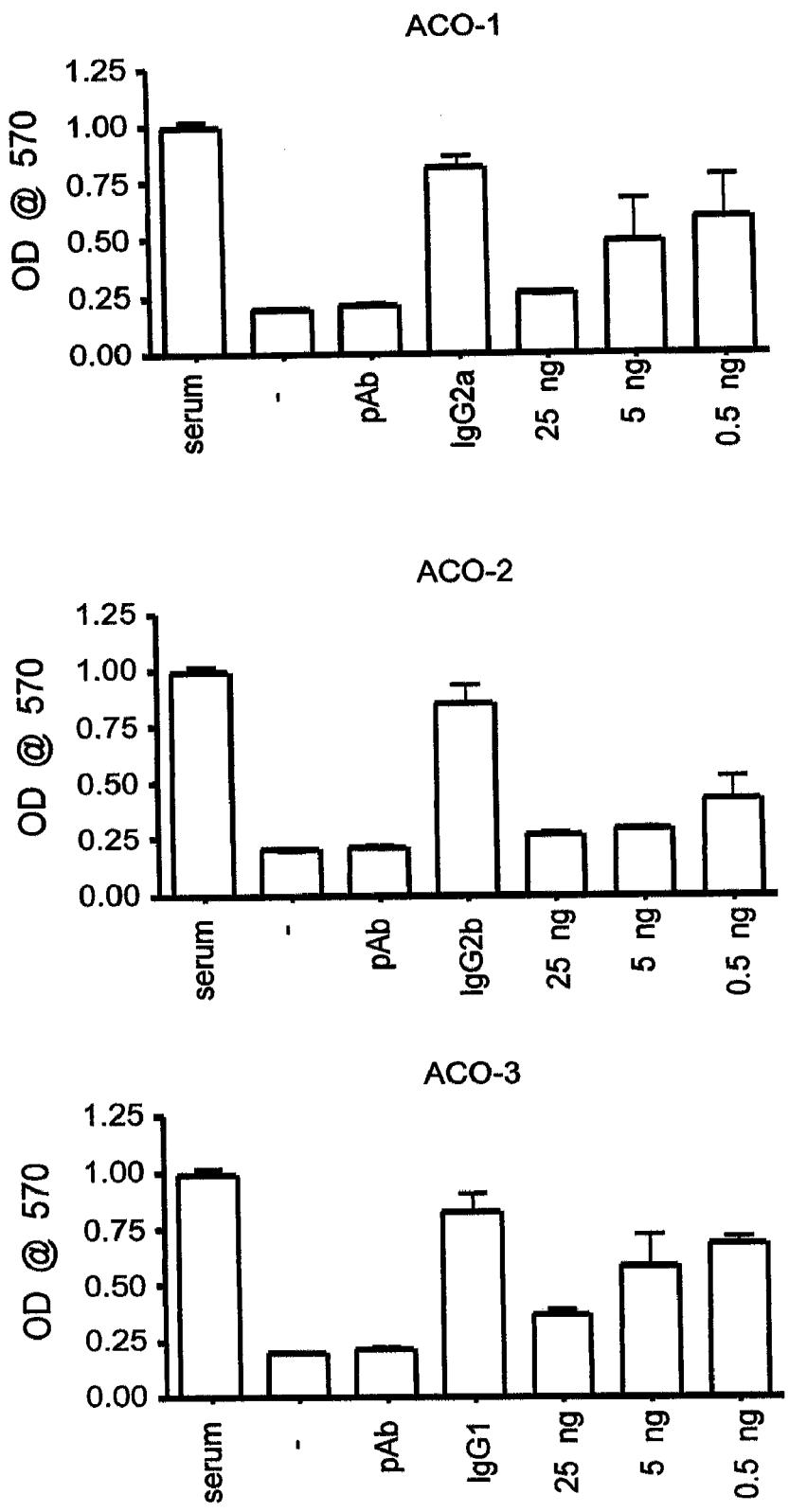
Figure 7C:
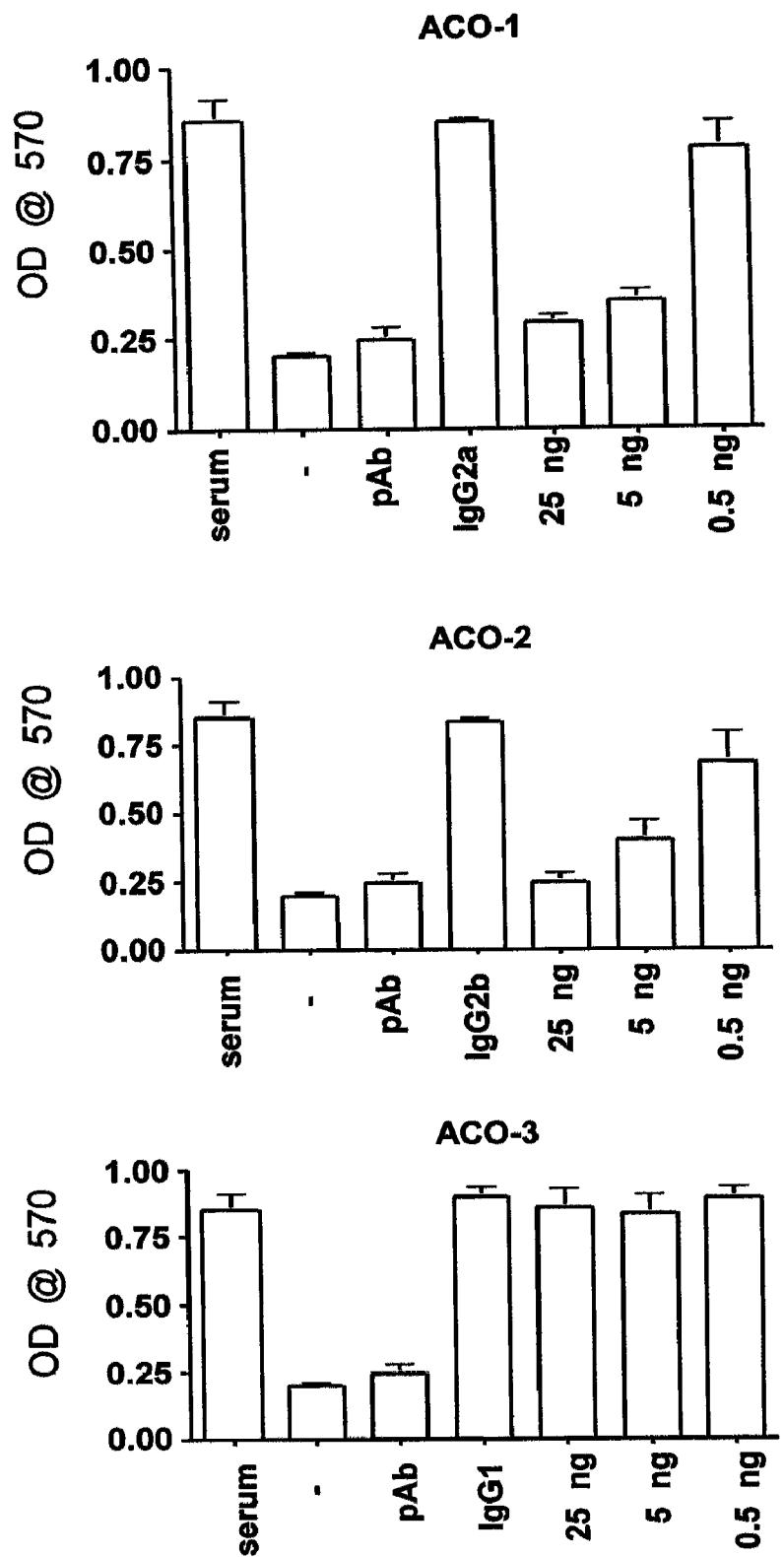
Figure 7D:
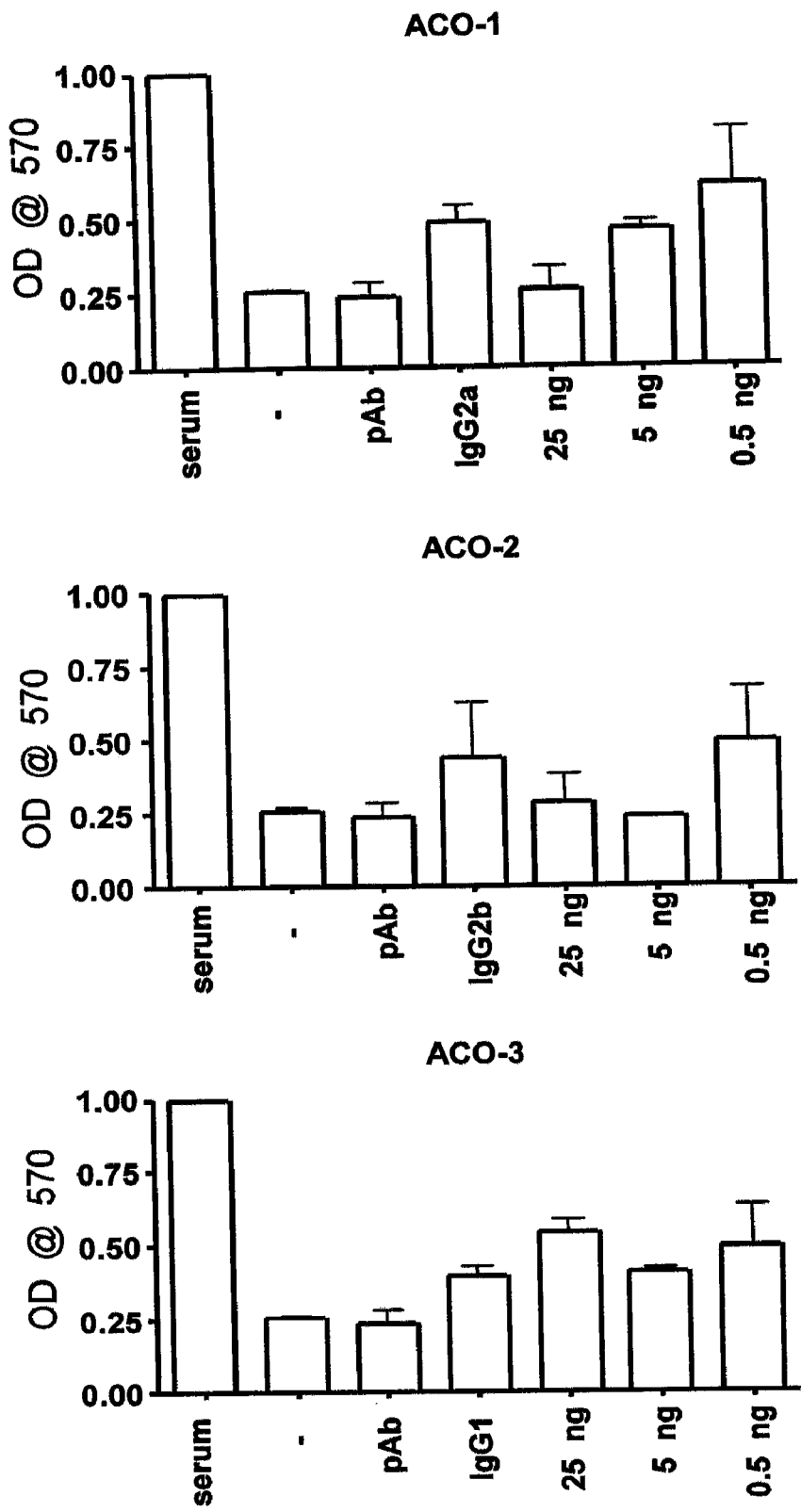

Solid-phase binding of all 15 IFNα subtypes was evaluated for screening of MAb specificity by ELISA assay. Briefly, 50 μl/well of 1 μg/ml of a recombinant IFNα protein subtype were coated overnight at 4° C. on ELISA plates (NUNC MaxiSorp) plates. Coated plates were blocked with PBS+1% BSA and incubated with 50 μl of 25 ng ACO candidate MAb in PBS for 1 hour at 37° C. The assays were developed by incubation with 50 μl/well of an HRP conjugated goat anti-mouse-IgG (Jackson ImmunoResearch) at room temperature for 30 minutes followed by incubation with 100 μl/well of TMB substrate solution (Zymed) for 15 minutes. The reaction was stopped with 100 μl/well of 1 N HCl and read at OD$_{450}$ on an ELISA plate reader. Binding percentages were calculated by normalizing background signal values with maximal signal values across the assay (observed for IFNα-4-a). The results are shown in Table 8 and FIG. 6. Both ACO-1 and 2 bound the identical twelve IFN-α subtypes that they effectively neutralized in the RG bioassay at signals at least 2-fold greater than isotype-matched controls; binding of IFN-α subtypes B2, K, 4a, and 4b demonstrated signals more than 20-fold over controls. Differences between binding and neutralization capacities were observed, however, among ACO-3, 4, 5, and 8. In the case of ACO-3, the ELISA signals for subtypes B2, K, and 4a were the highest, despite the fact that the EC$_{50}$ value for neutralization of IFN-α K was greater than 200-fold higher that the EC$_{50}$ for IFN-α B2 and 4-fold higher for IFN-α 4a; significant binding of subtype 31, which was neutralized in the bioassay was not detectable. The binding and neutralization profiles for ACO-4 and 5 presented inverse relationships with one another. While ACO-4 and 5 strongly bound one subtype each (IFN-α 4a and 2, respectively), ACO-4 was able to bind more subtypes than it neutralized, and ACO-5 was able to neutralize (albeit at high EC$_{50}$ values) more subtypes than it bound. A potential explanation could lie in accessibility differences of the specific epitopes recognized by these two MAbs in aqueous (RG) versus solid-phase (ELISA) assays. ACO-8 failed to strongly bind any of the IFN-α subtypes tested; it exhibited binding of less that 20-fold to IFN-α D, 1, and 4a. ACO-6 failed to bind to any of the subtypes.

TABLE 8

Binding of recombinant IFN-α subtypes by ACO-1, 2, 3, 4, 5, and 8.

| IFN-α subtype | ACO-1 | ACO-2 | ACO-3 | ACO-4 | ACO-5 | ACO-8 |
|---|---|---|---|---|---|---|
| A | <u>6.4</u> | <u>9.8</u> | <u>8.4</u> | <u>7.2</u> | 1.7 | 1.0 |
| 2 | <u>8.7</u> | <u>7.0</u> | <u>9.8</u> | <u>9.0</u> | <u>3.4</u> | 1.1 |
| B2 | 24.3 | 32.7 | 39.2 | <u>13.2</u> | 1.3 | 1.1 |
| C | <u>5.2</u> | <u>5.4</u> | <u>3.2</u> | <u>2.2</u> | 1.5 | 1.0 |
| D | 1.2 | 1.4 | 1.0 | <u>2.5</u> | 1.7 | <u>3.7</u> |
| F | <u>5.3</u> | <u>10.8</u> | 1.0 | <u>2.8</u> | 1.4 | 1.4 |
| G | <u>7.4</u> | <u>8.5</u> | 0.9 | <u>2.4</u> | 1.3 | 1.1 |
| H2 | <u>7.5</u> | <u>10.9</u> | <u>9.0</u> | <u>4.5</u> | 1.1 | 1.3 |
| I | <u>7.8</u> | <u>12.5</u> | <u>8.9</u> | <u>3.9</u> | 1.3 | 1.1 |
| J1 | <u>2.1</u> | <u>3.0</u> | 1.8 | <u>2.6</u> | 1.4 | 1.1 |
| K | 23.2 | 22.3 | 27.7 | 15.1 | 1.4 | 1.1 |
| 1 | 1.3 | 1.1 | 1.0 | <u>2.7</u> | 1.6 | <u>2.8</u> |
| 4a | 54.9 | 51.6 | 59.0 | 38.3 | 1.4 | <u>3.3</u> |
| 4b | 22.2 | 26.1 | 1.0 | <u>2.6</u> | 1.4 | 1.4 |
| WA | <u>3.2</u> | <u>3.3</u> | <u>6.2</u> | <u>3.2</u> | 1.6 | 1.1 |

Underlined indicates signals greater than 2-fold over matched controls. Bold indicates signals greater than 20-fold over matched controls. Signals of less that 2-fold over matched controls indicate insignificant binding.

Example 7

Blockade of SLE Patient Serum Bioactivity by ACO-1, 2 and 3 Monoclonal Antibodies An antiviral assay was used to evaluate the ability of the anti-IFN-α MAbs to neutralize the protective activity of serum from SLE patients with active disease against the death of A540 cells (CCL-185, ATCC) upon infection with encephalomyocarditis virus (RMCV). The antibodies exhibiting the broadest IFN-α subtype, leukocyte IFN, and PBMC-flu neutralization profiles (ACO-1, 2 and 3) were tested. The SLE serum was obtained from four active SLE patients (identified as SLE-43, 133, 140 and BC) selected upon the basis of IFN and granulopoiesis gene expression signatures characterized from their blood mononuclear cells. SLE sera were screen for protection against viral infection in the CPE bioassay prior to MAb neutralization testing. The RG assay was not employed in these analyses due to inhibition by serum factors of cell binding to the ViewPlate™ microtiter plates during the comparatively shorter incubation period (5 hours) of the RG bioassay versus the CPE assay (48 hours). Vero cells (CCL-81, ATCC) were infected with EMCV (VR-129B, ATCC) to prepare working viral stocks from supernatants. Assays were performed in triplicate in tissue culture-treated, flat-bottom 96-well plated incubated at 37° C.+$CO_2$ with A549 cells (15,000 cells/well in 50 µl each) overnight. Anti-IFN-α MAbs and serum from SLE patients were then added to the plated (100 µl/well) and preincubated for 4 hours prior to addition of EMCV diluted to the minimal concentration in 50 µl able to kill 100% of unprotected cells in 48 hours. Incubation was continued for 48 hours, followed by staining with crystal violet and reading at $OD_{570}$ in an ELISA plate reader. Controls were serum alone, media only (−), and a pan-neutralizing polyclonal antibody (pAb, rabbit anti-human IFN-α, PBL). The results shown in FIG. 7*a-d* represent the mean of triplicates. Despite their lower affinities, ACO-1 and 2 were capable of neutralizing all four sera to some degree. ACO-3 was unable to block SLE-43, 140 or BC, The ability for relevant isotype control antibodies to block serum in some instances (IgG2b for SLE-43, all three isotypes for SLE-BC) likely resulted from natural variations in other serum constituents from one patient to another that were cytotoxic to the cells employed in the assay.

Example 8

Cross Reactivity of ACO-1 and ACO-2 with Primate IFN-α

Figure 8A:
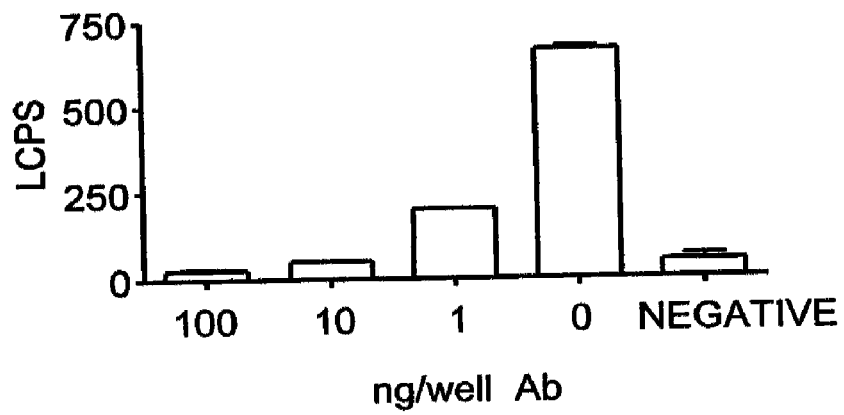
FIG. 8A-C shows the cross-reactivity of ACO-1 (A), ACO-2 (B), and ACO-3 (C) with 156 pg/well Macaque IFN.
Figure 8B:
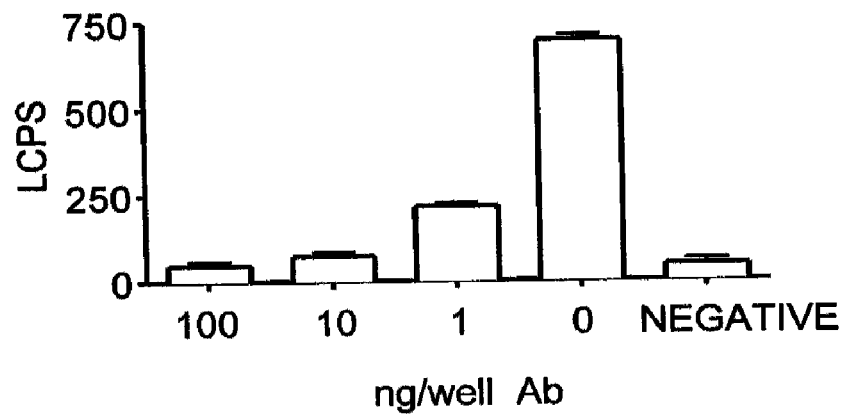
Figure 8C:
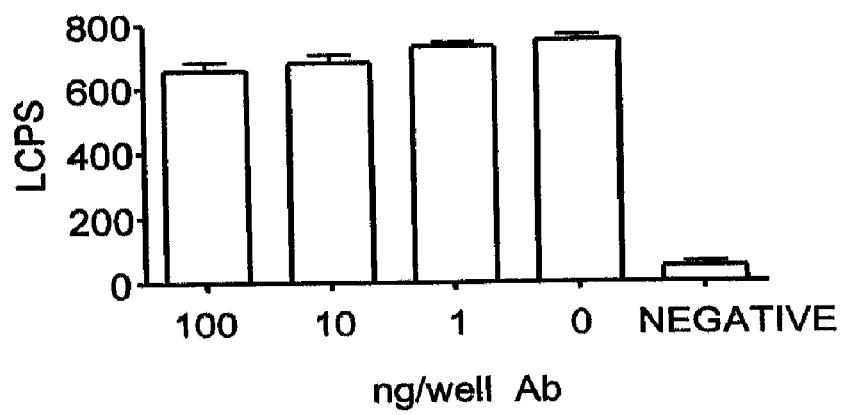

To conduct preclinical safety/toxicology studies as a prelude to human clinical trials, it is useful to identify an animal model where endogenous IFN-α is reactive with the humanized anti-IFN-α monoclonal antibody. The ability of two candidates, murine anti-human IFN-α Abs ACO-1 and ACO-2, to neutralize primate IFN-α were tested. Specifically, the ability of the antibodies to block induction of an MxA-luciferase reporter gene in A549 cells when stimulated with purified macaque IFN-α 4b (156 pg/well) was determined. As shown in FIG. 8, the antibodies ACO-1 and ACO-2 potently block reporter gene induction (A and B, respectively) while ACO-3 is unable to block even at high concentrations (C). Homology between human and Macaque IFN-α is highly conserved. Moreover, commercially available anti-human IFN-α antibodies have been shown to cross-react with Rhesus and cynomologous homologs. These data suggest that primates provide a suitable safety screening model.

Example 9

Sequence of ACO-1 Heavy and Light Chains

RT/PCR was performed using degenerate primer pools to amplify mRNA from the hybridoma expressing ACO-1. Heavy chain variable region mRNA was amplified using a set of six degenerate primer pools (HA to HG) and light chain variable region mRNA was amplified using a set of eight degenerate primer pools (LA to LI). Amplification products were obtained with primer pools: HA, HB, HE, HF, LB, LC and LG. No PCR product was amplified with pool LI, therefore the light chain is from the kappa cluster. Each product was cloned and several clones from each sequenced.

Two different heavy chain sequences were identified. Pools HA and HF amplified a single sequence that codes for a truncated heavy chain with a stop codon at the end of Framework Region 3. It is therefore unlikely that this heavy chain could form an antibody capable of binding to antigen.

Pools HB and HE amplified a single sequence that was different from that of HA and HF and codes for a full length mouse $V_h$ region as shown in FIG. 9. The full length heavy chain DNA sequence is SEQ ID NO:1, and the full length amino acid sequence is SEQ ID NO:2. The DNA sequences encoding CDRs $V_H1$ (TACACCTTCACCAACTACTGGATGCAC; SEQ ID NO:3), $V_H2$ (GAGATTAATCCTAGCCACGGTCGTACTATCTACAATGAAAACTTCAAGAGC; SEQ ID NO:5) and $V_H3$ (GGGGGACTGGGACCCGCCTGGTTTGCTTAC; SEQ ID NO:7) are shown in italics while the amino acid sequences $V_H1$ (YTFTNYWMH; SEQ ID NO:4), $V_H2$ (EINPSHGRTIYNENFKS; SEQ ID NO:6) and $V_H3$ (GGLGPAWFAY; SEQ ID NO:8) are underlined.

Two light chain sequences were identified. Pools LB and LC amplified a single sequence that aligned with the well documented, aberrant, truncated kappa light chain that is found in some hybridomas. Pool LG amplified a single sequence that was full-length and differed from that amplified in pools LB and LC. The light chain sequence is shown in FIG. 10. The full length light chain DNA sequence is SEQ ID NO:9, and the full length amino acid sequence is SEQ ID NO:10. The DNA sequences encoding CDRs $V_L1$ (AGTGCCGGCTCAAGTGTAGATTCCAGCTATTTGTAC; SEQ ID NO:11), $V_L2$ (AGC ACATCCAACCTGGCTTCT; SEQ ID NO:13) and $V_L3$ (CATCAGTGGAGTAGTFACCCATTCACG; SEQ ID NO:15) are shown in italics, while the amino acid sequences $V_L1$ (SAGSSVDSSYLY; SEQ ID NO:12), $V_L2$ (STSNLAS; SEQ ID NO:14) and $V_L3$ (HQWSSYPFT; SEQ ID NO:16) are underlined.

The analysis of the sequences obtained from hybridoma ACO-1 is summarized in Table 9. The variable regions show high homology to their closest human germline sequences (67% to 65%) and the framework sequences have close homologues in the human germline database.

TABLE 9

| | Clone ACO-1 | |
|---|---|---|
| | H Chain | L Chain |
| $CDR^a$ 1 Length | $V_H1$: 9aa | $V_L1$: 12aa |
| CDR 2 Length | $V_H2$: 17aa | $V_L2$: 7aa |
| CDR 3 Length | $V_H3$: 10aa | $V_L3$: 9aa |
| Mouse Germline | J558.33 | Vk ae4 |
| Closest Human Germline[b] | VH1-46 (67%) | L6 (65%) |
| Closest Human FW1[b] | VH1-46/18/8/3/2 (80%) | L20/A11/L6 (69%) |
| Closest Human FW2[b] | VH1-46/69/18/2 (78%) | L4/18a/018/012/L19/L18 L12/L11/08/02/L9/L8/L5 (80%) |
| Closest Human FW3[b] | VH1-69 (65%) | A26/A10/A14 (75%) |
| Closest Human J[b] | J4 (92%) | J2 (92%) |

[a]CDR definitions and sequence numbering according to Kabat
[b]Germline ID(s) indicated followed by % homology Example 10

Humanization of a Monoclonal Antibody and its Characterization

Humanized antibody is made by grafting the murine complementarity-determining regions into a human antibody framework (CDR-grafting) using methods known in the art (See Jones, et al., (1986) Nature, 321:522-525; Reichmann et al., (1988) Nature, 332:323-329; Presta (1992) Curr. Op. Struct. Biol., 2:593-596; and Clark (2000) Immunol. Today 21:397-402). The humanized antibody may be capable of the same binding and functional parameters as the murine monoclonal antibodies described above.

Example 11

Treatment of SLE Using Humanized Monoclonal Antibody

Microarray analysis will be used to monitor the IFNα signature according to methods known in the art and described in Bennett, et al. (2003) supra and Baechler, et al. (2003) supra. This new tool will serve to stratify (i.e. positive IFNα signature inclusion criteria), as well as monitor patients. Use of this analysis also is useful to determining which patients are suitably treated by the compositions and methods of this invention. In one aspect, administration of an antibody of this invention will extinguish this signature. In one aspect, one of skill in the art can determine when the object of a method of this invention is met, and an effective amount of antibody has been delivered, when is defined as the amount required the IFNα signature is suppressed by 50% for an effective amount of time, e.g. about 4 weeks.

An effective amount will be infused, e.g., from about 1 mg/kg, the second 2.5 mg/kg, the third 5 mg/kg antibody, and a fourth, if necessary, will be at 10 mg/kg. The "calculated optimal dose" for each patient is defined as the amount that can be safely administered and gives at least 50% suppression of the IFNα signature for about four weeks.

Patients will be monitored weekly for IFNα signature. The time to reappearance of the IFNα signature will determine the dosing interval. For example, if the 1 mg/kg dose gives 50% signature reduction for only 2 weeks, that patient would receive a 2nd does of 2.5 mg/kg. If weekly monitoring revealed a 50% suppression of the signature for only 3 weeks, the patient would receive their 3rd does of 5 mg/kg. A maximum dose of 10 mg/kg will be tested with the goal of identifying a dose that gives 50% IFNα signature suppression for at least 4 weeks.

Efficacy can be measured by any acceptable method. Acceptable methods include, but are not limited to microarray analysis of PBMCs (efficacy is established upon extinction of the interferon signature), flow cytometry of PBMCs (efficacy is established by increased T/B lymphocyte counts), decreased plasmacytosis and decreased presence of immature neutrophils or cytokine multiplex analysis in serum by use of luminex analysis.

Biological Deposits. The ACO-1 through ACO-6 hybridoma cell lines were deposited with the American Type Culture Collection, 10801 University Blvd., Manassas, Va. 20110-2209, USA (ATCC), and were accorded the deposit numbers listed in Table 10 below.

TABLE 10

| Hybridoma cell line | ATCC Deposit No. | Deposit Date |
|---|---|---|
| ACO-1 | PTA-6557 | Feb. 08, 2005 |
| ACO-2 | PTA-6558 | Feb. 08, 2005 |
| ACO-3 | PTA-6559 | Feb. 08, 2005 |
| ACO-4 | PTA-6560 | Feb. 08, 2005 |
| ACO-5 | PTA-6561 | Feb. 08, 2005 |
| ACO-6 | PTA-6562 | Feb. 08, 2005 |

These deposits were made under the provisions of the Budapest Treaty on the International Recognition of the Deposit of Microorganisms for the Purpose of Patent Procedure and the Regulations there under (Budapest Treaty). This assures maintenance of a viable culture of the deposit for 30 years from the date of deposit. The deposit will be made available by ATCC under the terms of the Budapest Treaty, and subject to an agreement between Baylor Research Institute and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the Commissioner for Patents to be entitled thereto according to 35 U.S.C. §122 and the Commissioner's rules pursuant thereto (including 37 C.F.R. §1.14 with particular reference to 8660G 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a licensee to practice the invention in contravention of the rights granted under the authority of any government in accordance with the patent laws.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications, and in particular relevant portions thereof, are herein incorporated by reference to the same extent as if each individual publication or patent application was specifically and individually indicated to be incorporated by reference.

In the claims, all transitional phrases such as "comprising," "including," "carrying," "having," "containing," "involving," and the like are to be understood to be open-ended, i.e., to mean including but not limited to. Only the transitional phrases "consisting of" and "consisting essentially of," respectively, shall be closed or semi-closed transitional phrases.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for treating a disease or condition associated with increased expression of at least one IFNα protein subtype selected from the group consisting of protein subtypes A, 2, B2, C, F, G, H2, I, J1, K, 4a, 4b and WA in a subject comprising administering to a subject having said disease or condition an effective amount of an antibody selected from the group consisting of:
   a) an anti-interferon alpha antibody produced by the hybridoma deposited with the ATCC as Accession No. PTA-6557;
   b) a humanized antibody that is a humanized form of the anti-interferon alpha antibody produced by the hybridoma deposited with the ATCC as Accession No. PTA-6557;
   c) a humanized antibody that is a humanized form of the antibody ACO-1;
   d) a humanized antibody that is an antibody fragment of a humanized form of the anti-interferon alpha antibody produced by the hybridoma deposited with the ATCC as Accession No. PTA-6557, wherein the antibody fragment specifically neutralizes a bioactivity of at least ten interferon alpha protein subtypes selected from the group consisting of IFNα protein subtypes A, 2, B2, C, F, G, H2, I, J1, K, 4a, 4b and WA, but does not significantly neutralize said bioactivity of IFNα protein subtype D, wherein said bioactivity is activation of the MxA promoter or antiviral activity;
   e) the humanized antibody of (d) that is an Fab, Fab', F(ab')$_2$, Fv or sFv fragment;
   f) an antibody comprising at least one light chain that comprises the CDRs:
      $V_L1$ having the amino acid sequence of SEQ ID NO:12;
      $V_L2$ having the amino acid sequence of SEQ ID NO:14; and
      $V_L3$ having the amino acid sequence of SEQ ID NO:16; and
   at least one heavy chain that comprises the CDRs:
      $V_H1$ having the amino acid sequence of SEQ ID NO:4;
      $V_H2$ having the amino acid sequence of SEQ ID NO:6;
      $V_H3$ having the amino acid sequence of SEQ ID NO:8; and
   g) the antibody of any of (a) through (f) that is an IgG4 isotype antibody,
   wherein said disease or condition is selected from the group consisting of Systemic Lupus Erythematosus (SLE), type 1 diabetes, and psoriasis, and whereby at least one symptom of said disease or condition is treated or ameliorated.

2. The method of claim 1, wherein the disease is SLE.

3. The method of claim 1, wherein the disease is psoriasis.

4. The method of claim 1, wherein the antibody is a humanized antibody that is a humanized form of the anti-interferon alpha antibody produced by the hybridoma deposited with the ATCC as Accession No. PTA-6557.

5. The method of claim 1, wherein the antibody is a humanized antibody that is a humanized form of the antibody ACO-1.

6. A method of neutralizing at least one IFNα protein subtype in the blood of a subject, wherein the IFNα protein subtype is selected from the group consisting of protein subtypes A, 2, B2, C, F, G, H2, I, J1, K, 4a, 4b and WA, and wherein said method comprises administering to said subject an effective amount of an antibody selected from the group consisting of:
   a) an anti-interferon alpha antibody produced by the hybridoma deposited with the ATCC as Accession No. PTA-6557;
   b) a humanized antibody that is a humanized form of the anti-interferon alpha antibody produced by the hybridoma deposited with the ATCC as Accession No. PTA-6557;

c) a humanized antibody that is a humanized form of the antibody ACO-1;

d) a humanized antibody that is an antibody fragment of a humanized form of the anti-interferon alpha antibody produced by the hybridoma deposited with the ATCC as Accession No. PTA-6557, wherein the antibody fragment specifically neutralizes a bioactivity of at least ten interferon alpha protein subtypes selected from the group consisting of IFNα protein subtypes A, 2, B2, C, F, G, H2, I, J1, K, 4a, 4b and WA, but does not significantly neutralize said bioactivity of IFNα protein subtype D, wherein said bioactivity is activation of the MxA promoter or antiviral activity;

e) the humanized antibody of (d) that is an Fab, Fab', F(ab')$_2$, Fv or sFv fragment;

f) an antibody comprising at least one light chain that comprises the CDRs:
$V_L1$ having the amino acid sequence of SEQ ID NO:12;
$V_L2$ having the amino acid sequence of SEQ ID NO:14; and
$V_L3$ having the amino acid sequence of SEQ ID NO:16; and at least one heavy chain that comprises the CDRs:
$V_H1$ having the amino acid sequence of SEQ ID NO:4;
$V_H2$ having the amino acid sequence of SEQ ID NO:6;
$V_H3$ having the amino acid sequence of SEQ ID NO:8; and g) the antibody of any of (a) through (f) that is an IgG4 isotype antibody, wherein said subject has a disease or condition selected from the group consisting of Systemic Lupus Erythematosus (SLE), type 1 diabetes, AIDS; and psoriasis, and wherein at least one IFNα protein subtype in the blood of said subject is neutralized.

7. The method of claim 6, wherein said subject has SLE.

8. The method of claim 6, wherein said subject has psoriasis.

9. The method of claim 6, wherein the antibody is a humanized antibody that is a humanized form of the anti-interferon alpha antibody produced by the hybridoma deposited with the ATCC as Accession No. PTA-6557.

10. The method of claim 6, wherein the antibody is a humanized antibody that is a humanized form of the antibody ACO-1.

11. The method of claim 1, wherein the disease is type 1 diabetes.

12. The method of claim 6, wherein said subject has type 1 diabetes.

* * * * *